(12) United States Patent
Sharp et al.

(10) Patent No.: US 11,110,067 B2
(45) Date of Patent: Sep. 7, 2021

(54) INHIBITION OF MAMMALIAN TARGET OF RAPAMYCIN

(71) Applicants: THE BOARD OF REGENTS OF THE UNIVERSITY OF TEXAS SYSTEM, Austin, TX (US); Southwest Research Institute, San Antonio, TX (US)

(72) Inventors: Zelton Dave Sharp, San Antonio, TX (US); John R. Strong, San Antonio, TX (US); Veronica Galvan, San Antonio, TX (US); Salvatore Oddo, San Antonio, TX (US); Herbert G. Wheeler, Boerne, TX (US)

(73) Assignees: The Board of Regents of the University of Texas System, Austin, TX (US); Southwest Research Institute, San Antonio, TX (US)

( * ) Notice: Subject to any disclaimer, the term of this patent is extended or adjusted under 35 U.S.C. 154(b) by 0 days.

(21) Appl. No.: 16/552,380

(22) Filed: Aug. 27, 2019

(65) Prior Publication Data
US 2020/0054576 A1 Feb. 20, 2020

Related U.S. Application Data

(63) Continuation of application No. 13/128,800, filed as application No. PCT/US2009/064044 on Nov. 11, 2009, now abandoned.

(60) Provisional application No. 61/113,481, filed on Nov. 11, 2008.

(51) Int. Cl.
| | | |
|---|---|---|
| A61K 31/436 | (2006.01) | |
| A61K 31/00 | (2006.01) | |
| A61K 45/06 | (2006.01) | |
| A61K 9/50 | (2006.01) | |
| A61K 9/16 | (2006.01) | |

(52) U.S. Cl.
CPC .......... *A61K 31/00* (2013.01); *A61K 9/1635* (2013.01); *A61K 9/5026* (2013.01); *A61K 31/436* (2013.01); *A61K 45/06* (2013.01)

(58) Field of Classification Search
CPC ... A61K 31/436; A61K 9/1635; A61K 9/5026
See application file for complete search history.

(56) References Cited

U.S. PATENT DOCUMENTS

| | | | |
|---|---|---|---|
| 3,929,992 | A | 12/1975 | Sehgal et al. |
| 3,993,749 | A | 11/1976 | Sehgal et al. |
| 4,316,885 | A | 2/1982 | Rakhit |
| 4,401,653 | A | 8/1983 | Eng |
| 4,460,722 | A | 7/1984 | Igarashi et al. |
| 4,885,171 | A | 12/1989 | Surendra et al. |
| 5,023,262 | A | 6/1991 | Caufield et al. |
| 5,023,263 | A | 6/1991 | Von Burg |
| 5,023,264 | A | 6/1991 | Caufield et al. |
| 5,066,493 | A | 11/1991 | Sehgal et al. |
| 5,078,999 | A | 1/1992 | Warner et al. |
| 5,080,899 | A | 1/1992 | Sturm et al. |
| 5,100,883 | A | 3/1992 | Schiehser |
| 5,100,899 | A | 3/1992 | Calne |
| 5,102,876 | A | 4/1992 | Caufield |
| 5,118,677 | A | 6/1992 | Caufield |
| 5,118,678 | A | 6/1992 | Kao et al. |
| 5,120,725 | A | 6/1992 | Kao et al. |
| 5,120,726 | A | 6/1992 | Failli et al. |
| 5,120,727 | A | 6/1992 | Kao et al. |
| 5,120,842 | A | 6/1992 | Failli et al. |
| 5,130,307 | A | 7/1992 | Failli et al. |
| 5,138,051 | A | 8/1992 | Hughes et al. |
| 5,151,413 | A | 9/1992 | Caufield et al. |
| 5,162,333 | A | 11/1992 | Failli et al. |
| 5,164,399 | A | 11/1992 | Failli et al. |
| 5,169,851 | A | 12/1992 | Hughes et al. |
| 5,177,203 | A | 1/1993 | Failli et al. |
| 5,194,447 | A | 3/1993 | Kao |
| 5,202,332 | A | 4/1993 | Hughes et al. |
| 5,206,018 | A | 4/1993 | Sehgal et al. |

(Continued)

FOREIGN PATENT DOCUMENTS

| | | |
|---|---|---|
| CA | 2572100 | 6/2007 |
| WO | WO 1995/031194 | 11/1995 |

(Continued)

OTHER PUBLICATIONS

Khan ("A pH-Dependent Colon-Targeted Oral Drug Delivery System Using Methacrylic Acid Copolymers. II. Manipulation of Drug Release Using Eudragit® L100 and Eudragit S100 Combinations." Drug Development and Industrial Pharmacy, 26(5), 549-554 (2000)). (Year: 2000).*

Austad, Steven, "Mixed results for dieting monkeys." Nature. Sep. 13, 2012. vol. 489:210-211.

Blagosklonny, "Aging and immortality: quasi-programmed senescence and its pharmacologic inhibition," Cell Cycle. Sep. 2006;5(18):2087-102.

Blagosklonny, "An anti-aging drug today: from senescence-promoting genes to anti-aging pill," Drug Discov Today. Mar. 2007;12(5-6):218-24.

(Continued)

*Primary Examiner* — Jeffrey S Lundgren
*Assistant Examiner* — Chris E Simmons
(74) *Attorney, Agent, or Firm* — Norton Rose Fulbright US LLP

(57) ABSTRACT

Disclosed are microcapsules that include an inhibitor of the mammalian target of rapamycin (mTOR) within the microcapsules, and pharmaceutical compositions and kits that include the microcapsules. Also disclosed are methods for treating or preventing an age-related disease, condition, or disorder in a subject that involve administering to a subject a pharmaceutically effective amount of microcapsules that includes an inhibitor of mTOR within the microcapsules.

7 Claims, 39 Drawing Sheets

(56) References Cited

U.S. PATENT DOCUMENTS

| | | |
|---|---|---|
| 5,221,670 A | 6/1993 | Caufield |
| 5,221,740 A | 6/1993 | Hughes |
| 5,233,036 A | 8/1993 | Hughes |
| 5,260,299 A | 11/1993 | Failli et al. |
| 5,260,300 A | 11/1993 | Hu |
| 5,262,423 A | 11/1993 | Kao |
| 5,262,424 A | 11/1993 | Kao |
| 5,286,731 A | 2/1994 | Caufield et al. |
| 5,288,711 A | 2/1994 | Mitchell et al. |
| 5,302,584 A | 4/1994 | Kao et al. |
| 5,310,903 A | 5/1994 | Goulet et al. |
| 5,321,009 A | 6/1994 | Baeder et al. |
| 5,344,833 A | 9/1994 | Hughes |
| 5,346,893 A | 9/1994 | Failli et al. |
| 5,358,944 A | 10/1994 | Caufield |
| 5,362,718 A | 11/1994 | Skotnicki et al. |
| 5,373,014 A | 12/1994 | Failli et al. |
| 5,378,696 A | 1/1995 | Caufiled |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,446,048 A | 8/1995 | Failli et al. |
| 5,463,048 A | 10/1995 | Skotnicki et al. |
| 5,480,988 A | 1/1996 | Failli et al. |
| 5,480,989 A | 1/1996 | Kao et al. |
| 5,484,790 A | 1/1996 | Failli et al. |
| 5,484,791 A | 1/1996 | Failli et al. |
| 5,486,522 A | 1/1996 | Failli et al. |
| 5,486,523 A | 1/1996 | Failli et al. |
| 5,486,524 A | 1/1996 | Failli et al. |
| 5,488,054 A | 1/1996 | Failli et al. |
| 5,489,595 A | 2/1996 | Failli et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,504,204 A | 4/1996 | Failli et al. |
| 5,504,291 A | 4/1996 | Goble et al. |
| 5,508,285 A | 4/1996 | Nelson et al. |
| 5,508,286 A | 4/1996 | Skotnicki et al. |
| 5,508,290 A | 4/1996 | Nelson et al. |
| 5,508,399 A | 4/1996 | Kao et al. |
| 5,516,780 A | 5/1996 | Skotnicki et al. |
| 5,519,031 A | 5/1996 | Skotnicki et al. |
| 5,521,194 A | 5/1996 | Nelson et al. |
| 5,525,610 A | 6/1996 | Caufield et al. |
| 5,530,007 A | 6/1996 | Kao et al. |
| 5,530,121 A | 6/1996 | Kao et al. |
| 5,532,355 A | 7/1996 | Skotnicki et al. |
| 5,536,729 A | 7/1996 | Waranis et al. |
| 5,541,191 A | 7/1996 | Skotnicki et al. |
| 5,541,192 A | 7/1996 | Skotnicki et al. |
| 5,550,133 A | 8/1996 | Failli et al. |
| 5,552,160 A | 9/1996 | Liversidge et al. |
| 5,559,112 A | 9/1996 | Skotnicki et al. |
| 5,559,119 A | 9/1996 | Skotnicki et al. |
| 5,559,120 A | 9/1996 | Kao et al. |
| 5,559,121 A | 9/1996 | Harrison et al. |
| 5,559,122 A | 9/1996 | Nelson et al. |
| 5,561,138 A | 10/1996 | Armstrong |
| 5,563,145 A | 10/1996 | Failli et al. |
| 5,567,709 A | 10/1996 | Skotnicki et al. |
| 5,575,987 A | 11/1996 | Kamei |
| 5,637,590 A | 6/1997 | Skotnicki et al. |
| 5,665,772 A | 9/1997 | Cottens et al. |
| 5,780,462 A | 7/1998 | Lee et al. |
| 5,891,469 A | 4/1999 | Amselem |
| 5,912,253 A | 6/1999 | Cottens et al. |
| 5,922,730 A | 7/1999 | Hu et al. |
| 5,932,243 A | 8/1999 | Fricker et al. |
| 5,955,457 A | 9/1999 | Lee et al. |
| 5,985,890 A | 11/1999 | Cottens et al. |
| 5,989,591 A | 11/1999 | Nagi |
| 6,004,973 A | 12/1999 | Guitard et al. |
| 6,015,809 A | 1/2000 | Zhu et al. |
| 6,197,781 B1 | 3/2001 | Guitard et al. |
| 6,200,985 B1 | 3/2001 | Cottens et al. |
| 6,204,243 B1 | 3/2001 | Posanksi |
| 6,228,396 B1 | 5/2001 | Watts |
| RE37,421 E | 10/2001 | Holt et al. |
| 6,329,386 B1 | 12/2001 | Mollison |
| 6,399,625 B1 | 6/2002 | Zhu |
| 6,440,990 B1 | 8/2002 | Cottens et al. |
| 6,475,518 B1 | 11/2002 | Baumgart et al. |
| 6,486,099 B2 | 11/2002 | Igari et al. |
| 6,503,883 B1 | 1/2003 | Posanski |
| 6,537,195 B2 | 3/2003 | Forman |
| 6,555,132 B1 | 4/2003 | Brox et al. |
| 6,569,463 B2 | 5/2003 | Patel et al. |
| 6,592,916 B2 | 7/2003 | Soeda et al. |
| 6,596,268 B1 | 7/2003 | Coffey et al. |
| 6,605,298 B1 | 8/2003 | Leigh et al. |
| 6,649,157 B2 | 11/2003 | Coffey et al. |
| 6,653,256 B1 | 11/2003 | Wolf et al. |
| 6,670,355 B2 | 12/2003 | Azrolan et al. |
| 6,677,357 B2 | 1/2004 | Zhu et al. |
| 6,680,330 B2 | 1/2004 | Zhu et al. |
| 6,849,651 B2 | 2/2005 | Danishefsky et al. |
| 6,923,988 B2 | 8/2005 | Patel et al. |
| 6,929,818 B2 | 8/2005 | Luthra et al. |
| 6,936,644 B2 | 8/2005 | Gilleo |
| 6,956,043 B2 | 10/2005 | Guitard et al. |
| 6,974,473 B2 | 12/2005 | Barclay et al. |
| 7,008,979 B2 | 3/2006 | Schottman et al. |
| 7,037,582 B2 | 5/2006 | Xing et al. |
| 7,041,046 B2 | 5/2006 | Forman |
| 7,084,171 B2 | 8/2006 | Grainger et al. |
| 7,132,458 B2 | 11/2006 | Burton et al. |
| 7,160,867 B2 | 1/2007 | Abel et al. |
| 7,220,755 B2 | 5/2007 | Betts et al. |
| 7,241,771 B2 | 7/2007 | Zhu |
| 7,268,144 B2 | 9/2007 | Gu et al. |
| 7,271,177 B2 | 9/2007 | Benjamin et al. |
| 7,273,874 B2 | 9/2007 | Graziani et al. |
| 7,279,562 B2 | 10/2007 | Molnar-Kimber |
| 7,282,505 B2 | 10/2007 | Zhu et al. |
| 7,292,885 B2 | 11/2007 | Scott et al. |
| 7,304,033 B2 | 12/2007 | Larsen et al. |
| 7,445,916 B2 | 11/2008 | Gu et al. |
| 7,446,111 B2 | 11/2008 | Benjamin et al. |
| 7,452,723 B2 | 11/2008 | Coffey et al. |
| 7,455,853 B2 | 11/2008 | Mollison et al. |
| 7,470,682 B2 | 12/2008 | Graziani et al. |
| 7,476,678 B2 | 1/2009 | Graziani et al. |
| 7,488,444 B2 | 2/2009 | Furst et al. |
| 7,511,070 B2 | 3/2009 | Grainger et al. |
| 7,517,342 B2 | 4/2009 | Scott et al. |
| 7,517,362 B2 | 4/2009 | Shanley et al. |
| 7,519,418 B2 | 4/2009 | Scott et al. |
| 7,538,119 B2 | 5/2009 | Gu et al. |
| 7,560,457 B2 | 7/2009 | Graziani et al. |
| 7,576,903 B2 | 8/2009 | Yamamoto et al. |
| 8,007,831 B2 | 8/2011 | Lewis et al. |
| 8,053,444 B2 | 11/2011 | Reven et al. |
| 2001/0026807 A1 | 10/2001 | Watts |
| 2002/0009473 A1 | 1/2002 | Tebbe |
| 2003/0215496 A1* | 11/2003 | Patel ............ A61K 47/10 424/452 |
| 2004/0010002 A1 | 1/2004 | Wasik et al. |
| 2004/0074089 A1 | 4/2004 | Gilleo |
| 2004/0121155 A1 | 6/2004 | Matsunami et al. |
| 2005/0090553 A1 | 4/2005 | Shapiro |
| 2005/0113282 A1 | 5/2005 | Parekh et al. |
| 2006/0115533 A1 | 6/2006 | Guitard et al. |
| 2006/0121122 A1 | 6/2006 | Nakajima et al. |
| 2006/0210638 A1 | 9/2006 | Liversidge et al. |
| 2006/0234053 A1 | 10/2006 | Yamamoto et al. |
| 2006/0251720 A1 | 11/2006 | Penhasi |
| 2006/0264453 A1 | 11/2006 | Mudumba et al. |
| 2007/0082829 A1 | 4/2007 | Smets et al. |

(56) References Cited

U.S. PATENT DOCUMENTS

| | | |
|---|---|---|
| 2007/0138673 A1 | 6/2007 | Lee et al. |
| 2007/0142423 A1 | 6/2007 | Graziani et al. |
| 2007/0185150 A1 | 8/2007 | Bedrosian |
| 2007/0203168 A1 | 8/2007 | Zhao |
| 2007/0203169 A1 | 8/2007 | Zhao |
| 2007/0203170 A1 | 8/2007 | Zhao |
| 2007/0203171 A1 | 8/2007 | Zhao |
| 2007/0203172 A1 | 8/2007 | Zhao |
| 2007/0225313 A1 | 9/2007 | Zhao |
| 2007/0280992 A1 | 12/2007 | Margaron et al. |
| 2008/0022965 A1 | 1/2008 | Bysreen et al. |
| 2008/0069797 A1 | 3/2008 | Roncarolo et al. |
| 2008/0085880 A1 | 4/2008 | Viswanath et al. |
| 2008/0091008 A1 | 4/2008 | Viswanath et al. |
| 2008/0138405 A1 | 6/2008 | Raheja et al. |
| 2008/0182867 A9 | 7/2008 | Wasik et al. |
| 2008/0188511 A1 | 8/2008 | Beckmann et al. |
| 2008/0193653 A1 | 8/2008 | Oh |
| 2008/0234380 A1 | 9/2008 | Shapiro |
| 2008/0249123 A1 | 10/2008 | Gu et al. |
| 2008/0275076 A1 | 11/2008 | Holm et al. |
| 2010/0150864 A1 | 6/2010 | Hickman et al. |
| 2011/0104256 A1 | 5/2011 | Wang et al. |
| 2011/0105387 A1 | 5/2011 | Wu et al. |
| 2011/0195966 A1 | 8/2011 | Garcia-Echeverria et al. |
| 2011/0293731 A1 | 12/2011 | Lewis et al. |
| 2012/0064143 A1 | 3/2012 | Sharp et al. |
| 2012/0276169 A1 | 11/2012 | Choi et al. |

FOREIGN PATENT DOCUMENTS

| | | |
|---|---|---|
| WO | WO 2006/066063 | 6/2006 |
| WO | WO 2007/093346 | 8/2007 |
| WO | WO 2008/022256 | 2/2008 |
| WO | WO 2010/009335 | 1/2010 |

OTHER PUBLICATIONS

Cao et al., "Toll-like receptor-mediated induction of type I interferon in plasmacytoid dendritic cells requires the rapamycin-sensitive PI(3)K-mTOR-p70S6K pathway," Nat Immunol. Oct. 2008;9(10):1157-64.

Carter et al., "Molecular mechanisms of life- and health-span extension: role of calorie restriction and exercise intervention," Appl Physiol Nutr Metab. Oct. 2007;32(5):954-66.

Demetrius, Lloyd (Aging in Mouse and Human Systems: A Comparative Study Ann. N.Y. Acad. Sci. 1067: 66-82 (2006)).

Estep et al., "Short-term calorie restriction in male mice feminizes gene expression and alters key regulators of conserved aging regulatory pathways," PLoS One. 2009;4(4):e5242.

European Search Report and Written Opinion issued in European Application No. 0926677.8, dated May 22, 2012.

Fajadet et al., "Randomized, double-blind, multicenter study of the Endeavor zotarolimus-eluting phosphorylcholine-encapsulated stent for treatment of native coronary artery lesions. Clinical and angiographic results of the Endeavor II Trial," Minerva Cardioangiol. Feb. 2007;55(1):1-18.

Fujishita, et al., "Inhibition of the mTORC1 pathway suppresses intestinal polyp formation and reduces mortality in Apcdelta716 mice" PNAS. 105(36):13544-9, 2008.

Guertin and Sabatini, "The pharmacology of mTOR inhibition," Sci. Signal., 2(67):pe24, 2009.

Hansen et al., "Lifespan extension by conditions that inhibit translation in Caenorhabditis elegans," Aging Cell, 6:95-110, 2007.

Harrison et al., "Rapamycin fed late in life extends lifespan in genetically heterogeneous mice," Letters, 460:392-395, 2009.

Hasty, et al., "eRapa Restores a Normal Life Span in a FAP Mouse Model." Cancer Prev Res. 7:169-178, 2014.

Jhunjhunwala et al., "Delivery of rapamycin to dendritic cells using degradable microparticles," J Control Release. Feb. 10, 2009;133(3):191-7.

Kapahi et al., "Regulation of lifespan in Drosophila by modulation of genes in the TOR signaling pathway," Curr. Biol., 14:885-890, 2004.

Koehl et al., "Rapamycin inhibits oncogenic intestinal ion channels and neoplasia in APCMIN/+ mice," Oncogene (2010), vol. 29, pp. 1553-1560.

Leung et al. (Can Urol Assoc J 2012; 6(5):367-73; http://dx.doi.org/10.5489/cuaj.11161).

Miller et al., "An Aging Interventions Testing Program: study design and interim report," Aging Cell, 6:565-575, 2007.

Nadon et al., "Design of aging intervention studies: the NIA interventions testing program," AGE, 30(4):187-199, 2008.

Office Action in Canadian Application No. 2,743,491 dated Jul. 17, 2015.

PCT International Preliminary Report on Patentability issued in International Application No. PCT/US2009/064044, dated May 26, 2011.

PCT International Search Report and Written Opinion issued in International Application No. PCT/US2009/064044, dated Jun. 25, 2010.

Powers III et al., "Extension of chronological life span in yeast by decreased TOR pathway signaling," Genes & Development, 20:174-184, 2006.

Rao et al., "Mammalian Target of Rapamycin (mTOR) Inhibitors as Anti-Cancer Agents," Current Cancer Drug Targets, 4(8): 621-635, 2004.

Shavelle et al (J Insur Med. 2009; 41(3):178-90).

Soerjomataram et al. (Cancer Causes Control (Sep. 2012); 23(9): 1421-1428).

Tabernero, et al. (J of Clinical Oncology, 26(10); Apr. 2008).

Tsang et al., "Targeting mammalian target of rapamycin (mTOR) for health and diseases," Drug Discovery Today, 12(3/4):112-124, 2007.

Wislez et al. (Cancer Res Apr. 15, 2005 65; 3226).

Yang Wenjun & Wen Longping, "Small Molecule Autophagy Inducers" Progress in Chemistry. 19(12):2013-6, 2007—English Abstract Only.

\* cited by examiner

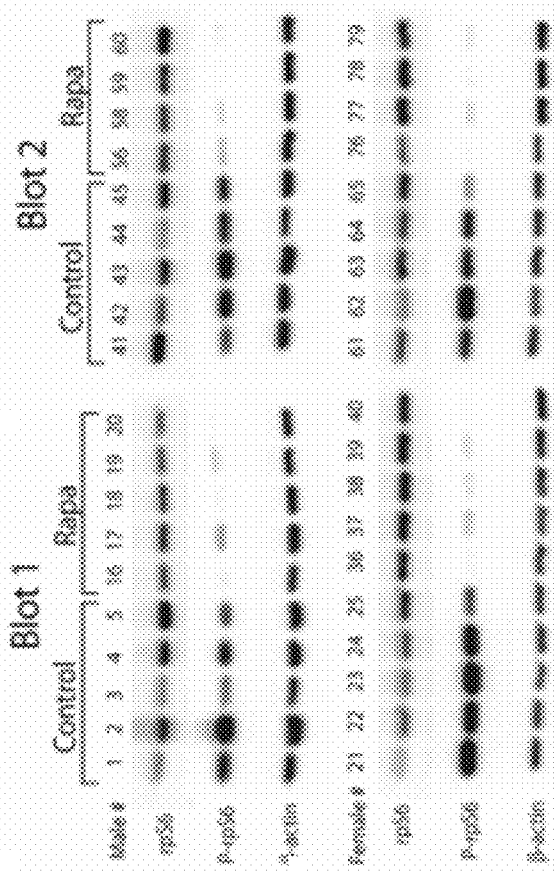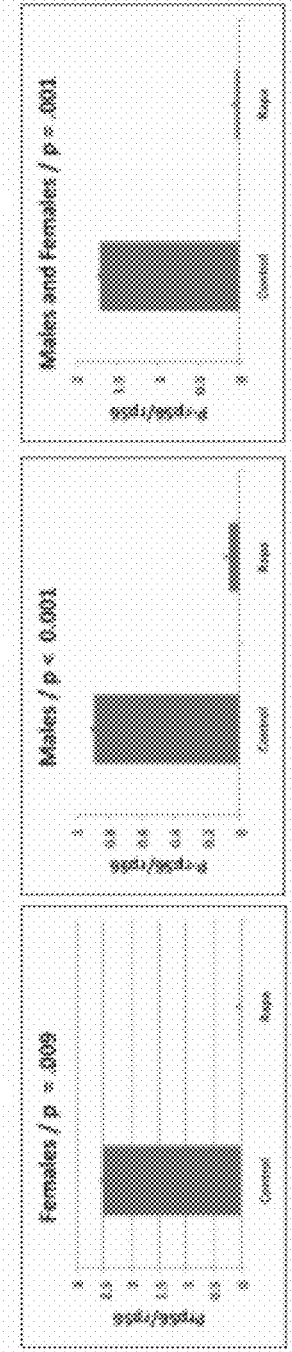
FIG. 5

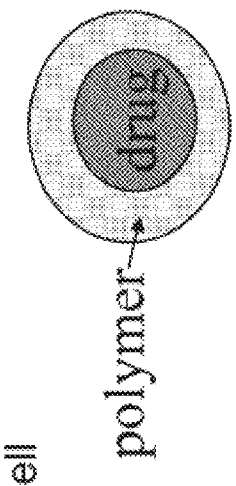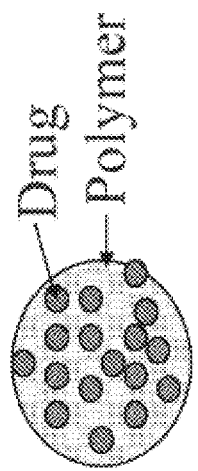
FIG. 16

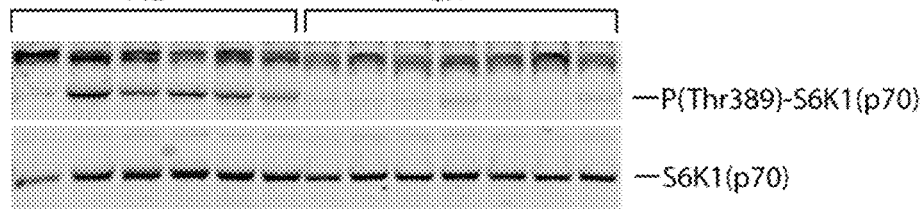
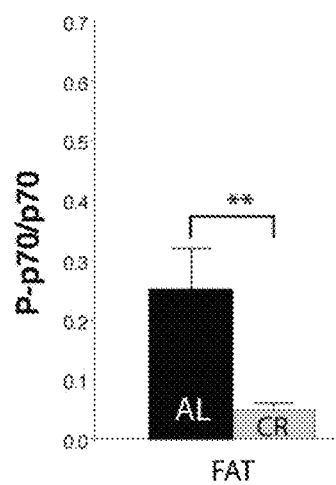
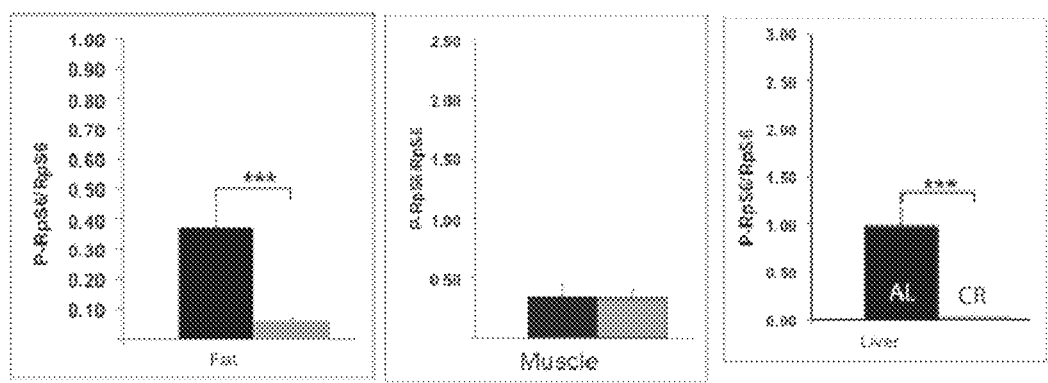
FIG. 18

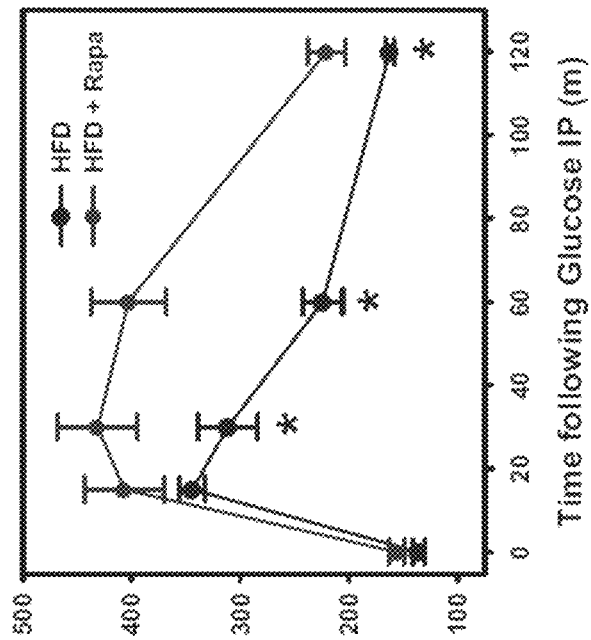
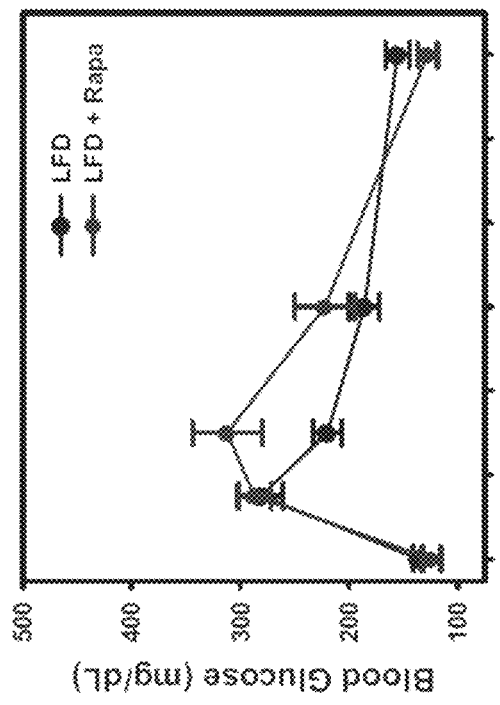
FIG. 26

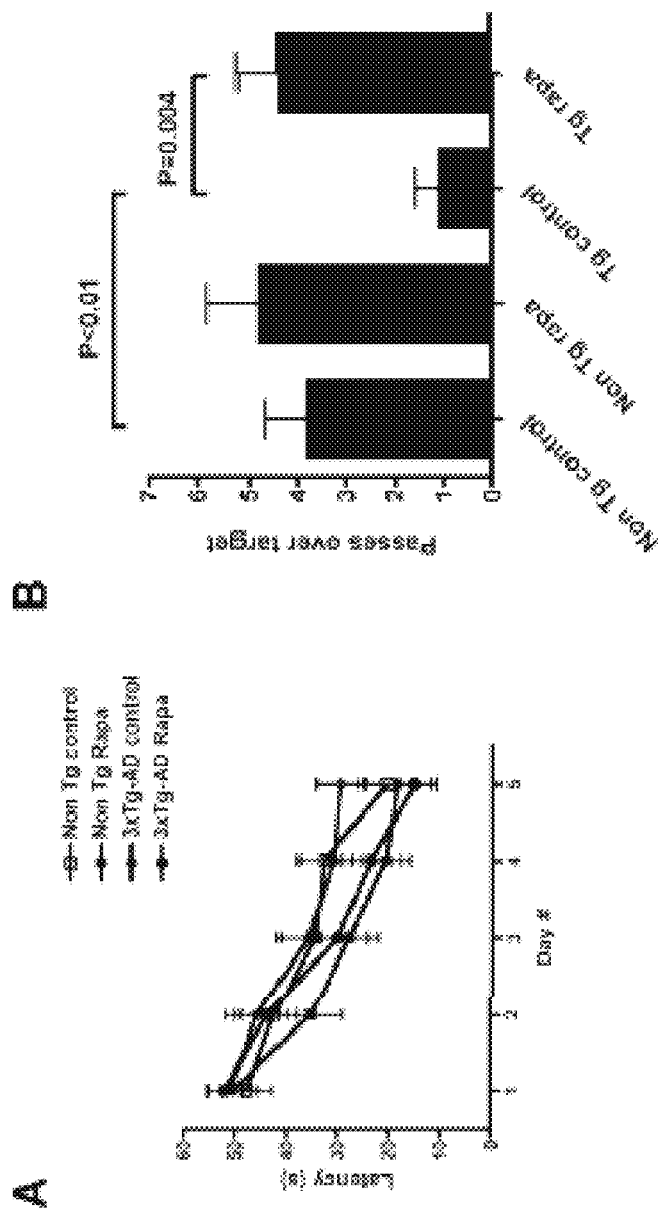
FIGs. 28A-B

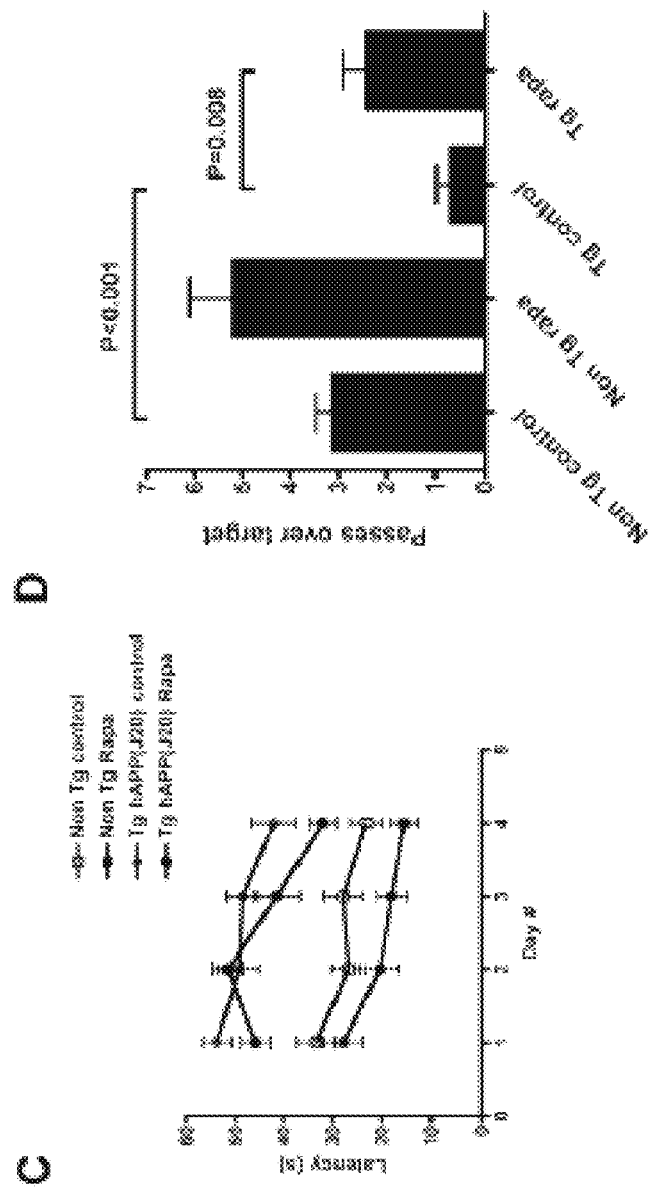
FIGs. 28C-D

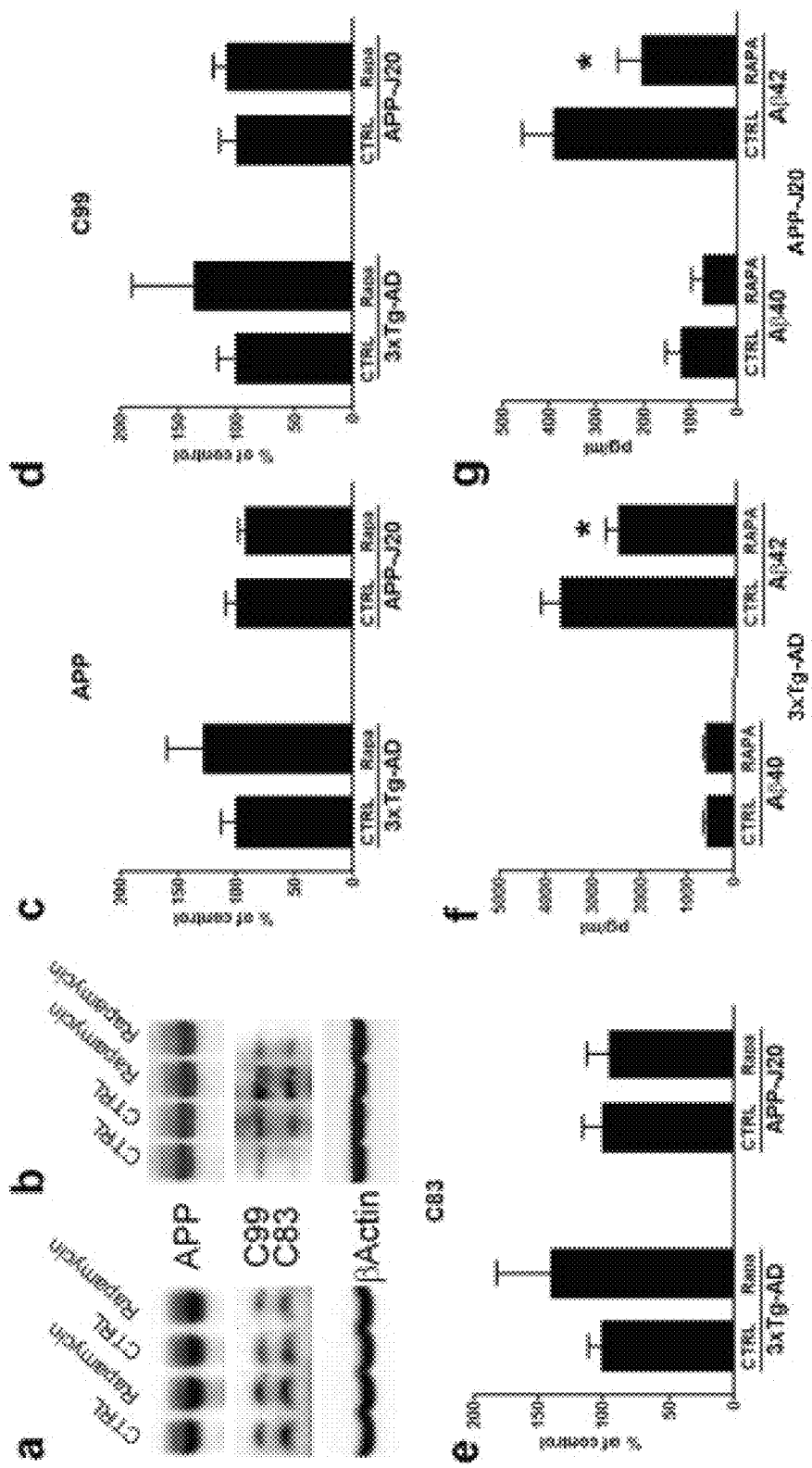
FIGs. 29A-G

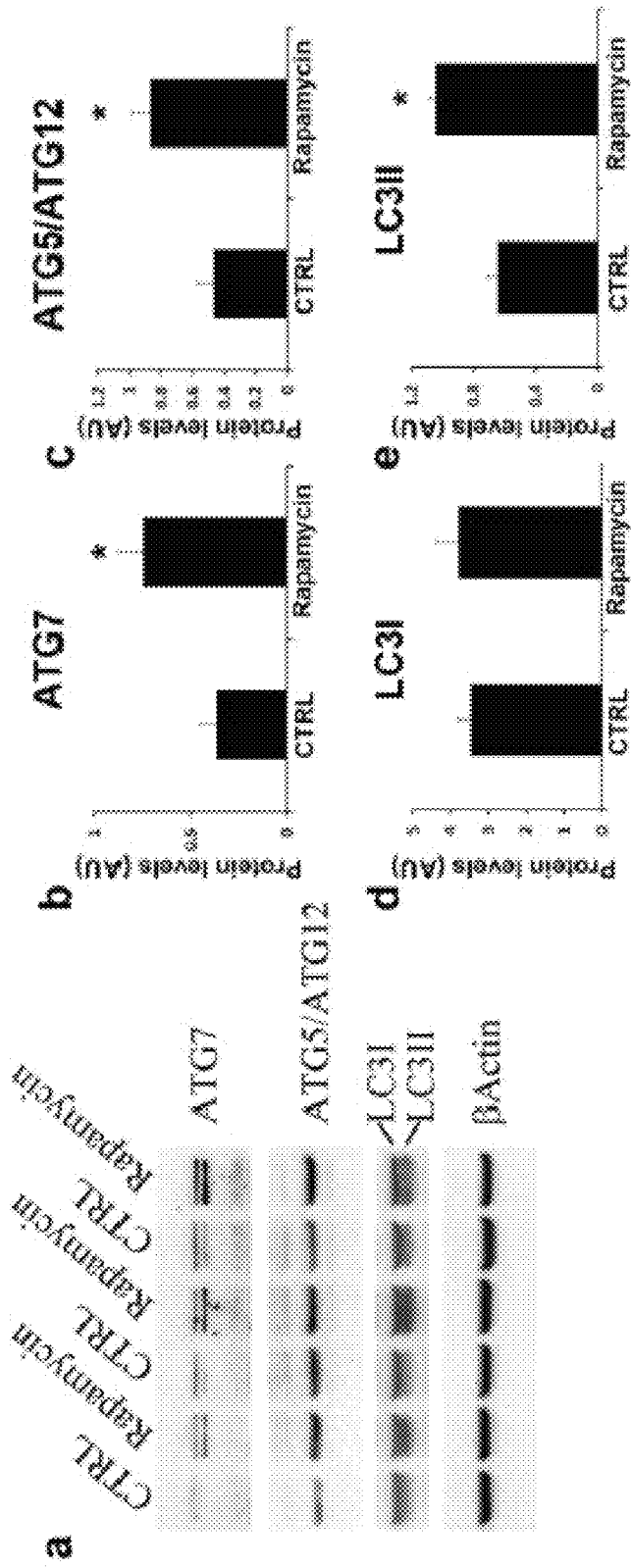
FIGs. 31A-E

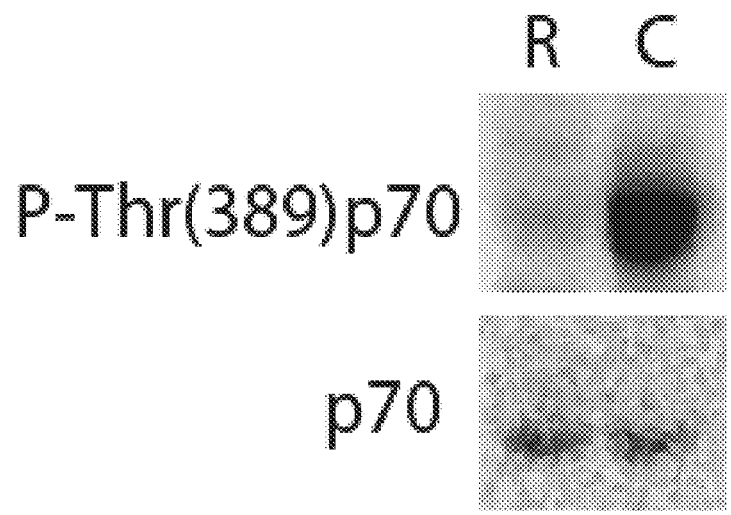
FIG. 35
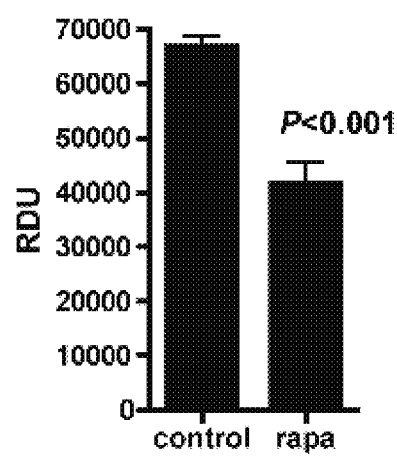
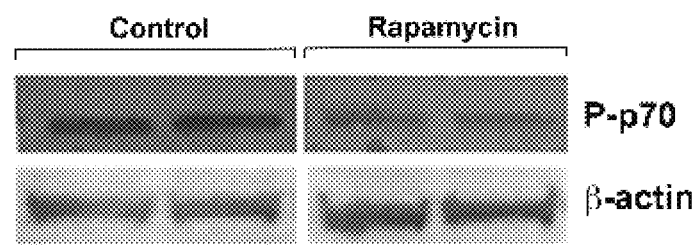
FIGs. 36A-B

INHIBITION OF MAMMALIAN TARGET OF RAPAMYCIN

This application is a continuation of U.S. application Ser. No. 13/128,800 filed on May 11, 2011, which is a national phase application under 35 U.S.C. § 371 of International Application No. PCT/US2009/064044 filed on Nov. 11, 2009, which claims priority to U.S. Application No. 61/113,481 filed on Nov. 11, 2008. The entire contents of each of the above-referenced disclosures are specifically incorporated herein by reference without disclaimer.

This invention was made with the government support under grant numbers AG029729 and AG022307 awarded by the National Institutes of Health. The government has certain rights in the invention.

BACKGROUND OF THE INVENTION

1. Field of the Invention

The present invention relates generally to the fields of pharmacology and the treatment and prevention of age-related disorders. More specifically, the invention relates to microcapsules that include an inhibitor of the mammalian target of rapamycin (mTOR), and methods of treating or preventing age-related diseases, disorders, and conditions in a subject using microcapsules of the present invention.

2. Description of Related Art

Because most deaths in developed nations result from diseases whose incidences rise rapidly with age, interventions that delay aging would benefit human health far more than would preventive measures that affect only specific late-life diseases such as heart disease, cancer or diabetes. There is intense interest in the development of dietary additives that delay aging and increase lifespans.

mTOR and Cancer.

Mammalian TOR is a critical effector in the deregulated signaling pathways associated with cancer (Guertin and Sabatini, 2007; Shaw and Cantley, 2006). Mutations in tsc1 or tsc2 genes, which lead to the hamartomatous syndrome tuberous sclerosis complex (TSC), suggest a molecular connection between mTOR and cancer. mTORC1 is the only known downstream effector common to two of the major signaling pathways in cancer (Ras and PI3K), and which is also integrated with nutrient signaling for regulation of cell growth (mass) (Shaw and Cantley, 2006). Hyperactivated AKT signaling likely mediates oncogenic transformation via mTOR (Skeen et al., 2006).

It has been suggested that a major mTORC1 effector, S6 kinase 1 (S6K1), mediates deleterious effects such as insulin resistance and type II diabetes (Patti and Kahn, 2004; Tremblay et al., 2005b; Tremblay et al., 2005c; Um et al., 2006). Compared to wild type, S6K1-deficient mice demonstrated a reduced rate of growth including less white adipose tissue (WAT) due to smaller cells (Shima et al., 1998). Interestingly, the phenotype of mice deficient for S6K1 includes hypoinsulinemia coupled with increased sensitivity to insulin (Um et al., 2004). Because of increased lipolysis and metabolic rate, these mice appear to be resistant to diet-induced obesity (Um et al., 2004). In muscle cells deficient for S6K1 function, there is an increase in AMP and inorganic phosphates, and a consequent increase in activated AMPK and AMPK-dependent functions including mitochondrial biogenesis and fatty acid ü-oxidation (Aguilar et al., 2007). Concomitant with this response, there is also a decrease in lipid content of cells.

Rapamycin has been shown to act as a potent inhibitor of adipocyte differentiation, an effect reversed by high FK506 concentrations, indicating an operative inhibitory effect mediated by an immunophilin-rapamycin complex (Yeh et al., 1995). A model for the critical role of mTOR and its kinase activity in 3T3-L1 preadipocyte differentiation has been proposed, wherein the mTOR pathway and the phosphatidylinositol 3-kinase/Akt pathway act in parallel during adipogenesis by mediating respectively nutrient availability and insulin signals (Kim and Chen, 2004).

There is the need for more effective treatments of age-related diseases and the need for a greater understanding of agents that may increase lifespan and delay the appearance of age-related disease.

SUMMARY OF THE INVENTION

The present invention is based in part of the finding that a physiological state similar to food and/or growth factor restriction, with retarded aging and reduced incidence of age-related diseases, can be achieved in mammals, including humans, by chronically blocking a central protein complex in the nutrient sensing and growth factor-responding pathway called the mammalian target of rapamycin (mTOR) by formulations of an inhibitor of mTOR in a formulation that is encapsulated. For example, the inventors have found that microencapsulated rapamycin fed late in life extends lifespan in genetically heterogenous mice. Further, microencapsulated rapamycin has been found to rescue cognition and attenuate the pathology in mouse models of Alzheimer disease. Microencapsulation improves therapeutic efficacy compared to formulations that are not encapsulated. Chronic inhibition of mTOR can be applied in improving the health and well being of individuals, including mature adults, by ameliorating several major categories of age-dependent diseases, thereby increasing the quality and quantity of the productive years of life while providing significant economic benefit.

Some embodiments of the present invention concern microcapsules that include a core component that includes an inhibitor of mTOR, wherein the core component is encased in a coating. The inhibitor of mTOR may be an inhibitor of mammalian target of rapamycin complex 1 (mTORC1) or an inhibitor of mammalian target of rapamycin complex 2 (mTORC2). In particular embodiments, the coating provides for delayed release of the inhibitor of mTOR and/or preferential release of the therapeutic agent in the intestinal tract of a subject (i.e., an enteric coating). The enteric coating may be any such coating known to those of ordinary skill in the art. Non-limiting examples of such coatings include Eudragit S100, cellulose acetate phthalate (CAP), a methyl acrylate-methacrylic acid copolymer, cellulose acetate succinate, hydroxy propyl methyl cellulose phthalate, polyvinyl acetate phthalate (PVAP), or a methyl methacrylate-methacrylic acid copolymer. In some particular embodiments, the coating includes Eudragit S100. The coating may include a mixture of one or more of Eudragit S100, cellulose acetate phthalate (CAP), a methyl acrylate-methacrylic acid copolymer, cellulose acetate succinate, hydroxy propyl methyl cellulose phthalate, polyvinyl acetate phthalate (PVAP), and a methyl methacrylate-methacrylic acid copolymer A "microcapsule" as used herein is defined as a vehicle for delivery of a therapeutic agent to a subject which includes one or more cores, where the core(s) are encased in a coating as set forth above. In particular embodiments, the microcapsule includes a single core that is encased in a coating. In further embodiments, the microcapsule includes a plurality of cores encased in a coating where the cores with surrounding coating are aggregated together to form a single drug delivery structure. The core may be a solid or it may be a liquid, and its state may depend upon ambient temperature.

The microcapsules may be of any size or shape. Basic geometrical shapes may be, for example, spheres, rods, cylinders, cubes, cuboids, prism, pyramids, cones, truncated cones and truncated pyramids. Star extrudates, cross extrudates, ribbed extrudates and trilobes are furthermore suitable. Cavities, such as incorporated tubes, may be incorporated into the microcapsule.

The microcapsules may be of regular shape or may have be irregular in shape. The surface of the microcapsule may be smooth, uneven, or jagged. They may be amorphous, spherical, or acicular in shape, depending on the respective method of production. The microcapsules may be formed using any method known to those of ordinary skill in the art. Non-limiting examples of such methods are discussed in greater detail below. In a single dosage that includes microcapsules, the microcapsules may be of uniform size and shape, or may be of variables sizes and shapes.

The microcapsules may be of any size. For example, the maximum diameter of the microcapsule may be about 100 nm, 1 µm, 10 µm, 50 µm, 100 µm, 200 µm, 300 µm, 400 µm, 500 µm, 600 µm, 700 µm, 800 µm, 900 µm, 1 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 1.0 cm or greater, or any range of maximum diameters derivable within the aforementioned maximum diameters. For example, the maximum diameter of the microcapsule may range from about 100 nm to about 1.0 cm. In more particular embodiments, the mean diameter ranges from about 100 µm to about 1 mm. In further embodiments, the mean diameter ranges from about 100 µm to about 0.1 mm.

The microcapsule may comprise at least 5%, at least 10%, at least 20%, at least 30%, at least 40%, at least 50%, at least 60%, at least 70%, at least 80%, at least 90%, at least 95%, at least 99% or more of an mTOR inhibitor by weight (w/w).

The inhibitor of mTOR may be rapamycin or a rapamycin analog. In particular embodiments, the mTOR inhibitor is rapamycin. In more particular embodiments, the mTORC1 is rapamycin and the coating is Eudragit S100. In some embodiments, the inhibitor of mTOR is a competitive inhibitor of the mTOR kinase. These interact directly with the mTOR kinase and do not rely on an intracellular receptor like FKBP12.

Any rapamycin analog known to those of ordinary skill in the art is contemplated for inclusion in the microcapsules of the present invention. Non-limiting examples of rapamycin analogs include everolimus, tacrolimus, CCI-779, ABT-578, AP-23675, AP-23573, AP-23841, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethylrapamycin, or 42-O-(2-hydroxy)ethyl rapamycin. Numerous other examples of rapamycin analogs are discussed in the specification below. The microcapsules of the present invention may include rapamycin and one or more rapamycin analogs, or may include more than one type of rapamycin analog.

In some embodiments, the microcapsules of the present invention include one or more pharmaceutical or nutraceutical agent. Non-limiting examples of such agents include a vitamin, an herbal agent (such as *Ginkgo biloba* or green tea), fish oil (omega 3 fatty acids), an antimicrobial agent, an antioxidant, a drug, or an anti-inflammatory agent. For example, the core component may include a second compound that is vitamin E, vitamin A, an antibacterial antibiotic, an antioxidant, L-carnitine, lipoic acid, metformine, resveratrol, leptine, a non-steroid anti-inflammatory drug, a COX inhibitor, vitamin D, a mineral such as magnesium, calcium, zinc or potassium, a trace element such as molybdenum or iodine, a carotenoid (such as vitamin A), an enzyme such as lipase or amylase, or an amino acid (such as lysine, arginine, taurine, or proline). The drug may be an agent that is known or suspected to be of benefit in treating or preventing an age-related disease, disorder, or condition. For example, the drug may be an agent that is known or suspected to be of benefit in the treatment or prevention of a neurodegenerative disease, memory loss, abnormal glucose metabolism, or cancer. Non-limiting examples of such agents are discussed in the specification below. The core and/or coating of the microcapsules set forth herein may include one or more adjunct materials, such as carriers, binders, and the like that are well-known to those of ordinary skill in the art.

In some embodiments, the microcapsule consists essentially of a core component that comprises rapamycin or a rapamycin analog, wherein the core component is encased in a coating. The coating may be any of the coatings discussed above, and the rapamycin analog may be any of the rapamycin analogs discussed above. Non-limiting examples of coatings include Eudragit S100, cellulose acetate phthalate (CAP), a methyl acrylate-methacrylic acid copolymer, cellulose acetate succinate, hydroxy propyl methyl cellulose phthalate, polyvinyl acetate phthalate (PVAP), or a methyl methacrylate-methacrylic acid copolymer. In particular embodiments, the coating is Eudragit S100. In more particular embodiments, the coating is Eudragit S100 and the core includes rapamycin. The microcapsule may include one or more adjunct materials as discussed above.

The core may include one or more additional components other than one or more inhibitors of mTOR. For example, the core may include the diluents are selected from the group comprising mannitol, lactose, microcrystalline cellulose, dicalcium phosphate, starch, pregelatinized starch, sorbitol or mixtures thereof. The core may include a disintegrant such as sodium starch glycolate, croscarmellose sodium, crospovidone, starch or mixtures thereof. The core may include a binder such as hydroxypropyl cellulose, hydroxy ethyl cellulose, ethyl cellulose, hydroxypropyl methylcellulose, methylcellulose or mixtures thereof. The core may include a lubricant such as calcium stearate, magnesium stearate, sodium stearyl fumarate, talc, colloidal silicon dioxide or mixtures thereof.

Other embodiments of the present invention concern pharmaceutical or nutraceutical compositions for treating or preventing an age-related disease, condition, or disorder that include a microcapsule that includes a core component comprising an inhibitor of mTOR, wherein the core component is encased in a coating. The microcapsule may be any of the microcapsules of the present invention. The pharmaceutical compositions set forth herein may include one or more pharmaceutically acceptable agents, many of which are well-known to those of ordinary skill in the art.

In some embodiments, the microcapsules are formulated with a edible substance. The edible substance may be a food or food additive. The composition may optionally include one or more additional agents that can be applied in the treatment or prevention of any disease, disorder, or health-related condition. For example, the disease may be an age-related disease, such as a neurodegenerative disease, abnormal glucose metabolism, or cancer. The compositions may be formulated with one or more nutraceutical agents, many of which are well-known to those of ordinary skill in the art. For example, the nutraceutical agent may be a vitamin, a nutritional supplement, or an agent derived from herbs or plants that is known or suspected to be of benefit in promoting health and well-being of a subject.

The present invention also concerns methods for treating or preventing an age-related disease, condition, or disorder in a subject, involving administering to a subject a pharmaceutically effective amount of microcapsules of the present invention. The present invention also concerns use of the microcapsules of the present invention to treat or prevent an age-related disease, condition, or disorder in a subject. The subject may be any subject, such as a mammal. Non-limiting examples of mammals include mice, rats, rabbits, dogs, cats, cows, sheep, horses, goats, primates, and humans. In particular embodiments, the subject is a human. The human may be a human who is known or suspected to have an age-related disease. In some embodiments, the human is a human greater than age 50, greater than age 55, greater than age 60, greater than age 65, greater than age 70, greater than age 75, or greater than age 80.

The age-related disease, condition, or disorder can be any disease, condition, or disorder where the prevalence increases with age. Non-limiting examples of age-related diseases include a neurodegenerative disease, a disease associated with abnormal glucose metabolism, and cancer. With respect to cancer, non-limiting examples include breast cancer, lung cancer, prostate cancer, ovarian cancer, brain cancer, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, and leukemia. Non-limiting examples of neurodegenerative diseases include Alzheimer disease, amyotrophic lateral sclerosis (ALS), presenile dementia, senile dementia, Parkinson's disease, Huntington's disease, and memory loss associated with aging.

Other examples of age-related diseases, conditions, or disorders contemplated for treatment or prevention using microcapsules of the present invention include insulin resistance, benign prostatic hyperplasia, hearing loss, osteoporosis, age-related macular degeneration, a skin disease, aging skin, sarcopenia, cardiovascular disease, lipid/carbohydrate metabolism, cancer, and immune disease. The microcapsules set forth herein may be administered to improve life span, improve quality of life, reduce risk of oxidative damage and cell senescence.

The subject may have an existing age-related disease, condition or disorder, or the subject may be at risk of developing an age-related disease, condition or disorder. The at-risk subject may be a subject who has previously received treatment for an age-related disease, condition, or disorder, where the disease, condition, or disorder has previously been successfully treated. The subject may be at risk because of other risk factors, such as genetic risk factors or environmental risk factors.

The present invention also concerns a method of prolonging the lifespan of a mammalian subject that involves administering to a subject an effective amount of microcapsules of the present invention, wherein lifespan is prolonged. Prolongation of lifespan as used herein refers to a greater lifespan of the subject than the subject would otherwise live in the absence of the microcapsules of the present invention. An estimate of the lifespan the subject would have otherwise lived in the absence of the microcapsules can be obtained, for example, from demographic studies, Social Security Administration Life Tables, and scientific literature concerning lifespan. The present invention further concerns methods of reducing the age-related decline in cognition in a mammalian subject that involves administering to the subject an effective amount of microcapsules of the present invention, wherein the age-related decline in cognition is reduced. Reduction in age-related decline of cognition may be assessed by comparing cognition of the subject to a known index of cognition obtained from a control subject or subjects.

The microcapsules may be administered using any method known to those of ordinary skill in the art. Non-limiting examples of routes of administration include orally, by nasogastric tube, rectally, intraperitoneally, topically, subcutaneously, intravenously, intraarterially, intramuscularly, via lavage, and intrathecally. In some embodiments, the microcapsules are administered by combining the microcapsules with a composition that includes an edible substance.

The dose of microcapsules that is administered may be determined by a practitioner using any method known to those of ordinary skill in the art. In some embodiments, the dose of the inhibitor of mTOR is about 1 microgram to about 100 mg per kg body of the subject. Additional information concerning dosage regimens is discussed in the specification below.

Other aspects of the present invention concern methods of making a microcapsule that includes an inhibitor of mTOR that involves applying a pharmaceutical coating to a core particle comprising an inhibitor of mTOR, wherein the core particle becomes coated with the coating. The coating may be an enteric coating. The coating may be any of the coatings discussed above and elsewhere in this specification. In specific embodiments, the coating is Eudragit S100.

Any method known to those of ordinary skill in the art can be used to apply the coating to the particle. In specific embodiments, applying an enteric coating involves use of a spinning disk atomizer, other methods may include pan coating, air-suspension coating, centrifugal extrusion, vibrational nozzle, spray-drying, interfacial polymerization, in situ polymerization, matrix polymerization Further aspects of the present invention concern kits that include a first sealed container that includes a microcapsule or microcapsules of the present invention. The kit may include a first sealed container that includes any of the microcapsules of the present invention. In some embodiments, the kit further includes instructions for use of the microcapsules of the present invention. In some embodiments, the kit further includes a second compound. The second compound may be comprised in the first sealed container, or may be comprised separately such as in a second sealed container.

It should be understood that the foregoing disclosure emphasizes certain specific embodiments of the invention and that all modifications or alternatives equivalent thereto are within the spirit and scope of the invention as set forth in the appended claims. All references cited herein are incorporated by reference in their entirety, for all purposes.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Any embodiment of any of the present medical devices, perfusion systems, and kits may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

FIG. 5. Reduced P-rpS6(Ser240/244) in White Adipose Tissue.

FIG. 16. Microencapsulation.

FIG. 18. Reduced mTOR signaling in calorie-restricted mice.

FIG. 26. Rapamycin causes glucose intolerance in HET3 mice fed a high fat diet.

FIG. 28A, 28B, 28C, 28D. Rapamycin abrogates memory deficits in the 3xTg-AD and the hAPP(J20) mouse models of AD. A and C, The mean latencies in reaching a hidden platform were significantly decreased for rapamycin-fed 3×Tg-AD and hAPP(J20) mice with respect to control-fed Tg groups (*P<0.044; and *P=0.036 respectively). Learning was effective in both hAPP(J20) and 3×Tg-AD groups [F(3,120)=10.29, P<0.0001 and F(4,220)=16.95, P<0.0001 respectively]. No significant interaction was observed between the day number and genotype; thus, genotype had roughly the same effect at all times during training. B and D, Retention of the former platform site was impaired in control-fed 3×Tg-AD and hAPP(J20) mice [P<0.01 and P<0.001, Tukey's multiple comparisons test applied to a significant effect of genotype (P=0.01 and P<0.0001 respectively) in one-way ANOVA], but was not significantly different from that of non-Tg groups for rapamycin-fed 3×Tg-AD and hAPP(J20) animals. Data are mean±SEM.

FIG. 29A, 29B, 30C, 29D, 29E, 29F, 29G, 29H, 29I. Rapamycin decreases $A\beta_{42}$ levels and deposition. A and B, Representative Western blots from proteins extracted from brains of 3×Tg-AD and hAPP(J20) mice, respectively. C, D, and E, Quantitative analyses of APP, C99 and C83 (normalized to β-actin levels) show that rapamycin had no significant effect on APP processing in both transgenic lines. F and G, ELISA measurements indicate that rapamycin did not alter As40 levels in the brains of the 3×Tg-AD (f; P=0.89) or hAPP(J20) mice (G; P=0.29). In contrast, rapamycin significantly decreased soluble As42 levels in 3×Tg-AD and hAPP(J20) mice (P=0.02 and 0.04, respectively). H and I, Representative microphotographs depicting CA1 pyramidal neurons of the 3×Tg-AD mice stained with an anti-As42 antibody. Statistical evaluations were conducted using a two-tailed unpaired Student's t test.

FIG. 30A, 30B, 30C, 30D, 30E, 30F, 30G, 30H, 30I. Rapamycin administration significantly decreases tau pathology in the 3×Tg-AD mice. A and B, Representative microphotographs of CA1 pyramidal neurons stained with the anti-tau antibody AT270, which recognizes tau phosphorylated at Thr181, clearly indicate a decrease in AT270 immunoreactivity in mice treated with rapamycin. C and D, Higher magnification views of panels A and B respectively. E and F, Serial sections to those shown above were stained with the conformational-specific antitau antibody, MC1. While 8 month-old 3×Tg-AD mice begin to show MC1-positive inclusions in some hippocampal neurons (E), we were unable to detect any MC1-positive inclusions in brain of rapamycin-treated 3×Tg-AD mice. G, Representative Western blots of protein extracted from brains of 3×Tg-AD mice and probed with the phospho-specific anti-tau antibody, AT270 and with fA-actin as a loading control. H, Quantification analyses of the blots in panel G indicate that rapamycin significantly reduced the steady-state levels of phosphorylated tau at Thy181 (P=0.006). I, ELISA measurements show that the levels of soluble tau were significantly reduced in the brain of rapamycin-treated mice (P=0.01). No changes were detected for insoluble tau levels (P>0.05). Statistical evaluations were done using two-tailed unpaired Student's t-test and one-way ANOVA for AT270 immunoreactivity levels and for ELISA determinations respectively. Scale bar is 12.5 μm for panels A, B, E and F; 100 μm for panels C, D.

FIG. 31A, 31B, 31C, 31D, 31E, 31F. Rapamycin administration increases autophagy in brain of hAPP(J20) and 3×Tg-AD mice. A, Representative Western blots of proteins extracted from brains of 3×Tg-AD mice. B, E, Quantification analyses (data are normalized to s-actin) indicate that rapamycin significantly increased the steady-state levels of ATG7 (B; P=0.03) and the ATG5/ATG12 complex (C; P=0.04), indicating an increase in autophagy levels in rapamycin-treated mice. While no significant changes were observed in levels of LC3I (D; P>0.05), rapamycin significantly increased brain levels of LC3II (E; P=0.03), further indicating an increase in autophagy. E and F, Representative epifluorescent images of hippocampal CA1 in brain of control-fed (E) and rapamycin-fed (F) hAPP(J20) mice stained with an anti-LC3 antibody. A marked increase in LC3-specific immunoreactivity was observed in CA1 projections following rapamycin administration. Insets, z-stacks of confocal images from the same region. Representative 2D sections across the volumes are shown.

FIG. 35. Immunoblot assay of S6K1 in liver tumors from rapamycin (R)-treated and control (C) mice in cohort 3. These mice were on *rapa* chow for 20 months. P-Thr(389) p70 is the signal from phosphorylation-dependent antibody and p70 is the signal from the phosphorylation-independent antibody.

FIG. 36A, 36B. Rapamycin decreases phosphorylation of p70 kinase. A, Quantitative analysis of p-P70 immunoreactivity in blots of hippocampal lysates from control- or rapamycin-treated mice show that rapamycin decreases phosphorylation of p70 kinase consistent with inhibition of mTOR by rapamycin. b, Representative Western blot from proteins extracted from hippocampi of control- or rapamycin-treated hAPP(J20) mice (also known as PDAPP mice). Statistical evaluations were conducted using a two-tailed unpaired Student's t test.

DESCRIPTION OF ILLUSTRATIVE EMBODIMENTS

Figure 1:
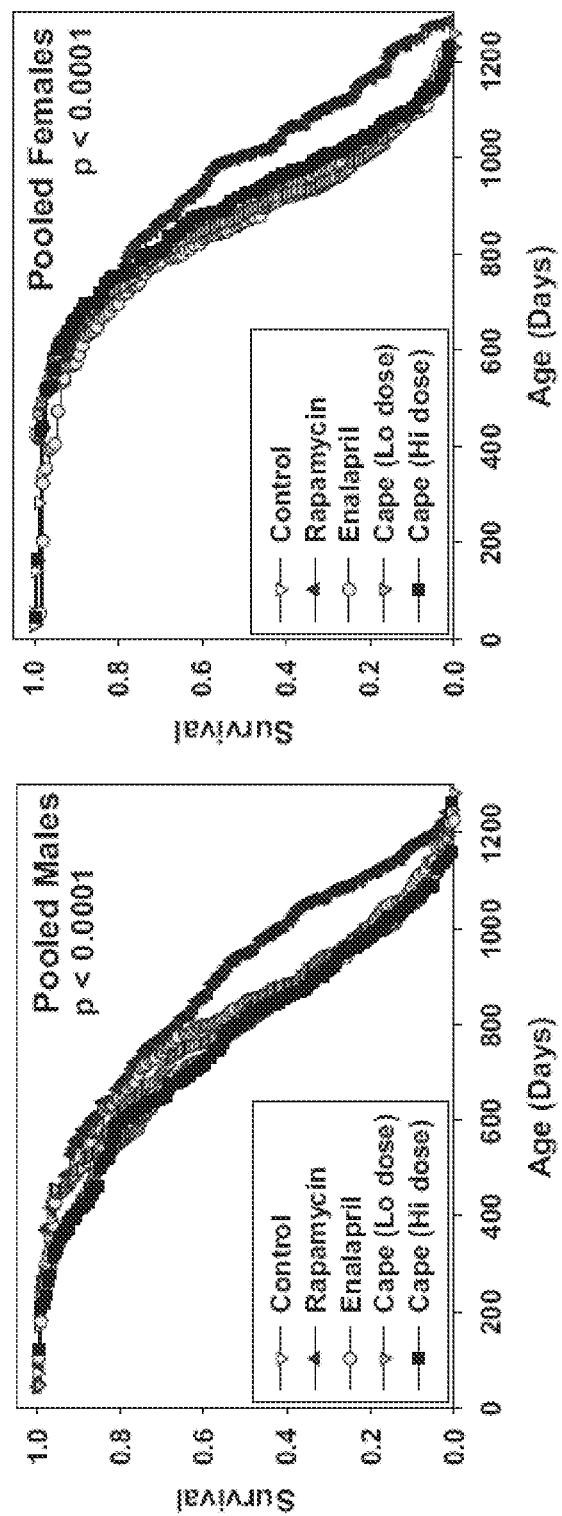
FIG. 1. Survival plots for male (left) and female (right) mice, comparing control mice to those fed enalapril, CAPE or rapamycin pooling across the three test sites. Enalapril and CAPE were added to the diet at 4 months of age, and rapamycin at 20 months. P-values were calculated by the log-rank test.

The present invention takes advantage of the recognition that microencapsulation of an inhibitor of mTOR improves the stability of the inhibitor, which thus improves the efficacy of the inhibitor in reducing cell aging, organism longevity, and age-related diseases of aging. For example, to improve stability of the drug in the diet, the inventors have developed a microencapsulation procedure which improves the fraction of rapamycin that survives food preparation by 3 to 4-fold. Mice consuming food with microencapsulated rapamycin has blood concentrations approximately 10 fold higher than those that ate non-encapsulated rapamycin-containing food. Microencapsulation of rapamycin made this test financially feasible, as the estimated costs for non-encapsulated rapamycin for the test was extremely high. After at least 50% of the mice had died, mice in the rapamycin group showed greater survival than controls (p<0001, males and p<0.0007, females). These data strongly support the concept that chronic inhibition of mTOR via any route of delivery of rapamycin or other known or unknown mTOR inhibitors will ameliorate age-related diseases such as cancer, metabolic syndromes and neurodegenerative diseases, thereby improving overall health an well being of mature adults.

A. mTOR INHIBITORS AND RAPAMYCIN

Any inhibitor of mTOR is contemplated for inclusion in the present microcapsules and methods. In particular embodiments, the inhibitor of mTOR is rapamycin or an analog of rapamycin. Rapamycin (also known as sirolimus and marketed under the trade name Rapamune®) is a known macrolide. The molecular formula of rapamycin is $C_{51}H_{79}NO_{13}$. The chemical name is (3S, 6R,7E,9R,10R,12R,14S,15E,17E,19E,21S,23S,26R,27R, 34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentria-contine-1,5,11,28,29 (4H,6H,31H)-pentone.

Rapamycin binds to a member of the FK binding protein (FKBP) family, FKBP 12. The rapamycin/FKBP 12 complex binds to the protein kinase mTOR to block the activity of signal transduction pathways. Because the mTOR signaling network includes multiple tumor suppressor genes, including PTEN, LKB1, TSC1, and TSC2, and multiple proto-oncogenes including PI3K, Akt, and eEF4E, mTOR signaling plays a central role in cell survival and proliferation. Binding of the rapamycin/FKBP complex to mTOR causes arrest of the cell cycle in the G1 phase (Janus et al., 2005).

mTOR inhibitors also include rapamycin analogs. Many rapamycin analogs are known in the art. Non-limiting examples of analogs of rapamycin include, but are not limited to, everolimus, tacrolimus, CCI-779, ABT-578, AP-23675, AP-23573, AP-23841, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, prerapamycin, temsirolimus, and 42-O-(2-hydroxy)ethyl rapamycin.

Other analogs of rapamycin include: rapamycin oximes (U.S. Pat. No. 5,446,048); rapamycin aminoesters (U.S. Pat. No. 5,130,307); rapamycin dialdehydes (U.S. Pat. No. 6,680,330); rapamycin 29-enols (U.S. Pat. No. 6,677,357); O-alkylated rapamycin derivatives (U.S. Pat. No. 6,440, 990); water soluble rapamycin esters (U.S. Pat. No. 5,955, 457); alkylated rapamycin derivatives (U.S. Pat. No. 5,922, 730); rapamycin amidino carbamates (U.S. Pat. No. 5,637, 590); biotin esters of rapamycin (U.S. Pat. No. 5,504,091); carbamates of rapamycin (U.S. Pat. No. 5,567,709); rapamycin hydroxyesters (U.S. Pat. No. 5,362,718); rapamycin 42-sulfonates and 42-(N-carbalkoxy)sulfamates (U.S. Pat. No. 5,346,893); rapamycin oxepane isomers (U.S. Pat. No. 5,344,833); imidazolidyl rapamycin derivatives (U.S. Pat. No. 5,310,903); rapamycin alkoxyesters (U.S. Pat. No. 5,233,036); rapamycin pyrazoles (U.S. Pat. No. 5,164,399); acyl derivatives of rapamycin (U.S. Pat. No. 4,316,885); reduction products of rapamycin (U.S. Pat. Nos. 5,102,876 and 5,138,051); rapamycin amide esters (U.S. Pat. No. 5,118,677); rapamycin fluorinated esters (U.S. Pat. No. 5,100,883); rapamycin acetals (U.S. Pat. No. 5,151,413); oxorapamycins (U.S. Pat. No. 6,399,625); and rapamycin silyl ethers (U.S. Pat. No. 5,120,842), each of which is specifically incorporated by reference.

Other analogs of rapamycin include those described in U.S. Pat. Nos. 7,560,457; 7,538,119; 7,476,678; 7,470,682; 7,455,853; 7,446,111; 7,445,916; 7,282,505; 7,279,562; 7,273,874; 7,268,144; 7,241,771; 7,220,755; 7,160,867; 6,329,386; U.S. Pat. RE37,421; U.S. Pat. Nos. 6,200,985; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; 5,023,262; all of which are incorporated herein by reference. Additional rapamycin analogs and derivatives can be found in the following U.S. Patent Application Pub. Nos., all of which are herein specifically incorporated by reference: 20080249123, 20080188511; 20080182867; 20080091008; 20080085880; 20080069797; 20070280992; 20070225313; 20070203172; 20070203171; 20070203170; 20070203169; 20070203168; 20070142423; 20060264453; and 20040010002.

Rapamycin or a rapamycin analog can be obtained from any source known to those of ordinary skill in the art. The source may be a commercial source, or natural source. Rapamycin or a rapamycin analog may be chemically synthesized using any technique known to those of ordinary skill in the art. Non-limiting examples of information concerning rapamycin synthesis can be found in Schwecke et al., 1995; Gregory et al., 2004; Gregory et al., 2006; Graziani, 2009.

B. PREPARATION OF MICROCAPSULES

The microcapsules of the present invention can be prepared using any method known to those of ordinary skill in the field. Any method known to those of ordinary skill in the art can be used to obtain the core. The core is then coated using any method known to those of ordinary skill in the art. In particular embodiments, the coating is an enteric coating. Some examples of coating are discussed below. In specific embodiments, applying an enteric coating involves use of a spinning disk atomizer, other methods may include pan coating, air-suspension coating, centrifugal extrusion, vibrational nozzle, spray-drying, interfacial polymerization, in situ polymerization, matrix polymerization.

Additional methods for preparing microcapsules are discussed in the following U.S. Patent Application Pub. Nos.: 20080022965, 20080193653, 20070138673; 20070082829; 20060234053, 20060121122, 20050113282, 20040121155, 20040074089, and 20020009473, and the following U.S. Pat. Nos. 7,576,903, 7,037,582, 6,936,644, 6,653,256, 6,592,916, 6,486,099, 4,460,722, each of which is herein specifically incorporated by reference.

C. CORES

The core as used herein refers to that portion of the microcapsule that includes the active agent, where the active agent is encased in a coating. Active agents have been discussed above and elsewhere in this specification.

The core may include any number of additional therapeutic agents, or any number of additional adjunct ingredients. For example, the core may further include at least one of an absorption enhanced, a binder, a hardness enhancing agent, optionally a disintegrant and another excipient. Examples of binders include povidone (PVP: polyvinyl pyrrolidone), low molecular weight HPC (hydroxypropyl cellulose), low molecular weight HPMC (hydroxypropyl methylcellulose), low molecular weight carboxy methyl cellulose, ethylcellulose, gelatin polyethylene oxide, acacia, dextrin, magnesium aluminum silicate, starch, and polymethacrylates. The core may include a stabilizer such as at least one of butyl hydroxyanisole, ascorbic acid and citric acid. The core may include a disintegrant selected from the group consisting of croscarmellose sodium, crospovidone (cross-linked polyvinyl pyrolidone) sodium carboxymethyl starch (sodium starch glycolate), cross-linked sodium carboxymethyl cellulose (Croscarmellose), pregelatinized starch (starch 1500), microcrystalline starch, water insoluble starch, calcium carboxymethyl cellulose, magnesium aluminum silicate and a combination thereof.

The core may include a filler such as filler such as monohydrate, microcrystalline cellulose, starch, lactitol, lactose, a suitable inorganic calcium salt, sucrose, or a combination thereof.

The core may include an antioxidant that is selected from the group consisting of 4,4 (2,3 dimethyl tetramethylene dipyrochatechol), Tocopherol-rich extract (natural vitamin E), .alpha.-tocopherol (synthetic Vitamin E), .beta.-tocopherol, .gamma.-tocopherol, .delta.-tocopherol, Butylhydroxinon, Butyl hydroxyanisole (BHA), Butyl hydroxytoluene (BHT), Propyl Gallate, Octyl gallate, Dodecyl Gallate, Tertiary butylhydroquinone (TBHQ), Fumaric acid, Malic acid, Ascorbic acid (Vitamin C), Sodium ascorbate, Calcium ascorbate, Potassium ascorbate, Ascorbyl palmitate, Ascorbyl stearate, Citric acid, Sodium lactate, Potassium lactate, Calcium lactate, Magnesium lactate, Anoxomer, Erythorbic acid, Sodium erythorbate, Erythorbin acid, Sodium erythorbin, Ethoxyquin, Glycine, Gum guaiac, Sodium citrates (monosodium citrate, disodium citrate, trisodium citrate), Potassium citrates (monopotassium citrate, tripotassium citrate), Lecithin, Polyphosphate, Tartaric acid, Sodium tartrates (monosodium tartrate, disodium tartrate), Potassium tartrates (monopotassium tartrate, dipotassium tartrate), Sodium potassium tartrate, Phosphoric acid, Sodium phosphates (monosodium phosphate, disodium phosphate, trisodium phosphate), Potassium phosphates (monopotassium phosphate, dipotassium phosphate, tripotassium phosphate), Calcium disodium ethylene diamine tetra-acetate (Calcium disodium EDTA), Lactic acid, Trihydroxy butyrophenone and Thiodipropionic acid.

The core may include a chelating agent such as antioxidants, dipotassium edentate, disodium edentate, edetate calcium disodium, edetic acid, fumaric acid, malic acid, maltol, sodium edentate, trisodium edetate.

The core may include a lubricant such as stearate salts, stearic acid, canola oil, glyceryl palmitostearate, hydrogenated vegetable oil, magnesium oxide, mineral oil, poloxamer, polyethylene glycole, polyvinyl alcohol, magnesium stearate, sodium benzoate, talc, sodium stearyl fumarate, compritol (glycerol behenate), and sodium lauryl sulfate (SLS) or a combination thereof. A preferred embodiment of the formulation according to the present invention preferably features a core which contains a hydrophilic, swellable, hydrogel-forming material, covered by a coating which includes a water insoluble polymer and hydrophilic water permeable agent, through which water enters the core. The swellable hydrogel-forming material in the core then swells and bursts the coating, after which the core more preferably disintegrates slowly or otherwise releases the active ingredient. Another optional but preferred embodiment relates to a release-controlling core with a slowly-erodible dry coating.

D. COATINGS

Many pharmaceutical dosage forms irritate the stomach due to their chemical properties or are degraded by stomach acid through the action of enzymes, thus becoming less effective. The coating may be an enteric coating, a coating that prevents release and absorption of active ingredients until they reach the intestine. "Enteric" refers to the small intestine, and therefore enteric coatings facilitate delivery of agents to the small intestine. Some enteric coatings facilitate delivery of agents to the colon. In some embodiments, the enteric coating is a EUDRAGIT (®) coating. Eudragit coatings include Eudragit L100-44 (for delivery to the duodenum), Eudragit L 30 D-55 (for delivery to the duodenum), Eudragit L 100 (for delivery to the jejunum), Eudragit S100 (for delivery to the ileum), and Eudragit FS 30D (for colon delivery). Other coatings include Eudragit RS, Eudragit RL, ethylcellulose, and polyvinyl acetate. Benefits include pH-dependent drug release, protection of active agents sensitive to gastric fluid, protection of gastric mucosa from active agents, increase in drug effectiveness, good storage stability, and GI and colon targeting.

Some examples of enteric coating components include cellulose acetate pthalate, methyl acrylate-methacrylic acid copolymers, cellulose acetate succinate, hydroxy propyl methyl cellulose phthalate, hydroxy propyl methyl cellulose acetate succinate, polyvinyl acetate phthalate, methyl methacrylate-methacrylic acid copolymers, sodium alginate, and stearic acid. The coating may include suitable hydrophilic gelling polymers including but not limited to cellulosic polymers, such as methylcellulose, carboxymethylcellulose, hydroxypropylcellulose, hydroxypropylmethylcellulose, hydroxyethylcellulose, and the like; vinyl polymers, such as polyvinylpyrrolidone, polyvinyl alcohol, and the like; acrylic polymers and copolymers, such as acrylic acid polymer, methacrylic acid copolymers, ethyl acrylate-methyl methacrylate copolymers, natural and synthetic gums, such as guar gum, arabic gum, xanthan gum, gelatin, collagen, proteins, polysaccharides, such as pectin, pectic acid, alginic acid, sodium alginate, polyaminoacids, polyalcohols, polyglycols; and the like; and mixtures thereof. Any other coating agent known to those of ordinary skill in the art is contemplated for inclusion in the coatings of the microcapsules set forth herein.

The coating may optionally comprises a plastisizer, such as dibutyl sebacate, polyethylene glycol and polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof. The coating may optionally include a gum. Non-limiting examples of gums include homopolysaccharides such as locust bean gum, galactans, mannans, vegetable gums such as alginates, gum karaya, pectin, agar, tragacanth, accacia, carrageenan, tragacanth, chitosan, agar, alginic acid, other polysaccharide gums (e.g., hydrocolloids), acacia catechu, salai guggal, indian bodellum, copaiba gum, asafetida, cambi gum, *Enterolobium cyclocarpum*, mastic gum, benzoin gum, sandarac, gambier gum, butea frondosa (Flame of Forest Gum), myrrh, konjak mannan, guar gum, welan gum, gellan gum, tara gum, locust bean gum, carageenan gum, glucomannan, galactan gum, sodium alginate, tragacanth, chitosan, xanthan gum, deacetylated xanthan gum, pectin, sodium polypectate, gluten, karaya gum, tamarind gum, ghatti gum, Accaroid/Yacca/Red gum, dammar gum, juniper gum, ester gum, ipil-ipil seed gum, gum talha (acacia seyal), and cultured plant cell gums including those of the plants of the genera: acacia, actinidia, aptenia, carbobrotus, chickorium, cucumis, glycine, hibiscus, hordeum, letuca, lycopersicon, malus, *medicago, mesembryanthemum, oryza, panicum, phalaris, phleum, poliathus, polycarbophil, sida, solanum, trifolium, trigonella, Afzelia africana* seed gum, *Treculia africana* gum, detarium gum, cassia gum, carob gum, *Prosopis africana* gum, *Colocassia esulenta* gum, *Hakea gibbosa* gum, khaya gum, scleroglucan, zea, mixtures of any of the foregoing, and the like.

E. APPLICATIONS

1. Definitions

"Treatment" and "treating" as used herein refer to administration or application of a therapeutic agent to a subject or performance of a procedure or modality on a subject for the purpose of obtaining a therapeutic benefit of a disease or health-related condition. For example, the microcapsules of the present invention may be administered to a subject for the purpose of treating a neurodegenerative disease in a subject. Treating as used herein refers to cure of all signs and symptoms of the disease, or reduction in the severity of signs or symptoms of a disease.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, administering microcapsules of the present invention to reduce the signs and symptoms of a neurodegenerative disease.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition. For example, administering the microcapsules of the present invention for the purpose of blocking the onset of a neurodegenerative disease in an elderly person.

2. Age-Related Diseases Associated with the TOR Pathway

The methods of the invention may be used to treat or prevent age-related diseases, conditions, or disorders. Non-limiting examples of age-related diseases, conditions, or disorders include insulin resistance (i.e., impaired glucose tolerance), benign prostatic hyperplasia, hearing loss, osteoporosis, age-related macular degeneration, neurodegenerative diseases, a skin disease, aging skin, or cancer. In one embodiment of the methods of the invention, the age-related disease, condition, or disorder is a skin disease. Examples of skin diseases for which the methods of the invention may be used include seborrheic keratosis, actinic keratosis, keloid, psoriasis, and Kaposi's sarcoma.

Non-limiting examples of neurodegenerative diseases include Alzheimer disease; epilepsy; Huntington's Disease; Parkinson's Disease; stroke; spinal cord injury; traumatic brain injury; Lewy body dementia; Pick's disease; Niewmann-Pick disease; amyloid angiopathy; cerebral amyloid angiopathy; systemic amyloidosis; hereditary cerebral hemorrhage with amyloidosis of the Dutch type; inclusion body myositis; mild cognitive impairment; Down's syndrome; and neuromuscular disorders including amyotrophic lateral sclerosis (ALS), multiple sclerosis, and muscular dystrophies including Duchenne dystrophy, Becker muscular dystrophy, Facioscapulohumeral (Landouzy-Dejerine) muscular dystrophy, and limb-girdle muscular dystrophy (LGMD). Also included is neurodegenerative disease due to stroke, head trauma, spinal injury, or other injuries to the brain, peripheral nervous, central nervous, or neuromuscular system.

In another embodiment of the methods of the invention, the age-related disease, condition, or disorder is an aging skin condition. Examples of aging skin conditions for which the methods of the invention may be used include age-related spots, pigment spots, wrinkles, photo-aged skin, or angiogenic spots. In still another embodiment of the methods of the invention, the inhibitor of TOR is administered to extend an individual's healthy life span.

The methods of the invention may be used to inhibit cellular or organismal events. In one embodiment of the invention, the cellular event being inhibited is cell aging. In another embodiment of the invention the cellular event being inhibited is cell hypertrophy. In still another embodiment of the invention, the cellular event being inhibited is organism aging.

Other examples of age-related diseases for which mTOR involvement has been demonstrated include the following: benign prostatic hyperplasia, benign prostatic hyperplasia (BPH), benign prostatic hypertrophy, benign enlargement of the prostrate (BEP), metabolic syndrome including insulin resistance and its complications, obesity (especially abdominal obesity), elevated blood pressure, thrombosis, hypertension and atherosclerosis, cardiac hypertrophy, and osteoporosis. With respect to specific neurodegenerative diseases, the mTOR pathway has been shown to be involved with Alzheimer's disease by increasing Tau protein synthesis (Li et al., 2005). In addition, a correlation between activated mTOR in blood lymphocytes and memory and cognitive decline has been established in individuals suffering from Alzheimer's disease (Paccalin et al., 2006).

With respect to cancer, non-limiting examples include breast cancer, lung cancer, prostate cancer, ovarian cancer, brain cancer, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia. Other specific examples of cancer include squamous cell carcinoma, basal cell carcinoma, adenoma, adenocarcinoma, linitis plastica, insulinoma, glucagonoma, gastrinoma, vipoma, cholangiocarcinoma, hepatocellular carcinoma, adenoid cystic carcinoma, carcinoid tumor, prolactinoma, oncocytoma, hurthle cell adenoma, renal cell carcinoma, endometrioid adenoma, cystadenoma, pseudomyxoma peritonei, Warthin's tumor, thymoma, thecoma, granulosa cell tumor, arrhenoblastoma, Sertoli-Leydig cell tumor, paraganglioma, pheochromocytoma, *glomus* tumor, melanoma, soft tissue sarcoma, desmoplastic small round cell tumor, fibroma, fibrosarcoma, myxoma, lipoma, liposarcoma, leiomyoma, leiomyosarcoma, myoma, myosarcoma, rhabdomyoma, rhabdomyosarcoma, pleomorphic adenoma, nephroblastoma, brenner tumor, synovial sarcoma, mesothelioma, dysgerminoma, germ cell tumors, embryonal carcinoma, yolk sac tumor, teratomas, dermoid cysts, choriocarcinoma, mesonephromas, hemangioma, angioma, hemangiosarcoma, angiosarcoma, hemangioendothelioma, hemangioendothelioma, Kaposi's sarcoma, hemangiopericytoma, lymphangioma, cystic lymphangioma, osteoma, osteosarcoma, osteochondroma, cartilaginous exostosis, chondroma, chondrosarcoma, giant cell tumors, Ewing's sarcoma, odontogenic tumors, cementoblastoma, ameloblastoma, craniopharyngioma gliomas mixed oligoastrocytomas, ependymoma, astrocytomas, glioblastomas, oligodendrogliomas, neuroepitheliomatous neoplasms, neuroblastoma, retinoblastoma, meningiomas, neurofibroma, neurofibromatosis, schwannoma, neurinoma, neuromas, granular cell tumors, alveolar soft part sarcomas, lymphomas, non-Hodgkin's lymphoma, lymphosarcoma, Hodgkin's disease, small lymphocytic lymphoma, lymphoplasmacytic lymphoma, mantle cell lymphoma, primary effusion lymphoma, mediastinal (thymic) large cell lymphoma, diffuse large B-cell lymphoma, intravascular large B-cell lymphoma, Burkitt lymphoma, splenic marginal zone lymphoma, follicular lymphoma, extranodal marginal zone B-cell lymphoma of mucosa-associated lymphoid tissue (MALT-lymphoma), nodal marginal zone B-cell lymphoma, mycosis fungoides, Sezary syndrome, peripheral T-cell lymphoma, angioimmunoblastic T-cell lymphoma, subcutaneous panniculitis-like T-cell lymphoma, anaplastic large cell lymphoma, hepatosplenic T-cell lymphoma, enteropathy type T-cell lymphoma, lymphomatoid papulosis, primary cutaneous anaplastic large cell lymphoma, extranodal NK/T cell lymphoma, blastic NK cell lymphoma, plasmacytoma, multiple myeloma, mastocytoma, mast cell sarcoma, mastocytosis, mast cell leukemia, langerhans cell histiocytosis, histiocytic sarcoma, langerhans cell sarcoma dendritic cell sarcoma, follicular dendritic cell sarcoma, Waldenstrom macroglobulinemia, lymphomatoid granulomatosis, acute leukemia, lymphocytic leukemia, acute lymphoblastic leukemia, acute lymphocytic leukemia, chronic lymphocytic leukemia, adult T-cell leukemia/lymphoma, plasma cell leukemia, T-cell large granular lymphocytic leukemia, B-cell prolymphocytic leukemia, T-cell prolymphocytic leukemia, pecursor B lymphoblastic leukemia, precursor T lymphoblastic leukemia, acute erythroid leukemia, lymphosarcoma cell leukemia, myeloid leukemia, myelogenous leukemia, acute myelogenous leukemia, chronic myelogenous leukemia, acute promyelocytic leukemia, acute promyelocytic leukemia, acute myelomonocytic leukemia, basophilic leukemia, eosinophilic leukemia, acute basophilic leukemia, acute myeloid leukemia, chronic myelogenous leukemia, monocytic leukemia, acute monoblastic and monocytic leukemia, acute megakaryoblastic leukemia, acute myeloid leukemia and myelodysplastic syndrome, chloroma or myeloid sarcoma, acute panmyelosis with myelofibrosis, hairy cell leukemia, juvenile myelomonocytic leukemia, aggressive NK cell leukemia, polycythemia vera, myeloproliferative disease, chronic idiopathic myelofibrosis, essential thrombocytemia, chronic neutrophilic leukemia, chronic eosinophilic leukemia/hypereosinophilic syndrome, post-transplant lymphoproliferative disorder, chronic myeloproliferative disease, myelodysplastic/myeloproliferative diseases, chronic myelomonocytic leukemia and myelodysplastic syndrome. In certain embodiments, the hyperproliferative lesion is a disease that can affect the mouth of a subject. Examples include leukoplakia, squamous cell hyperplastic lesions, premalignant epithelial lesions, intraepithelial neoplastic lesions, focal epithelial hyperplasia, and squamous carcinoma lesion.

The microcapsules of the present invention can be applied in the treatment of any disease for with use of an inhibitor of mTOR is contemplated. The following U.S. patents disclose various properties and uses of rapamycin and are herein incorporated by reference. U.S. Pat. No. 5,100,899 discloses inhibition of transplant rejection by rapamycin; U.S. Pat. No. 3,993,749 discloses rapamycin antifungal properties; U.S. Pat. No. 4,885,171 discloses antitumor activity of rapamycin against lymphatic leukemia, colon and mammary cancers, melanocarcinoma and ependymoblastoma; U.S. Pat. No. 5,206,018 discloses rapamycin treatment of malignant mammary and skin carcinomas, and central nervous system neoplasms; U.S. Pat. No. 4,401,653 discloses the use of rapamycin in combination with picibanil in the treatment of tumors; U.S. Pat. No. 5,078,999 discloses a method of treating systemic lupus erythematosus with rapamycin; U.S. Pat. No. 5,080,899 discloses a method of treating pulmonary inflammation with rapamycin that is useful in the symptomatic relief of diseases in which pulmonary inflammation is a component, i.e., asthma, chronic obstructive pulmonary disease, emphysema, bronchitis, and acute respiratory distress syndrome; U.S. Pat. No. 6,670,355 discloses the use of rapamycin in treating cardiovascular, cerebral vascular, or peripheral vascular disease; U.S. Pat. No. 5,561,138 discloses the use of rapamycin in treating immune related anemia; U.S. Pat. No. 5,288,711 discloses a method of preventing or treating hyperproliferative vascular disease including intimal smooth muscle cell hyperplasia, restenosis, and vascular occlusion with rapamycin; and U.S. Pat. No. 5,321,009 discloses the use of rapamycin in treating insulin dependent diabetes mellitus. In general, any disease which may be ameliorated, treated, cured or prevented by administration of rapamycin or a rapamycin derivative may be treated by administration of the microcapsules described herein. Non-limiting examples of such diseases include—organ or tissue transplant rejection, graft-versus-host disease, autoimmune disease and inflammatory conditions, arthritis (for example rheumatoid arthritis, arthritis chronica progrediente and arthritis deformans) and rheumatic diseases, autoimmune diseases, autoimmune hematological disorders, systemic lupus erythematosus, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including ulcerative colitis and Crohn's disease), endocrine opthalmopathy, Graves disease, sarcoidosis, multiple sclerosis, primary biliary cirrhosis, juvenile diabetes uveitis, keratoconjunctivitis sicca, vernal keratoconjunctivitis, interstitial lung fibrosis, psoriatic arthritis, glomerulonephritis, autosomal-dominant polycystic kidney disease, juvenile dermatomyositis, asthma, chronic obstructive pulmonary disease, emphysema, bronchitis, and acute respiratory distress syndrome, tumors, hyperproliferative skin disorders, fungal infections, dry eye, vascular disease, diabetes, and ocular disease (such as neovascularization of the eye due to age-related macular degeneration).

3. Preventive Therapies

Certain embodiments of the methods set forth herein pertain to methods of preventing a disease or health-related condition in a subject. Preventive strategies are of key importance in medicine today.

The quantity of pharmaceutical composition to be administered, according to dose, number of treatments and duration of treatments, depends on the subject to be treated, the state of the subject, the nature of the disease to be prevented and the protection desired. Precise amounts of the therapeutic composition also depend on the judgment of the practitioner and are peculiar to each individual. For example, the frequency of application of the composition can be once a day, twice a day, once a week, twice a week, or once a month. Duration of treatment may range from one month to one year or longer. Again, the precise preventive regimen will be highly dependent on the subject, the nature of the risk factor, and the judgment of the practitioner.

F. COMPOSITIONS

Certain of the methods set forth herein pertain to methods involving the administration of a composition comprising the microcapsules of the present invention.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present invention may comprise different types of carriers depending on whether it is to be administered in solid, liquid or aerosol form, and whether it need to be sterile for such routes of administration as injection.

The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations should meet sterility, pyrogenicity, general safety and purity standards as required by FDA Office of Biologics standards.

The formulation may vary depending upon the route of administration. For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure.

In certain embodiments, pharmaceutical composition includes at least about 0.1% by weight of the active compound. In other embodiments, the pharmaceutical composition includes about 2% to about 75% of the weight of the composition, or between about 25% to about 60% by weight of the composition, for example, and any range derivable therein. The pharmaceutical composition of the present invention may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The composition must be stable under the conditions of manufacture and storage, and preserved against the contaminating action of microorganisms, such as bacteria and fungi.

1. Routes of Administration

The microcapsules can be administered to the subject using any method known to those of ordinary skill in the art. For example, a pharmaceutically effective amount of the composition may be administered in a composition including an aqueous media that is administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitoneally, subcutaneously, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990). Solid compositions of microcapsules may be administered orally.

In particular embodiments, the composition is administered to a subject using a drug delivery device. Any drug delivery device is contemplated for use in delivering a pharmaceutically effective amount of the inhibitor of mTOR.

2. Dosage

A pharmaceutically effective amount of an inhibitor of mTOR is determined based on the intended goal. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

The amount of rapamycin or rapamycin analog to be administered will depend upon the disease to be treated, the length of duration desired and the bioavailability profile of the implant, and the site of administration. Generally, the effective amount will be within the discretion and wisdom of the patient's attending physician. Guidelines for administration include dose ranges of from about 0.01 mg to about 500 mg of rapamycin or rapamycin analog.

For example, a dose of the inhibitor of mTOR may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be intra-operative or post-operative.

3. Secondary Treatment

Certain embodiments of the present invention provide for the administration or application of one or more secondary forms of therapies. The type of therapy is dependent upon the type of disease that is being treated or prevented. The secondary form of therapy may be administration of one or more secondary pharmacological agents that can be applied in the treatment or prevention of a disease associated with aging, including any of the diseases set forth above.

If the secondary therapy is a pharmacological agent, it may be administered prior to, concurrently, or following administration of the inhibitor of mTOR.

The interval between the inhibitor of mTOR and the secondary therapy may be any interval as determined by those of ordinary skill in the art. For example, the interval may be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations. In some embodiments, the timing of administration of a secondary therapeutic agent is determined based on the response of the subject to the inhibitor of mTOR.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Lifespan Extension by Rapamycin Fed to Genetically Heterogeneous Mice from 20 Months of Age Methods Mouse Production, Maintenance, and Estimation of Lifespan.

Mice were produced at each of the three test sites by mating CB6F1 females with C3D2F1 males to produce a genetically heterogeneous population. Details of the methods used for health monitoring were provided previously (Miller et al., 2007); in brief, each of the three colonies was evaluated four times each year for infectious agents, including pinworm. All such tests were negative throughout the entire study period. Each test site enrolled approximately equal numbers of 19-21 day-old weanlings each month over a six month period, housing 3 males or 4 females/cage. Each site used diets that the manufacturer claimed were based on the NIH-31 standard for breeding cages and the period between weaning and the initiation of experimental diets, as follows: For breeding cages, UM used Purina 5008, UT used Teklad 7912, and TJL used Purina 5K52. For weanlings prior to 4 months of age, UM used Purina 5008, UT used Teklad 7912, and TJL used Purina 5LG6. Starting when 4 months old, mice in the Control, Enalapril, and CAPE groups received Purina 5LG6 at all three sites, without additives (control group) or with the test agent. Mice in the Rapa group remained on the weanling diet until they began to receive rapamycin, in Purina 5LG6, at 600 days of age. Separate cohorts of control and rapamycin-treated mice were established in the same way one year later, again at each test site, but with rapamycin initiated at 270 days rather than at 600 days of age. Additional husbandry details, including accounts of tests for T cell subset distribution and activity administered to a subset of each group, are provided elsewhere (Nadon et al., 2008). The principal endpoint was age at death (for mice found dead at daily inspections) or age at euthanasia (for mice deemed unlikely to survive for more than an additional 48 h).

Removal of Mice from the Longevity Population.

The Cohort 2005 study population, distributed almost equally among the three test sites, consisted initially of 1960 mice, of which 674 were assigned to the control group and 317 to 328 to each of the four treatment groups. Of these, 51 mice were removed from the study because of fighting (31 mice), accidental death (such as chip implantation or cage flooding; 13 mice), or because of technical error (error in gender assignment or diet selection; 7 mice). For survival analyses, mice were treated as alive at the date of their removal from the protocol, and lost to follow-up thereafter. These censored mice were not included in calculations of median longevity.

Estimation of Age at Death (Lifespan).

Mice were examined at least daily for signs of ill health, and were euthanized for humane reasons if they were so severely moribund that they were considered, by an experienced technician, unlikely to survive for more than an additional 48 hrs. A mouse was considered severely moribund if it exhibited more than one of the following clinical signs: (a) inability to eat or to drink; (b) severe lethargy, as indicated by a lack of response such as a reluctance to move when gently prodded with a forceps; (c) severe balance or gait disturbance; (d) rapid weight loss over a period of one week or more; or (e) a severely ulcerated or bleeding tumor. The age at which a moribund mouse was euthanized was taken as the best available estimate of its natural lifespan. Mice found dead were also noted at each daily inspection. Bodies were saved for later analysis, to be reported elsewhere.

Control and Experimental Diets.

TestDiet, Inc. (Richmond, Ind.) prepared batches of Purina 5LG6 food containing each of the test substances, as well as control diet batches, at intervals of approximately 120 days, and shipped each batch of food at the same time to each of the three test sites. Enalapril was purchased from Sigma (catalogue E6888-5G) and used at 120 mg per kg food; on the assumption that the average mouse weighs 30 gm and consumes 5 gm of food/day, this dose supplies 20 mg enalapril per kg body weight/day. CAPE, i.e. caffeic acid phenethyl ester, was purchased from Cayman (Ann Arbor, Mich.; Catalogue 70750), and used at either of two doses: the high dose was 300 mg/kg food (50 mg/kg body weight/day), and the low dose was 30 mg/kg food (5 mg/kg body weight/day). Enalapril was tested because in aged humans and in rodent models of hypertension, obesity, diabetes, and congestive heart failure, it has been reported to improve many of these conditions. CAPE was tested because this agent has been reported to possess antioxidant, anti-inflammatory, and immunomodulatory capabilities, as well as specific toxicity to transformed and tumor cells. Lifespans of mice given enalapril or CAPE are compared with controls and those given rapamycin in FIG. 1. Rapamycin was purchased from LC Labs (Woburn, Mass.). The rapamycin was microencapsulated by Southwest Research Institute (San Antonio, Tex.), using a spinning disk atomization coating process with the enteric coating material Eudragit S100 ((Röhm Pharma, Germany). This methacrylate polymer is stable at pH levels below 7 and thus protects the rapamycin from the acidic conditions of the stomach; the protective coating dissolves in the small intestine, permitting absorption of the active agent. This thermoplastic coating material increased the fraction of rapamycin that survived the food preparation process by 3 to 4-fold. Because the coating material is water soluble only in non-acidic conditions, the encapsulated rapamycin is released in the small intestine rather than in the stomach. A pilot study showed that encapsulated rapamycin led to blood concentrations approximately 10-fold higher than achieved by equivalent doses of non-encapsulated rapamycin. The encapsulated rapamycin was administered at 14 mg/kg food (2.24 mg of rapamycin per kg body weight/day). Encapsulated rapamycin was then incorporated into 5LG6 mouse chow and distributed to all three test sites.

Measurement of Rapamycin.

Rapamycin was obtained from LC Laboratories (Woburn, Mass.). 32-desmethoxyrapamycin (32-RPM) was obtained from Sigma Chemical Company (St. Louis, Mo.). HPLC grade methanol and acetonitrile were purchased from Fisher (Fair Lawn, N.J.). All other reagents were purchased from Sigma Chemical Company (St. Louis, Mo.). Milli-Q water was used for preparation of all solutions. The HPLC system consisted of a Waters 510 HPLC pump, Waters 717 autosampler, Waters 2487 UV detector, and Waters Empower chromatographic software (Waters, Milford, Mass.). The HPLC analytical column was a Grace Alltima C18 (4.6×150 mm, 5 micron) purchased from Alltech (Deerfield, Ill.). The mobile phase was 64% (v/v) acetonitrile, and 36% water. The flow rate of the mobile phase was 1.5 ml/min and the wavelength of absorbance was 278 nm. The temperature of the HPLC analytical column was maintained at 70° C. during the chromatographic runs using an Eppendorf CH-30 column heater. Rapamycin and 32-RPM powder were dissolved in methanol at a concentration of 1 mg/ml and stored in aliquots at −80° C. A working stock solution was prepared each day from the methanol stock solutions at a concentration of 1 µg/ml and used to spike the calibrators. Calibrator samples were prepared daily by spiking either whole blood or mouse food with stock solutions to achieve final concentrations of 0, 4, 8, 12, 24, 100, and 200 ng/ml.

Rapamycin was quantified in mouse blood using HPLC with UV detection. Briefly, 0.5 mL of calibrators and unknown samples were mixed with 75 µL of 1.0 µg/mL 32-desmethoxy rapamycin (internal standard), 1.0 mL ZnSO4 (50 g/L) and 1.0 mL of acetone. The samples were vortexed vigorously for 20 sec, then centrifuged at 2600 g at 23° C. temperature for 5 min (subsequent centrifugations were performed under the same conditions). Supernatants were transferred to clean test tubes, then 200 µL of 100 mM NaOH was added, followed by vortexing. Then, 2 mL of 1-chlorobutane was added and the samples were capped, vortexed (1 min), and centrifuged. The supernatants were transferred to 10 mL glass tubes and dried to residue under a stream of nitrogen at ambient temperature. The dried extracts were dissolved in 750 µL of mobile phase and then 2 mL of hexane was added to each tube. The tubes were capped, vortexed for 30 sec, and centrifuged for 2 min. The hexane layers were removed and discarded. The remaining extracts were dried under nitrogen and reconstituted in 250 µL of mobile phase, and then 200 µL of the final extracts were injected into the HPLC. The ratio of the peak area of rapamycin to that of the internal standard (response ratio) for each unknown sample was compared against a linear regression of calibrator response ratios to quantify rapamycin. The concentration of rapamycin was expressed as ng/mL whole blood.

Rapamycin content of mouse chow was verified using HPLC with UV detection. Briefly, 100 mg of chow for spiked calibrators and unknown samples were crushed with a mortar and pestle, then vortexed vigorously with 20 µL of 100 µg/mL 32-RPM (internal standard) and 0.5 mL methanol. The samples were then mechanically shaken for 10 min. Next, 0.5 mL of Millipore water was added and the samples were vortexed vigorously for 20 sec. The samples were centrifuged for 10 min and then 40 µL were injected into the HPLC. The ratio of the peak area of rapamycin to that of the internal standard (response ratio) was compared against a linear regression of calibrator response ratios at rapamycin concentrations of 0, 2, 4, 8, 10, and 20 ng/mg of food to quantify rapamycin. The concentration of rapamycin in food was expressed as ng/mg food (parts per million).

Rapamycin Effectiveness.

To assay for the status of an mTORC1 downstream effector, phosphorylation of ribosomal protein S6 (Ser240/244), a substrate of S6 kinase 1, was measured in visceral adipose tissue lysates in mice fed an encapsulated rapamycin diet for 420 days or a control diet with empty microcapsules. Tissues were dissected and snap frozen in liquid nitrogen for storage at −80° C., ground into powder under liquid nitrogen and dissolved in 10 volumes of buffer (50 mM Tris-HCl (pH 7.5), 120 mM NaCl, 1% NP-40, 1 mM EDTA, 50 mM NaF, 40 mM 2-glycerophosphate, 0.1 mM Na orthovanadate (pH 10), 1 mM benzamidine, and 1× Complete protease inhibitor cocktail (Roche). After sonication and microcentrifugation, lysates were quantified, 30. 40 µg of soluble protein from each extract was loaded on a 4-12% gradient PAGE and electrophoresed overnight at 5V. Gels were then transferred to nitrocellulose membranes (dry procedure), blocked and incubated with the primary antibodies [S6 Ribosomal Protein (5G10) Rabbit mAb cat. #2217; Phospho-S6 Ribosomal Protein (Ser235/236) Antibody cat. #2215; and Cat. #4968 Pan-Actin Antibody; Cell Signaling Technologies, Danvers Mass.], followed by secondary antibody [Anti-rabbit IgG, (H+L), Peroxidase Conjugated Antibody, cat. #31460 Pierce, Rockford Ill.] for detection by chemiluminescence. Signal intensities for each immunoblot were captured using a Kodak Image Station, which were analysed using Kodak 1D image analysis software.

Results

Figure 2:
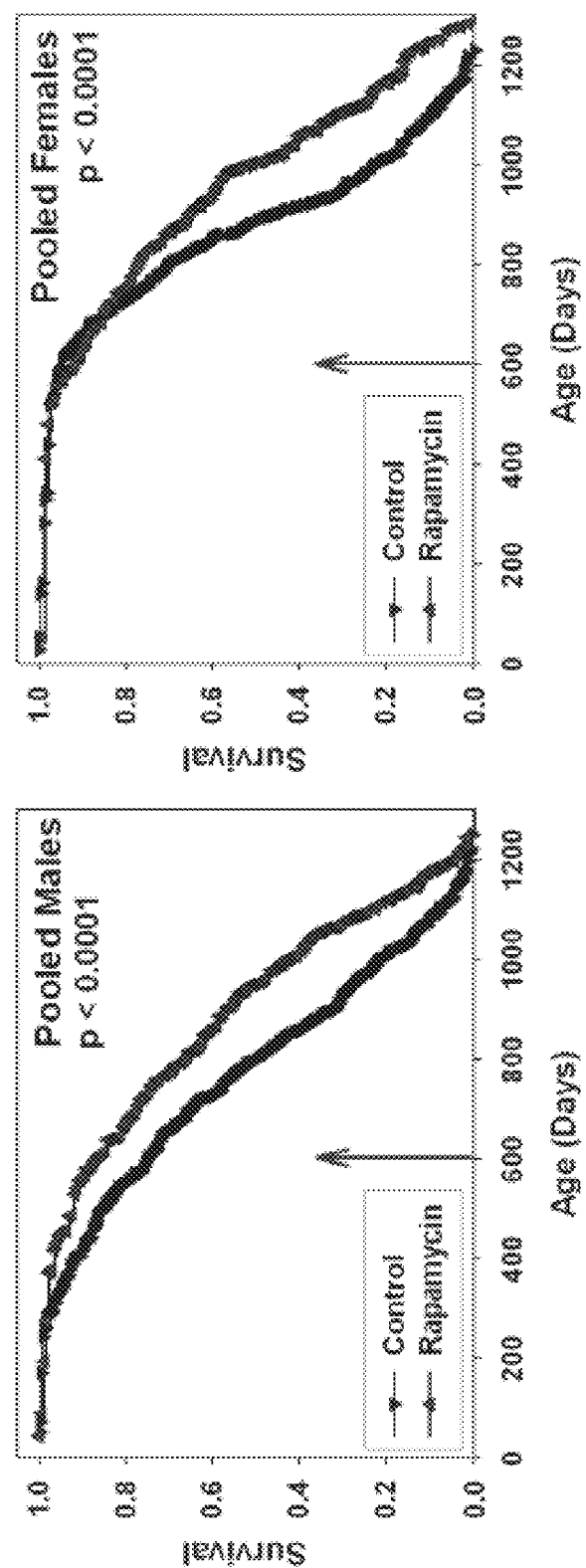
FIG. 2. Survival plots for male and female mice, comparing control mice to those fed rapamycin in the diet starting at 600 days of age, pooling across the three test sites. P values were calculated by the log-rank test. Four percent of the control mice and three percent of rapamycin-assigned mice were removed from the experiment for technical reasons. Only five animals (three controls, two rapamycin) were removed after the start of rapamycin treatment at 600 days. Thus, there was no significant differences between groups in censoring.

In male and female mice at each of three collaborating research sites, median and maximum life-span of mice were extended by feeding encapsulated rapamycin starting at 600 days of age (FIG. 2). The data set was analyzed with 2% (38 of 1,901) of mice still alive. For data pooled across sites, a log-rank test rejected the null hypothesis that treatment and control groups did not differ (P<0.0001); mice fed rapamycin were longer lived than controls (P<0.0001) in both males and females. Expressed as mean lifespan, the effect sizes were 9% for males and 13% for females in the pooled data set. Expressed as life expectancy at 600 days (the age of first exposure to rapamycin), the effect sizes were 28% for males and 38% for females. Mice treated with other agents (enalapril and CAPE (caffeic acid phenethyl ester)) evaluated in parallel did not differ from controls at the doses used (FIG. 1).

Figure 3:
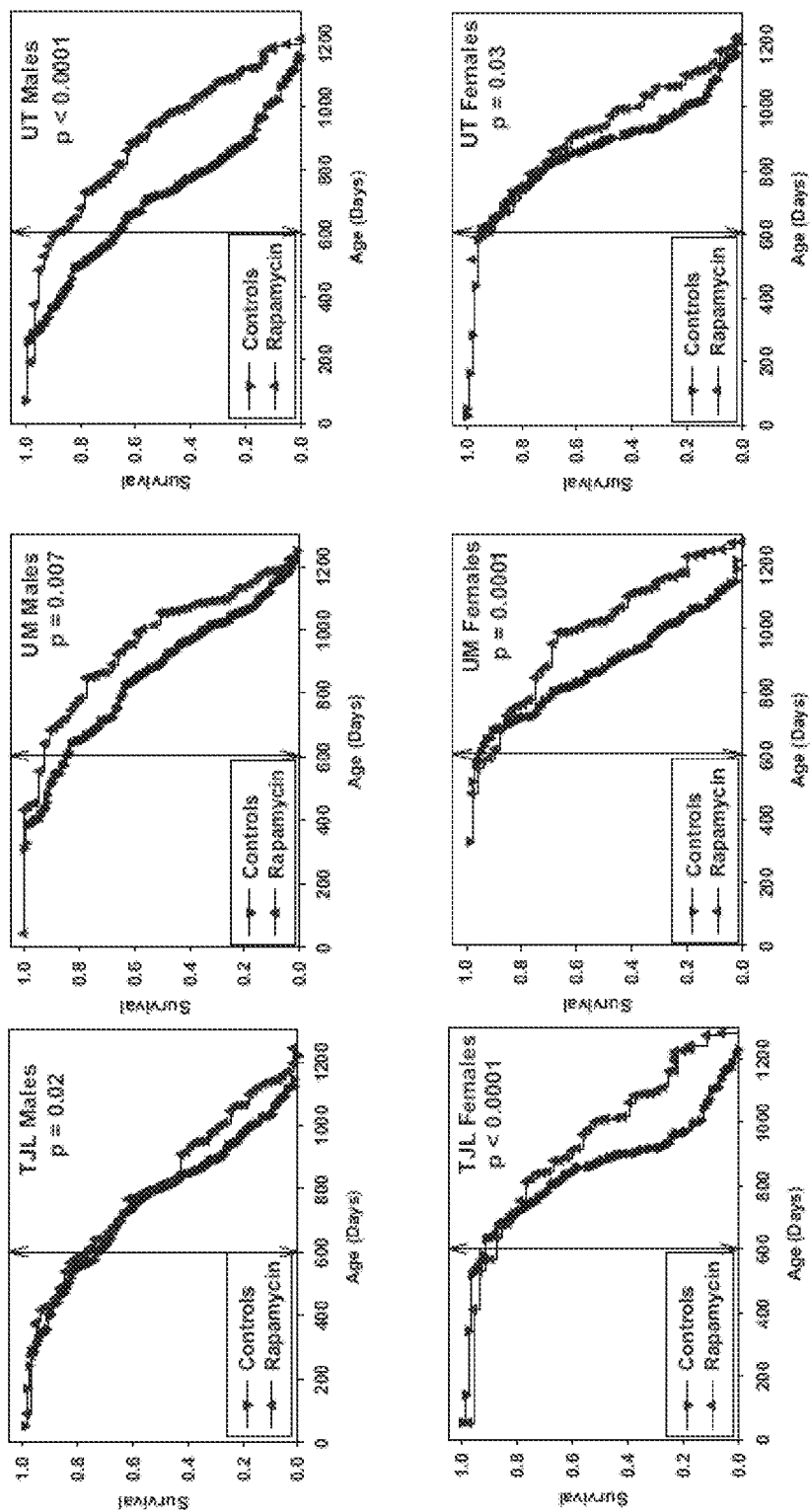
FIG. 3. Survival of control and rapamycin-treated mice for males and females for each of the three test sites separately. P values represent results of log-rank calculations. Vertical lines at age 600 days indicate the age at which the mice were first exposed to rapamycin.

Rapamycin-fed and control mice were then compared separately for each combination of site and gender. Rapamycin had a consistent benefit, compared with controls, with P values ranging from 0.03 to 0.0001 (FIG. 3). Female mice at all three sites had improved survival after rapamycin feeding (FIG. 3). Mean lifespan increases for females were 15%, 16% and 7% (TJL, UM and UT, respectively), and life expectancy at 600 days increased by 45%, 48% and 22% for females at the three sites. Median lifespan estimates of control females were consistent across sites (881-895 days), and were similar to values noted in Cohort 2004, which ranged from 858 to 909 days (Miller et al., 2007). Thus, the improvement in survival seen in the rapamycin-fed females is not an artifact of low survival for the control females. Male mice at all three sites also had improved survival after rapamycin feeding (FIG. 3). Mean lifespan increases for males were 5%, 8% and 15% (TJL, UM and UT, respectively), and male life expectancy at 600 days increased by 16%, 23% and 52%. Interpretation is complicated by differences among sites in survival of control males, and because mice assigned to the rapamycin-fed group at UT and perhaps at UM had lower mortality before 600 days than controls. Control mice at UT and UM differed from those fed rapamycin not only in exposure to rapamycin from 600 days of age but also in specific formulation of the mouse chows (all based on the NIH-31 standard) used between weaning and 600 days. Thus, one cannot rule out the possibility that improved survival among males in the rapamycin group, at UT and at UM, might reflect differences in nutritional or health status between control and rapamycin groups before 600 days, rather than solely the effects of rapamycin. Notably, the significant benefits of rapamycin on male (and female) survival at TJL could not have been affected by diet before drug administration, because at TJL both control and rapamycin-fed mice received the same chow (Purina 5LG6) throughout this period. Maximum lifespan was increased by rapamycin feeding. Table 1 shows the ages at the 90th percentile for control and rapamycin treated mice, along with the 95% upper confidence bound for the controls.

TABLE 1

The effect of rapamycin on maximum lifespan

| Comparison | Sites | Age in days at 90th percentile for controls (upper confidence limit)* | Age in days at 90th percentile for rapamycin-treated mice | Percentage increase |
|---|---|---|---|---|
| Females | | | | |
| Rapamycin versus controls | All sites | 1,094 (1,136) | 1,245 | 14 |
| Rapamycin versus controls | TJL | 1,100 (1,165) | 1,282 | 17 |
| Rapamycin versus controls | UM | 1,094 (1,149) | 1,250 | 14 |
| Rapamycin versus controls | UT | 1,089 (1,159) | 1,179 | 8 |
| Males | | | | |
| Rapamycin versus controls | All sites | 1,078 (1,111) | 1,179 | 9 |
| Rapamycin versus controls | TJL | 1,035 (1,091) | 1,142 | 10 |
| Rapamycin versus controls | UM | 1,141 (1,177) | 1,188 | 4 |
| Rapamycin versus controls | UT | 1,020 (1,101) | 1,179 | 16 |
| Rapamycin versus controls | All sites | 1,078 (1,111) | 1,179 | 9 |

*The upper limit of the 95% confidence interval for control mice is indicated in parentheses. For example, in the top row, for females pooled across sites, the 95% confidence interval for controls goes up to 1,136 days, and the estimate for 90th percentile survival for the rapamycin-treated mice is 1,245 days. This gives good evidence that the 90th percentile survival for rapamycin-treated mice (1,245) is substantially above that for controls (1,094).

For each site and sex, the 90th percentile age for rapamycin-treated mice is higher than the upper limit for the corresponding control group, showing that rapamycin increases the age for $90^{th}$ percentile survival.

To determine whether increases in maximal lifespan due to rapamycin feeding are statistically significant, the proportion of living mice in each group after 90% had died in the joint life table (Wang et al., 2004) were compared (Table 2).

TABLE 2

Details of calculation for comparison of surviving proportion of mice at the $90^{th}$ percentile age.

| Site | Sex | Age for $90^{th}$ percentile | Group | Number alive | Number dead | Total | % Live | Youngest live mouse | p-value |
|---|---|---|---|---|---|---|---|---|---|
| TJL | F | 1167 | Controls | 4 | 91 | 95 | 4.2% | 1192 | P = 0.0006 |
|  |  |  | Rapa | 11 | 37 | 48 | 22.9% | 1192 |  |
| UM | F | 1162 | Controls | 2 | 93 | 95 | 2.1% | 1187 | P = 0.0001 |
|  |  |  | Rapa | 13 | 35 | 48 | 27.1% | 1147 |  |
| UT | F | 1123 | Controls | 8 | 91 | 99 | 8.1% | 1180 | P = 0.22 |
|  |  |  | Rapa | 7 | 41 | 48 | 14.6% | 1189 |  |
| Pooled | F |  | Controls | 14 | 275 | 289 | 4.8% |  | P < 0.0001 |
|  |  |  | Rapa | 31 | 113 | 144 | 21.5% |  |  |
| TJL | M | 1088 | Controls | 8 | 118 | 126 | 6.3% | 1146 | P = 0.008 |
|  |  |  | Rapa | 11 | 46 | 57 | 19.3% | 1243 |  |
| UM | M | 1154 | Controls | 9 | 103 | 112 | 8.0% | 1161 | P = 0.07 |
|  |  |  | Rapa | 9 | 42 | 51 | 17.6% | 1228 |  |
| UT | M | 1112 | Controls | 4 | 115 | 119 | 3.4% | 1157 | P = 0.0001 |
|  |  |  | Rapa | 14 | 48 | 60 | 23.3% | 1156 |  |
| Pooled | M |  | Controls | 21 | 336 | 357 | 5.9% |  | P < 0.0001 |
|  |  |  | Rapa | 34 | 134 | 168 | 20.2% |  |  |

The table lists, for each combination of site, gender, and treatment group, the number of mice that were alive (and number dead) at the age (column 3) at which 90% of the joint distribution (control plus rapamycin for the site/gender combination) had died. For example, for females at TJL, 4.2% of the controls (4/95) and 22.9% of the rapamycin-treated mice (11/48) were still alive at the age of 1167 days. At the time of analysis (Feb. 1, 2009), there were no live control mice at ages below the 90th percentile age in any of the groups. The was one live female, at UM, at an age below the $90^{th}$ percentile threshold, but this mouse was in the rapamycin group, and its age at death would therefore not have a major effect on the statistics and pvalues listed in the table.

Summing across the three sites, 4.8% of the female control mice were alive at these ages, compared with 21.5% of the rapamycin-treated females (P<0.0001). For males, the corresponding values were 5.9% of controls and 20.2% of rapamycin-treated mice (P<0.0001). The site-specific calculations documented a significant effect on females at both TJL (P<0.0006) and UM (P<0.0001); for males, a significant effect at both TJL (P50.008) and UT (P50.0001) was noted, with a marginal effect at UM (P50.07). Rapamycin feeding initiated at 600 days of age thus leads to a significant increase in maximal lifespan.

To test if the spectrum of lesions was altered by dietary rapamycin, complete necropsies were conducted on 31 control and 40 rapamycin fed mice that were either found dead or killed when moribund (Table 3). Although rapamycin postpones death, it did not change the distribution of presumptive causes of death.

TABLE 3

Lesions in rapamycin-treated mice and in controls at the time of death.

| Cause of Death | Controls | Rapamycin |
|---|---|---|
| Abscesses | 1 | 1 |
| Adrenal tumor | 1 |  |
| Carcinoma (GI) | 1 |  |
| Carcinoma (renal) | 1 |  |
| Cardiac degeneration |  | 1 |
| Cardiomyopathy |  | 1 |
| Fibrosarcoma |  | 2 |
| Gastric ulcer | 1 |  |
| Heart failure | 2 | 1 |
| Heart fibrosis |  |  |
| Hemangiosarcoma | 3 | 5 |
| Hepatocarcinoma | 3 | 3 |
| Leiomyosarcoma |  | 1 |
| Lymphoma | 10 | 15 |
| Mammary adenocarcinoma |  | 1 |
| Myocardial infarct |  | 1 |
| Pleuritis | 1 |  |
| Prostatitis | 2 |  |
| Pulmonary tumor | 4 | 7 |
| Septicemia | 1 |  |
| Diagnosable cases | 31 | 40 |
| Autolysis | 17 | 12 |
| Unknown | 2 | 1 |
| Grand Total | 50 | 53 |

The mean age at death was 977 for controls (N = 31) and 1005 days for rapamycin-treated (N = 40) mice, among those animals for which a presumptive cause of death could be determined. Cause of death was inferred, where possible, based on gross evaluation, followed by histopathologic examination of a standard set of tissues from each mouse by an experienced veterinary pathologist. Tumors were deemed the cause of death based on tumor type, size, number, and distribution. Cause of death for mice with inflammatory or degenerative lesions was based on the location and severity of the lesions and the likelihood that such lesions were severe enough to cause morbidity and mortality. Many animals had small, localized tumors and various degenerative lesions, which were deemed unlikely to have contributed to their death. Autolysis precluded diagnosis in 29 cases, and the cause of death could not be determined in three other cases as indicated.

Figure 4A:
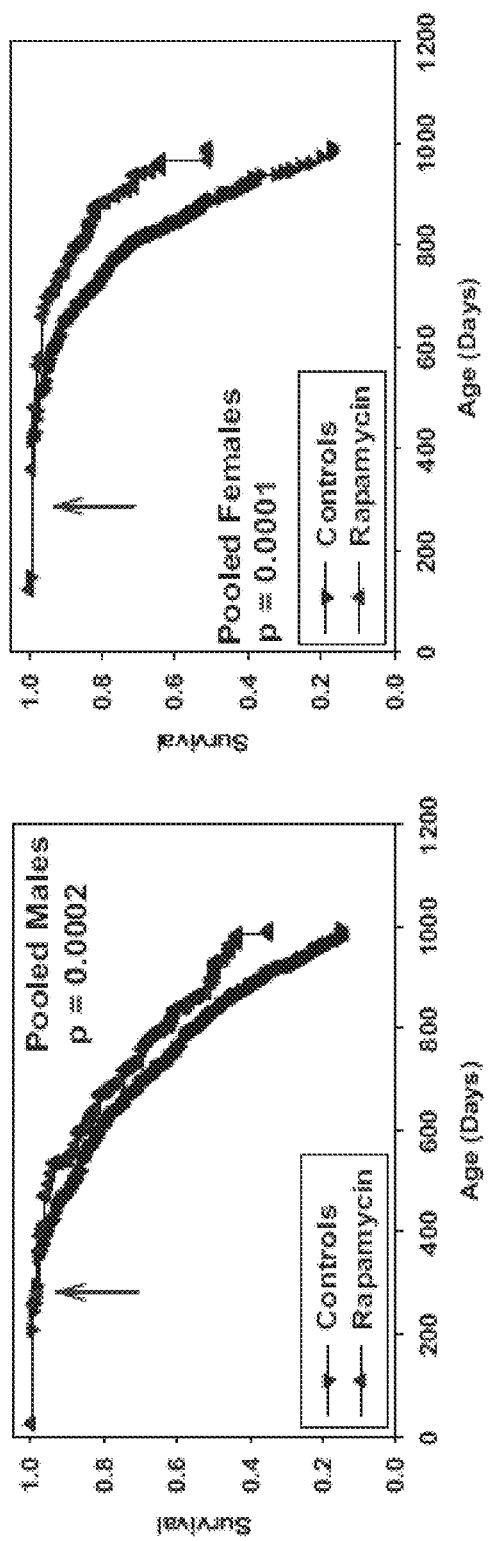
FIG. 4A, 4B, 4C. Characterization of mice receiving rapamycin from 270 days of age. A, Survival plots for male and female mice, comparing control mice to rapamycin-treated mice of a separate (Cohort 2006) population, in which mice were treated with rapamycin from 270 days of age. Because at the time of the interim analysis all live mice were between 800 and 995 days of age, only limited information about the shape of the survival curve at ages above 900 days, and the apparent change in slope at the oldest ages (>990 days) reflects this experimental uncertainty. P values were calculated by the log-rank test. B, Effects of dietary rapamycin on an mTOR effector in the visceral fat pads from 750-day-old to 880-day-old male and female mice. Ribosomal subunit protein S6 (rpS6) and its phosphorylation status (P-rpS6, double arrow) were immunoassayed in tissue lysates prepared from mice consuming microencapsulated rapamycin-containing or control diets. Antibodies used are shown to the left. The ratio of intensity values for P-rpS6/rpS6 is shown in the graphs for female and male mice. Pan-actin was also immunoassayed in the blots to provide an indication of protein loading for each lane. C, Whole blood rapamycin content in 750-day-old to 880-day-old male and female mice. In B and C, error bars show standard errors of the mean.

A separate group of mice was used to evaluate the effects of encapsulated rapamycin initiated at 270 days of age (FIG. 4A). At the time of analysis, 51% of the females and 68% of the males had died, and a stratified log-rank test showed significantly lower mortality risk in the rapamycin-treated mice compared to controls, pooling across the three test sites (P=0.0002 for males and P<0.0001 for females). When each site was evaluated separately, the beneficial effect of rapamycin for females was significant at each site (P<0.005); for males, the effect was significant (P<0.025) at UM and UT, but not at TJL. Rapamycin seems to reduce mid-life mortality risk when started at 270 days of age, but additional data are needed to provide an accurate estimate of effect size, and to evaluate effects on maximal longevity.

Figures 4B, 4C:
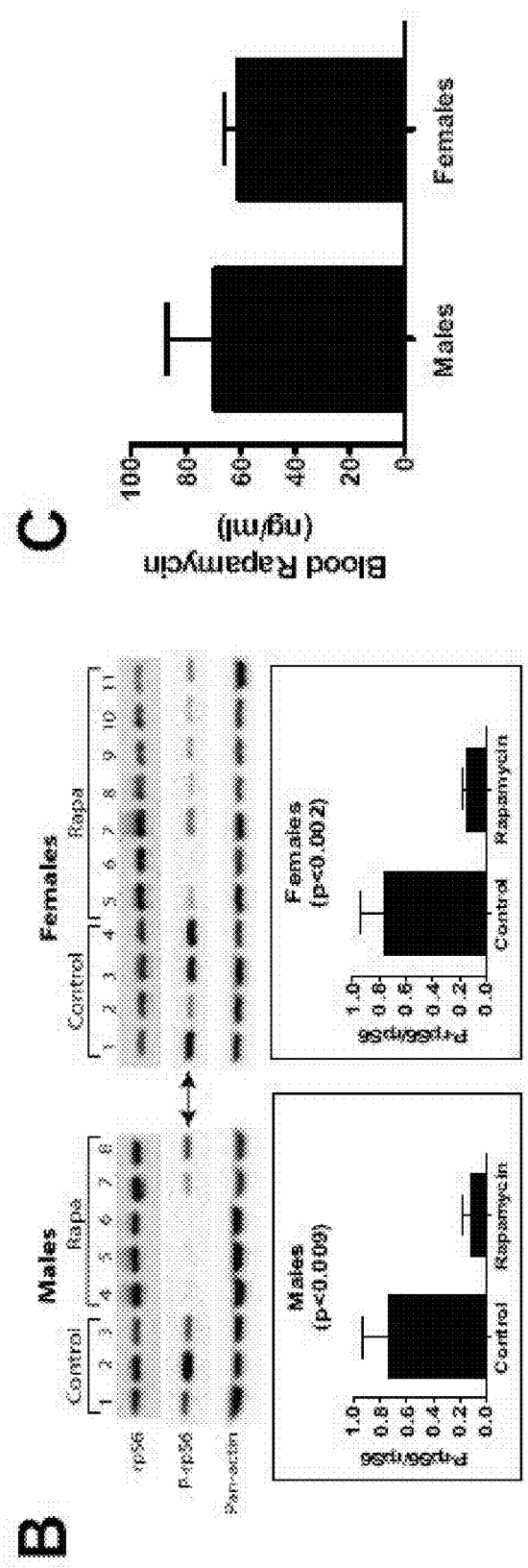

To document biochemical effects of rapamycin at the dose used for the lifespan studies, the phosphorylation status of ribosomal protein subunit S6 (rpS6)—a target substrate of S6 kinase 1 in the mTOR signalling pathway20—was evaluated in visceral white adipose tissue (a sensitive indicator of mTOR inhibition by rapamycin treatment in vivo). FIG. 4B shows that rapamycin feeding reduced the levels of phosphorylated rpS6 4-5-fold when fed from 270 to about 800 days of age. Blood levels of rapamycin in the treated mice were equivalent in males and females, between 60 and 70 ng/ml.

Initial evidence that reduced TOR function can extend longevity came primarily from studies in yeast (Kaeberlein et al., 2005; Powers et al., 2006) and invertebrates (Jia et al., 2005; Kapahi et al., 2004; Vellai et al., 2003). Beneficial effects of diet restriction (Masoro, 2005) and dwarf mutations, both of which extend lifespan in rodents, may, to some degree, result from repression of the mTOR complex 1 (mTORC1) pathway (Sharp and Bartke. 2005 Hsieh and Papaconstantinou, 2004).

It is not yet known to what extent inhibition of mTOR will recapitulate other aspects of the phenotypes associated with diet restriction or dwarf mutations. The demonstration that rapamycin feeding increases lifespan even when started late in life, as well as the absence of changes in body weight, distinguishes these results from studies using diet restriction: in all cases diet restriction reduces body weight, and in most reports (Mason), 2005), although not all (Dhahbi et al., 2004), diet restriction produces little, if any, benefit if started after about 550 days of age.

To illustrate biochemical effects of the dose of rapamycin used in this study, the phosphorylation status of ribosomal protein subunit S6 (rpS6), a target substrate of S6 kinase 1 in the mTOR signaling pathway (Petroulakis et al., 2007) was evaluated, in white adipose tissue (WAT) in a separate group of young adult UM-HET3 mice fed rapamycin-containing food for 5 weeks. Phosphorylated-rpS6 is greatly reduced, becoming barely detectable in rapamycin-fed mice, relative to total rpS6 (FIG. 5). While most of the control mice have a robust signal for phosphorylated rpS6, some have very little of this modification. Importantly, all mice fed rapamycin have very little phosphorylated rpS6.

Figure 6:
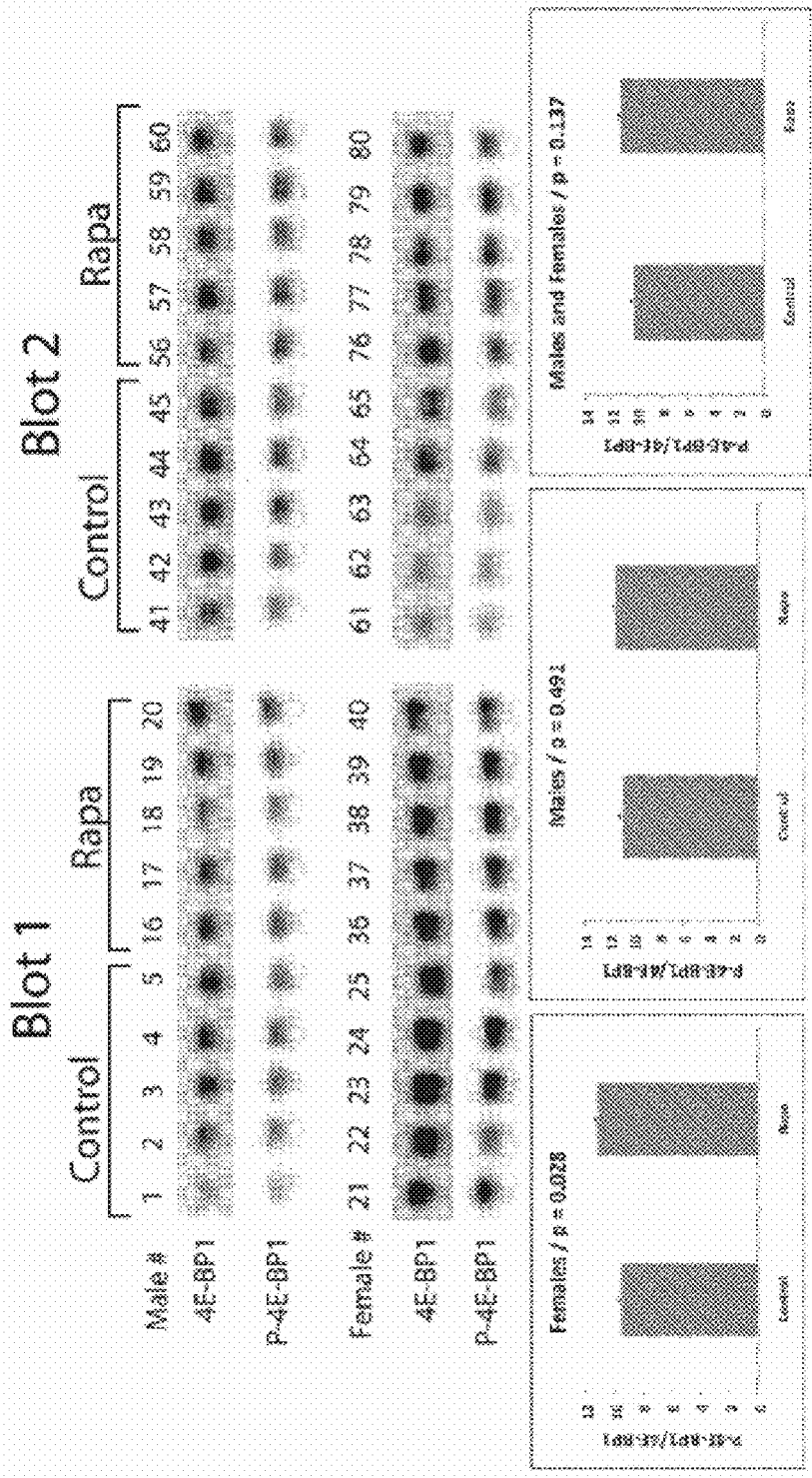
FIG. 6. Reduced P-rpS6(Ser240/244) in Liver.

Liver and brain were assayed to determine if this dose of rapamycin in food affected rpS6 phosphorylation in other organ systems. FIG. 6 shows immunoblot assays of rpS6 phosphorylation in liver. Quantification of the ratio of phosphorylated rpS6 to total rpS6 protein at this dose of rapamycin (see graphs for females, males and both) is more pronounced in males than females, the latter of which reach statistical significance in this assay. Analysis of combined male and female phosphorylated rpS6 showed significantly lower levels in treated mice. Our conclusion for S6 kinase 1 activity in liver is that both sexes are responding at this dose of rapamycin, with males being more responsive.

Figure 7:
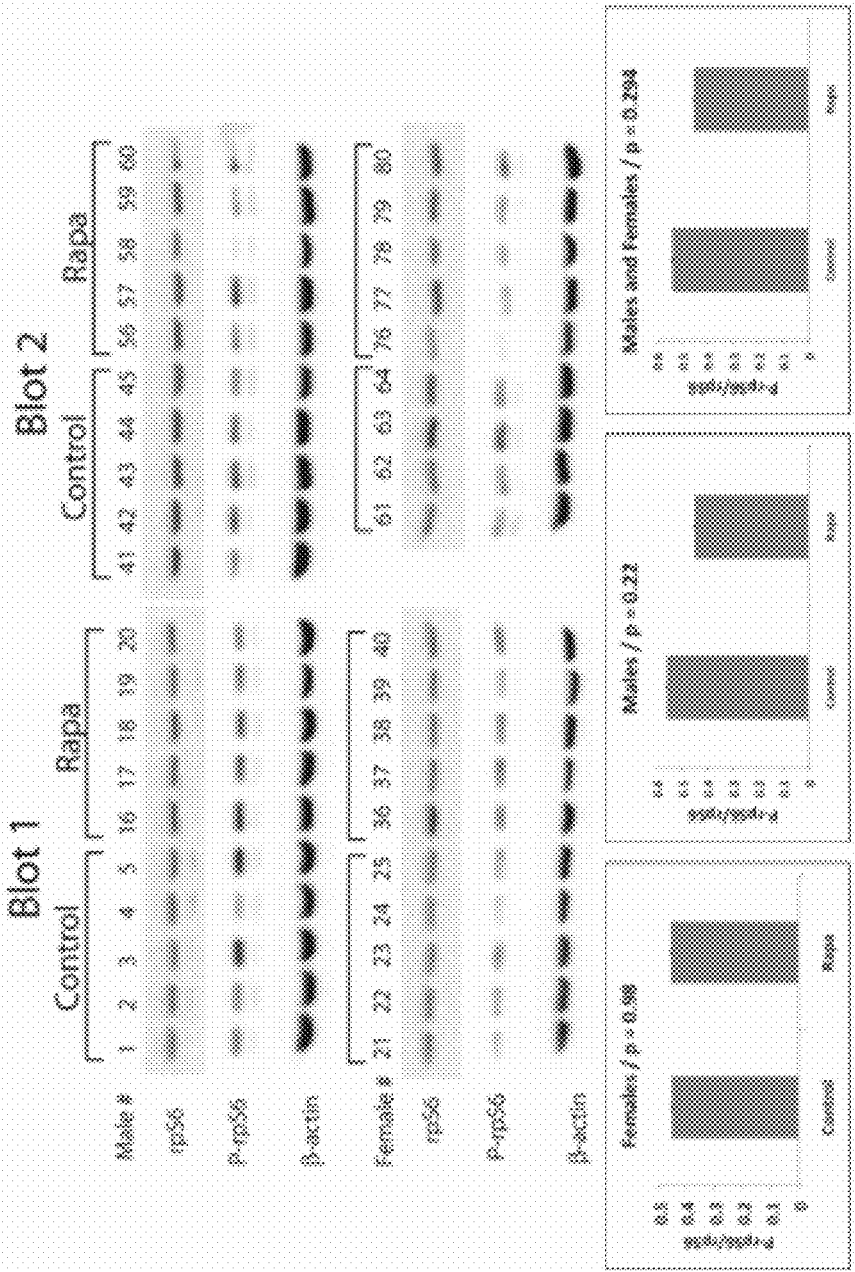
FIG. 7. No detectable effects on P-rpS6(Ser240/244) in brain.

FIG. 7 shows an analysis of S6K1 activity in the brain from rapamycin treated and untreated UM-Het3 mice. The effect on mTOR/S6K1 as measured by this assay is much less pronounced in brain compared to WAT and liver. Since rapamycin readily crosses the blood brain barrier (Pong and Zaleska, 2003), this response is interesting and could be biomedically relevant.

Figure 8:
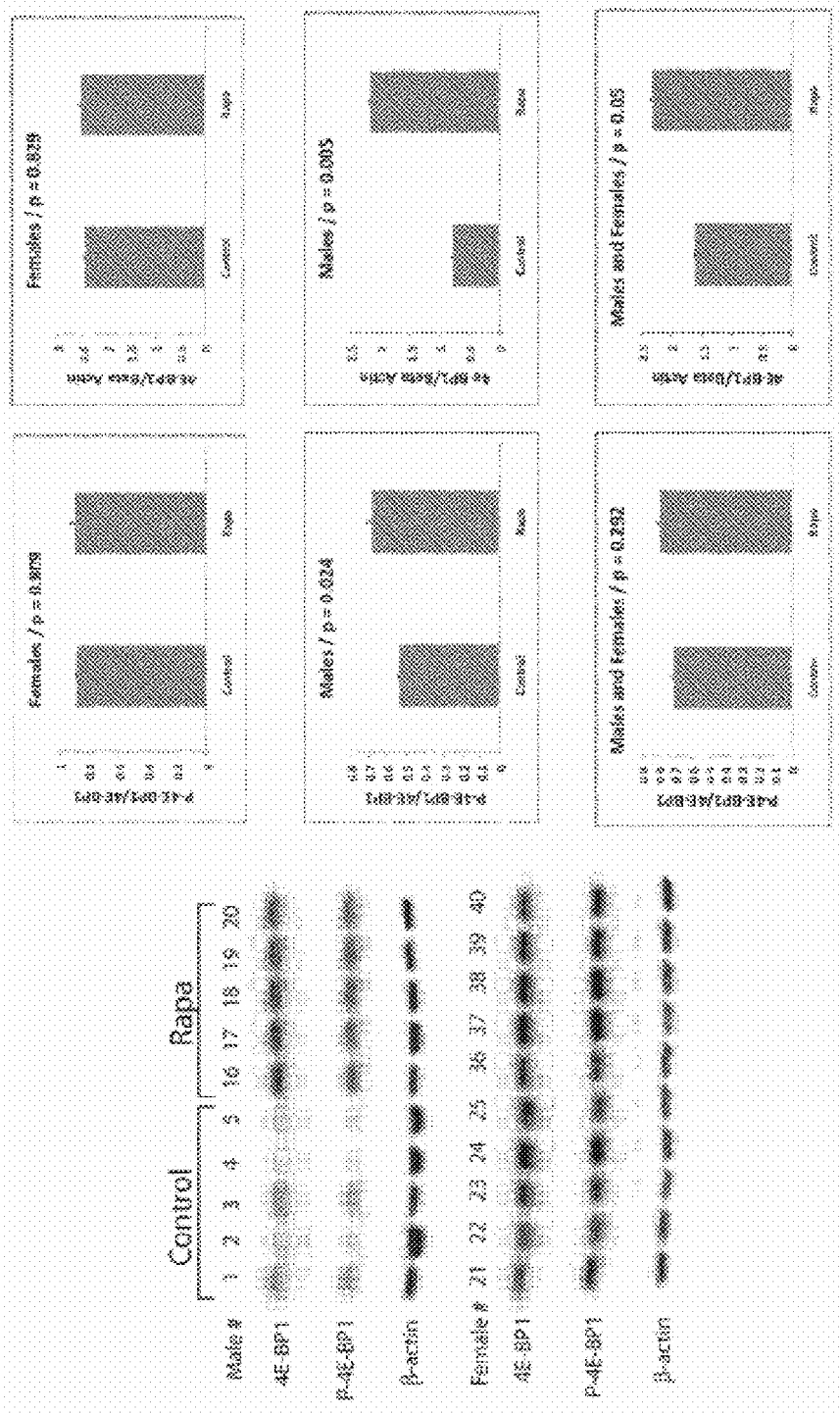
FIG. 8. Increase in 4E-BP1 in male white adipose tissue.

When nutrients, energy and growth factor inputs are favorable for activation of mTORC1 kinase activity, another of its target substrates is 4E-BP1, a repressor of cap-dependent translation (Gingras et al., 2001). Phosphorylation of 4E-BP1 inhibits its repressor function. Rapamycin inhibits mTORC1-mediated phosphorylation of 4E-BP1. Analysis of 4E-BP1 in WAT in UM-Het3 mice chronically treated with rapamycin revealed that the ratio of phosphorylated 4E-BP1 was no different in a combined analysis of males and females (FIG. 8). There is a significant increase in total 4E-BP1 proteins, relative to β-actin, in fat from rapamycin-consuming male mice. WAT from females treated chronically with rapamycin showed no difference in the ratio of phosphorylated 4E-BP1 compared to total 4E-BP1, or in levels of 4EBP1 protein compared to β-actin. There is an increased sensitivity of males to rapamycin treatment; ratios of phosphorylated 4E-BP1 to total protein are statistically different relative to controls. Also there is an increase in 4E-BP1 total proteins compared to β-actin. These data are consistent with cell-based studies showing a differential inhibition of S6K1 and 4E-BP1, which is cell-type-specific (Choo et al., 2008.). While rapamycin inhibits S6K1 activity over the course of their experiments (24-48 hours), 4E-BP1 phosphorylation recovers within 6 hours.

Figure 9:
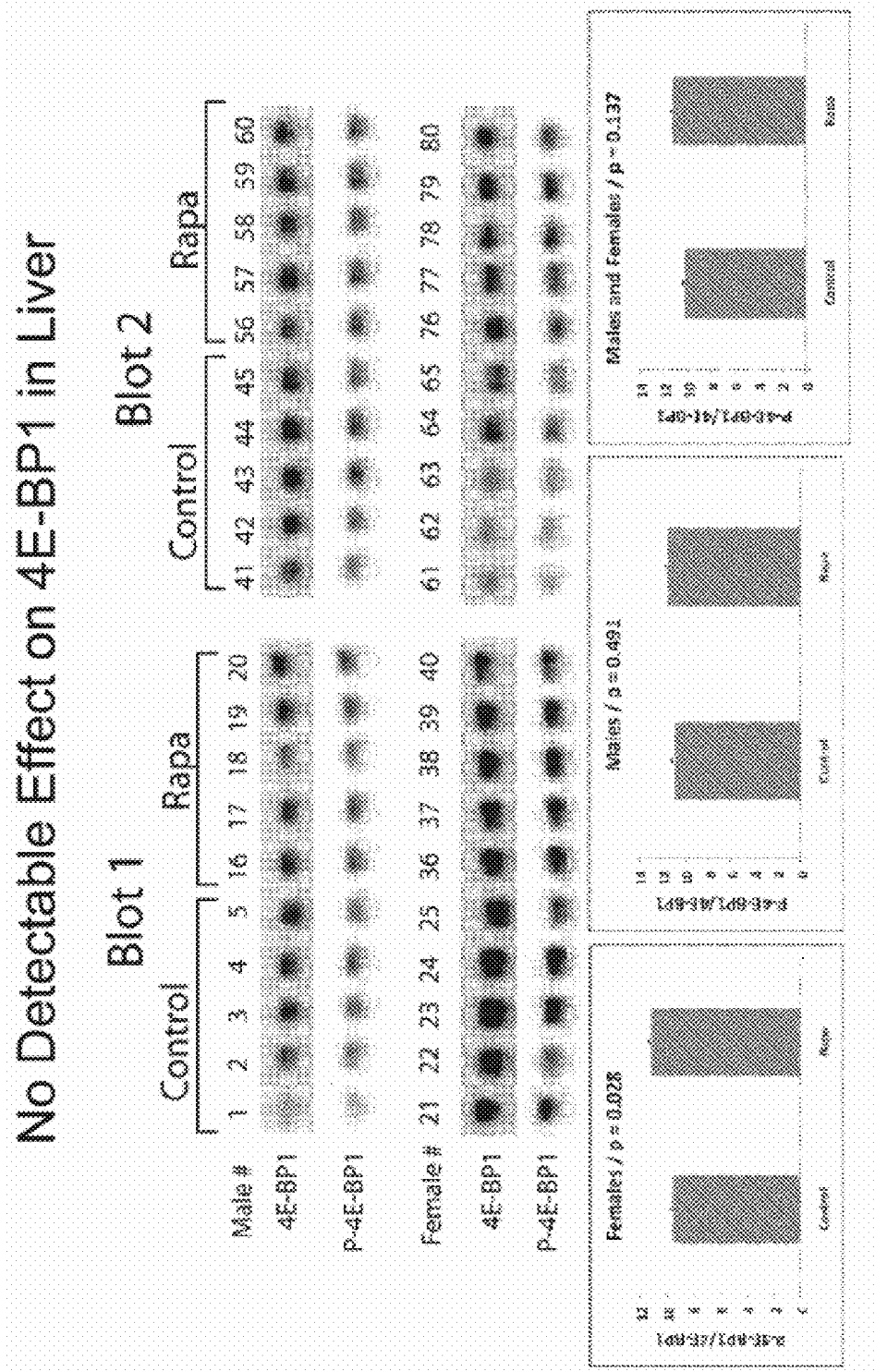
FIG. 9. No detectable effect on 4E-BP1 in liver.

FIG. 9 shows immunoblot assays of 4E-BP1 phosphorylation in liver from mice chronically treated with rapamycin. Again, consistent with cell-based experiments, there was no statistical difference in the ratio 4E-BP1 phosphorylation in males or females, in fact phosphorylation increased modestly in the five females assayed in this experiment. Since β-actin was not assayed in these experiments, 4E-BP1 levels were not analyzed.

Note that 4E-BP2 is the dominant form of 4E-BP proteins expressed in the brain (Banko et al., 2005). The immunological reagents used above are specific for 4E-BP1, thus an analysis of these translation repressors in the brain is pending development of 4E-BP2-specific antibodies.

Figure 10:
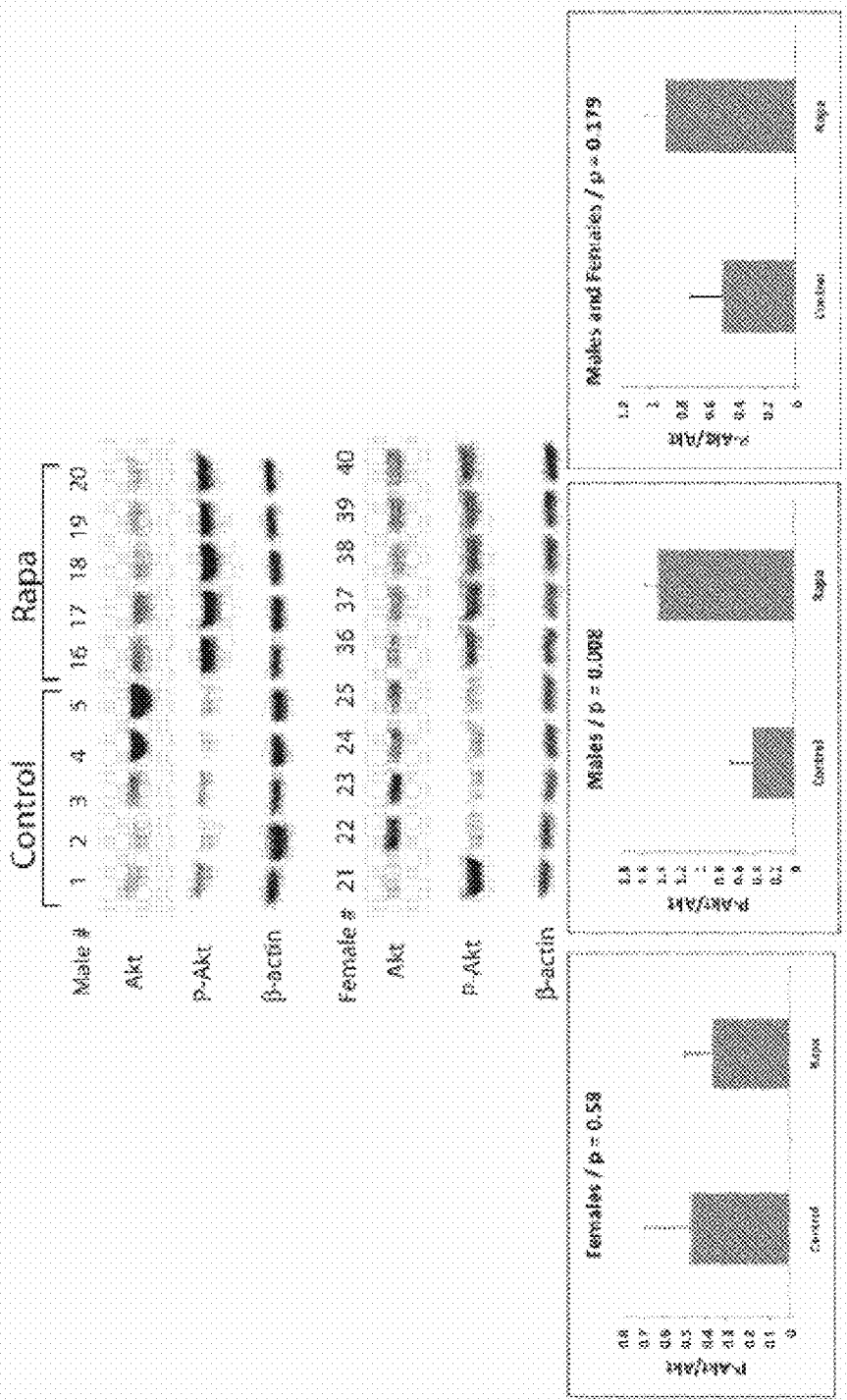
FIG. 10. Akt activation in male white adipose tissue.

In vivo evidence indicates that activation of S6K1 acts to suppress insulin signaling through modulation of IRS1 (Um et al., 2006). This predicts that rapamycin treatment de-represses this signaling, leading to an increase in Akt phosphorylation. Immunoblot results of an analysis of Akt phosphorylation in WAT obtained from mice consuming rapamycin-containing food showed that in females there is no difference in the level of phosphorylation of Akt in response to rapamycin treatment. The results in males in FIG. 10 a clear increase in phosphorylation of Akt compared to controls. When combined, data on males and females is highly significant.

Figure 11:
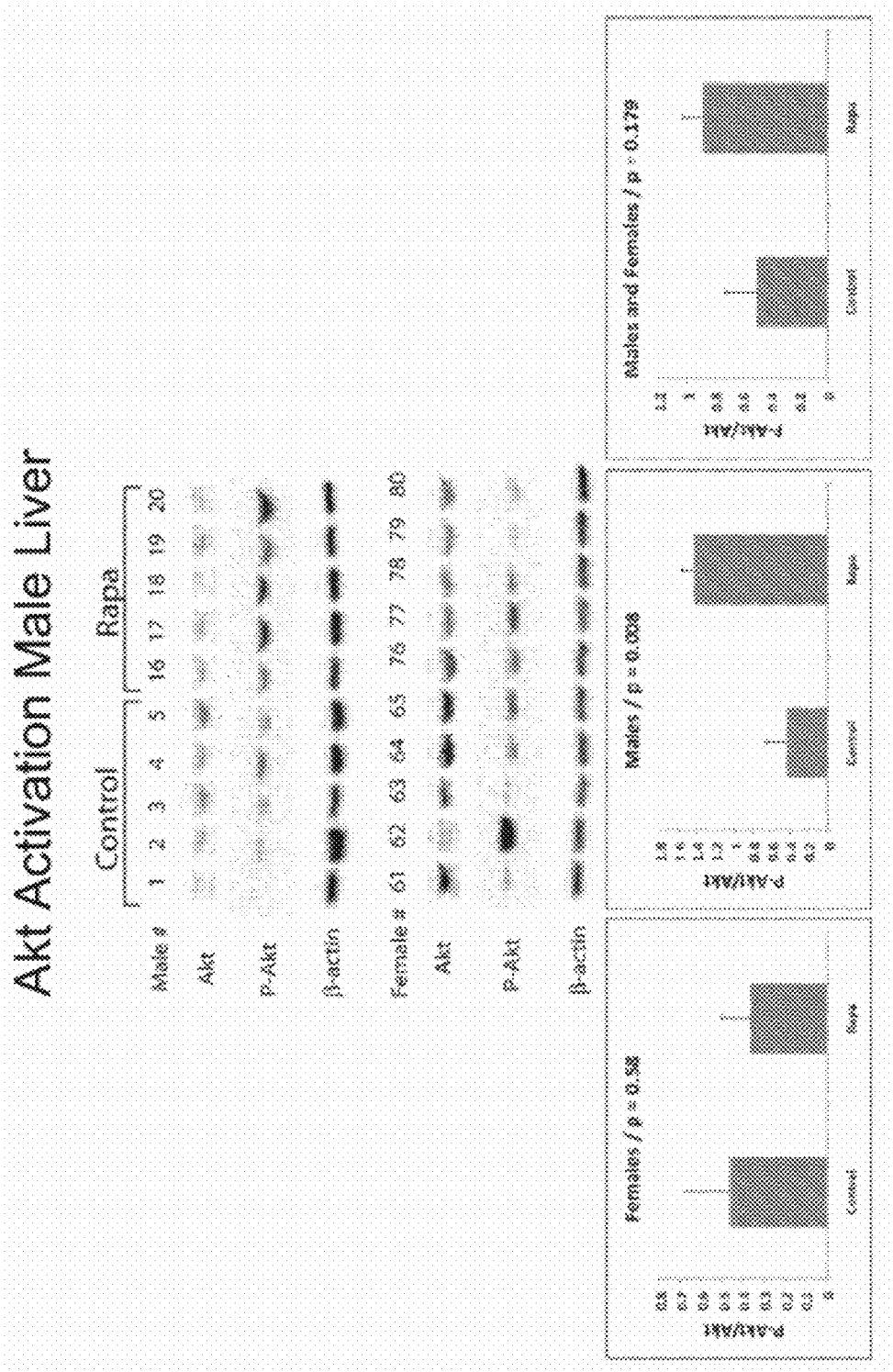
FIG. 11. Akt activation in male liver.

FIG. 11 shows immunoassay data for Akt activation in liver of UM-Het3 mice consuming food that contains rapamycin. As documented in WAT above, we observe a significant increase in Akt phosphorylation in male, but not female, liver.

Figure 12:
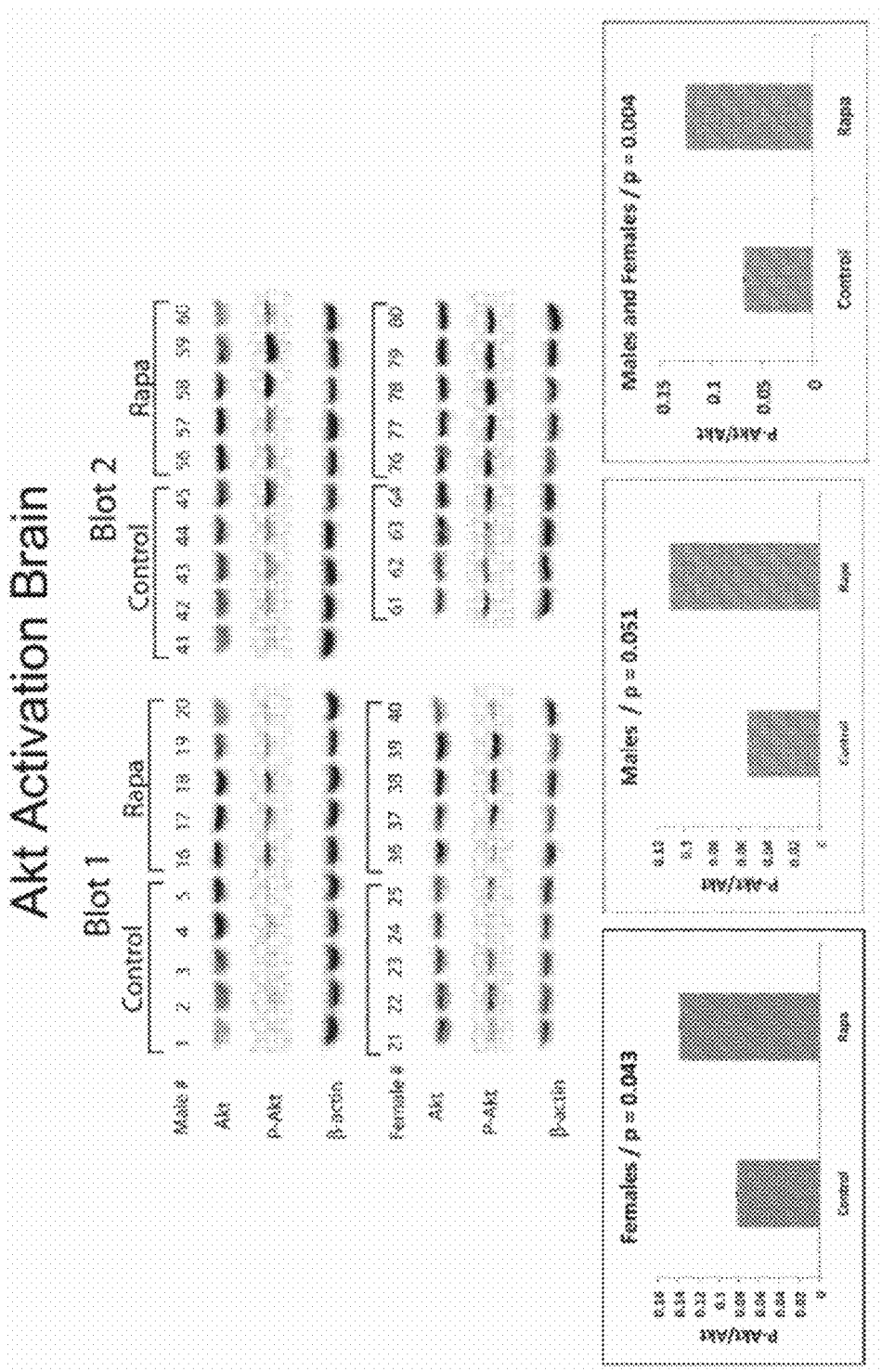
FIG. 12. Akt activation in brain.

FIG. 12 shows immunoassay data for Akt activation in brain of UM-Het3 mice consuming food that contains rapamycin. Interestingly, there appears to be a significant increase in Akt phosphorylation in the rapamycin-treated mice, both males and females.

Summarizing these immunoassays to determine the organ-specific effects of chronic exposure to dietary rapamycin, all of the organs tested show evidence of expected effects on down stream and upstream mTORC1 effectors. For S6K1 activity, WAT appears to be hypersensitive at the 7-ppm dose compared to liver. Male WAT appears to be more sensitive than female. Brain S6K1 activity was no different in rapamycin-treated mice compared to controls. For 4E-BP1 phosphorylation, there were little effects documented in any tissue assayed, consistent with cell-based experiments showing recovery of 4E-BP1 phosphorylation after 6-24 hours of treatment. An unexpected increase in the levels of 4E-BP1 in male WAT was documented. Akt activation was observed in male, but not female WAT and liver. Brain Akt was elevated by rapamycin in both male and females. Thus, there appears to be organ- and sex-specific responses to the level of rapamycin tested, which is again consistent with cell-based analyses of rapamycin effects. Based on these results, it is concluded that dietary rapamycin is having the expected biological effects on target organs tested.

Example 2

Studies to Examine Rapamycin Stability in Food

Figure 13:
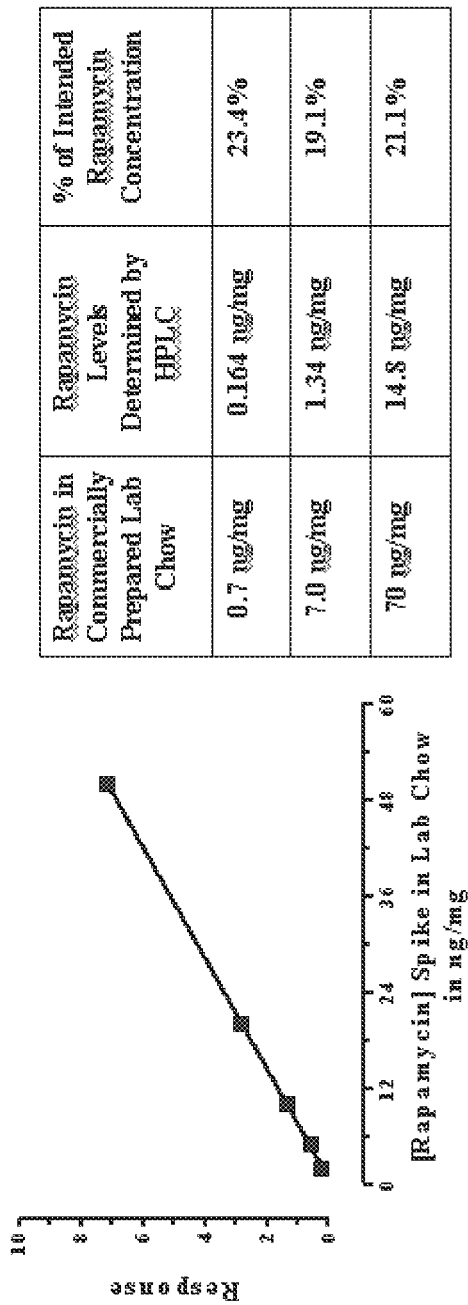
FIG. 13. Stability of rapamycin in food.
Figure 14:
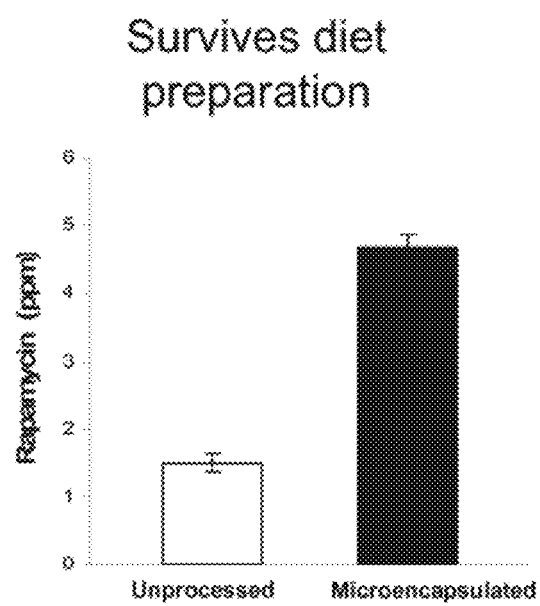
FIG. 14. Encapsulation of rapamycin improves stability in laboratory chow. Rapamycin was added to commercially prepared lab chow at 7 ppm and the food was then assayed for rapamycin content. Rapamycin levels are less than expected, suggested that rapamycin degraded during preparation or storage of the food (open bar). Microencapsulation of the rapamycin reduced degradation (shaded bar).
Figure 15:
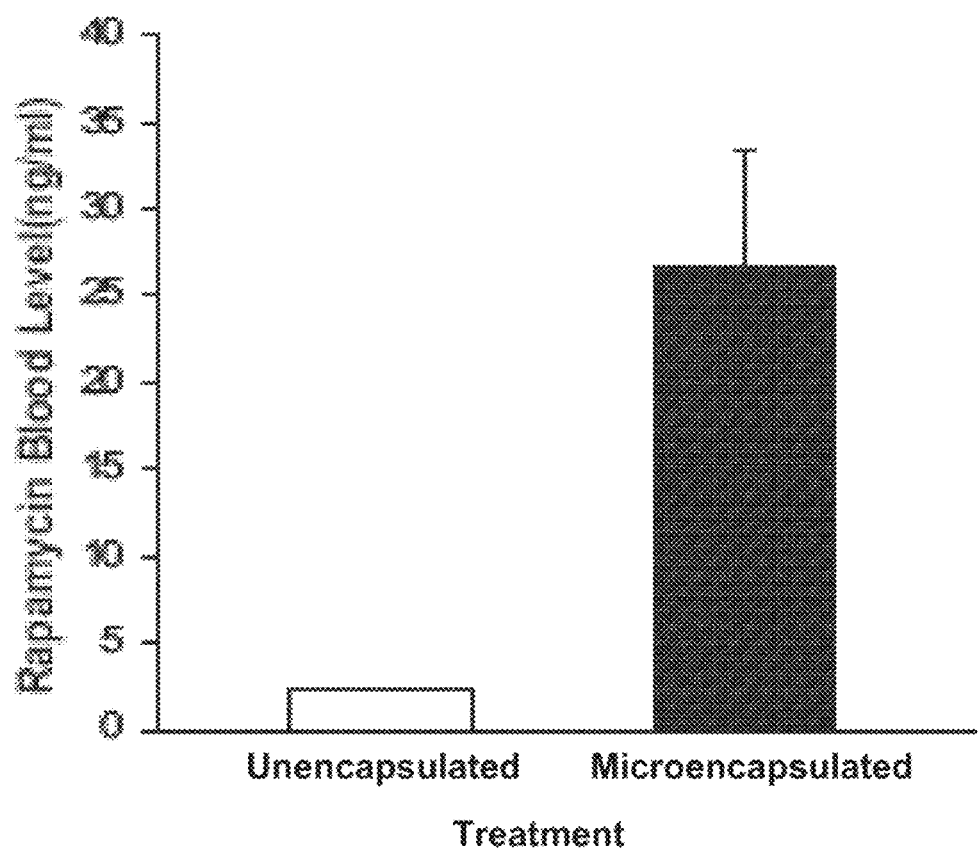
FIG. 15. Rapamycin is detectable in whole blood after feeding diet containing encapsulated or unencapsulated rapamycin. Encapsulated and unencapsulated rapamycin (7 ppm) was fed to mice for 3 weeks and the blood assayed for rapamycin levels. Encapsulation resulted in significantly higher blood levels of rapamycin than observed using unencapsulated rapamycin.
Figure 17:
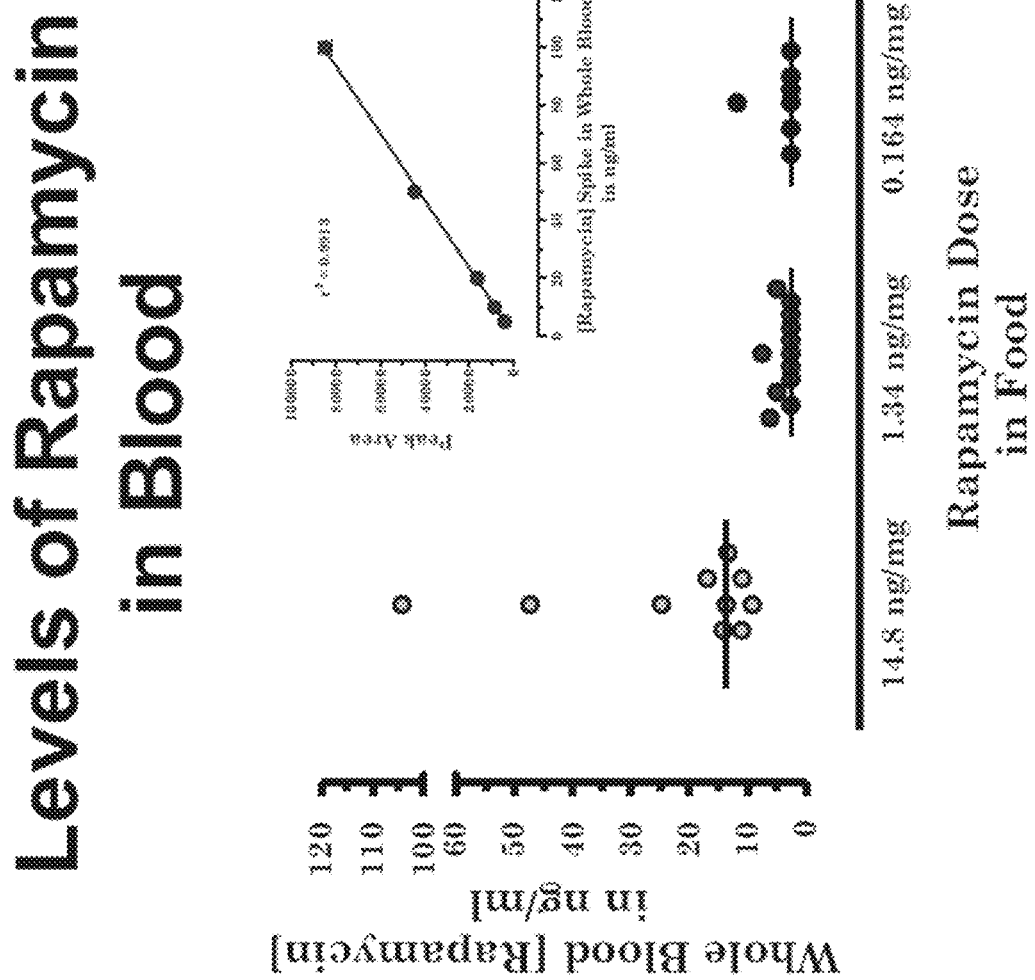
FIG. 17. Levels of rapamycin in blood.
Figure 19:
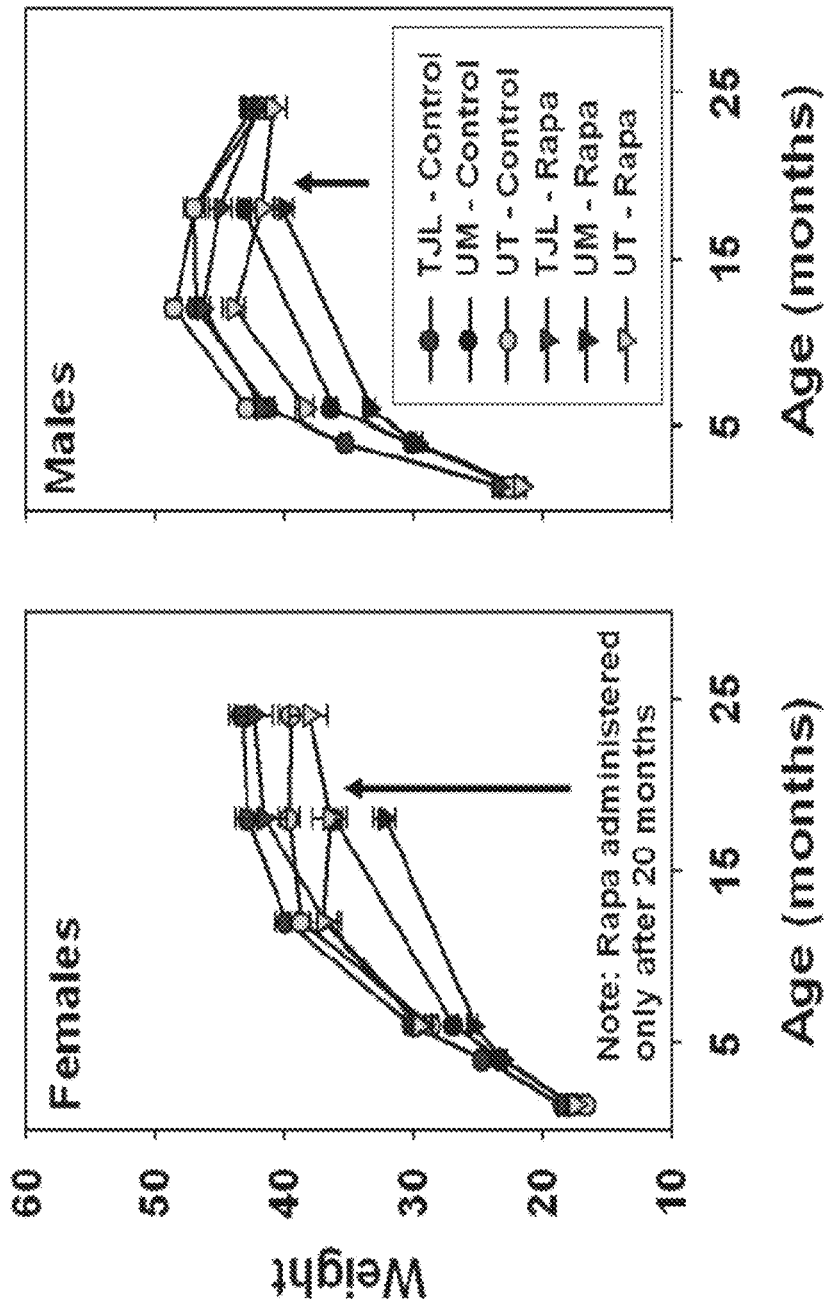
FIG. 19. No effect of rapamycin on body weight.
Figure 20:
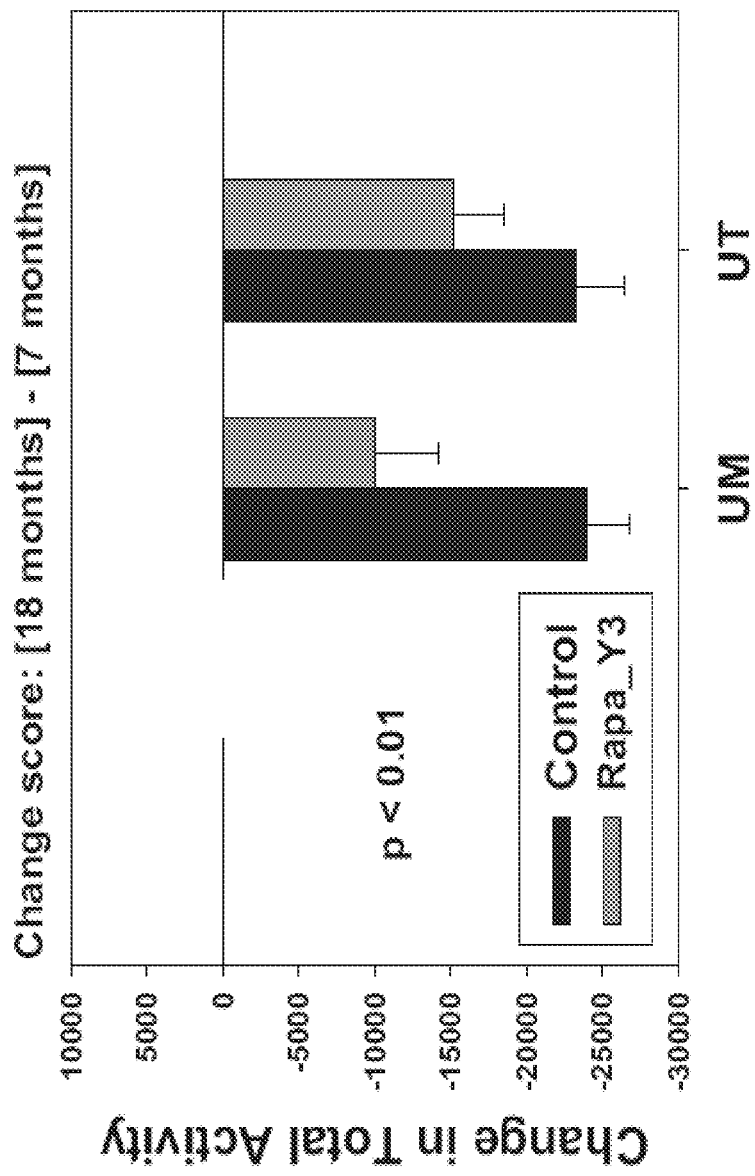
FIG. 20. Rapamycin attenuates age-related decline in general locomotor activity.
Figure 21:
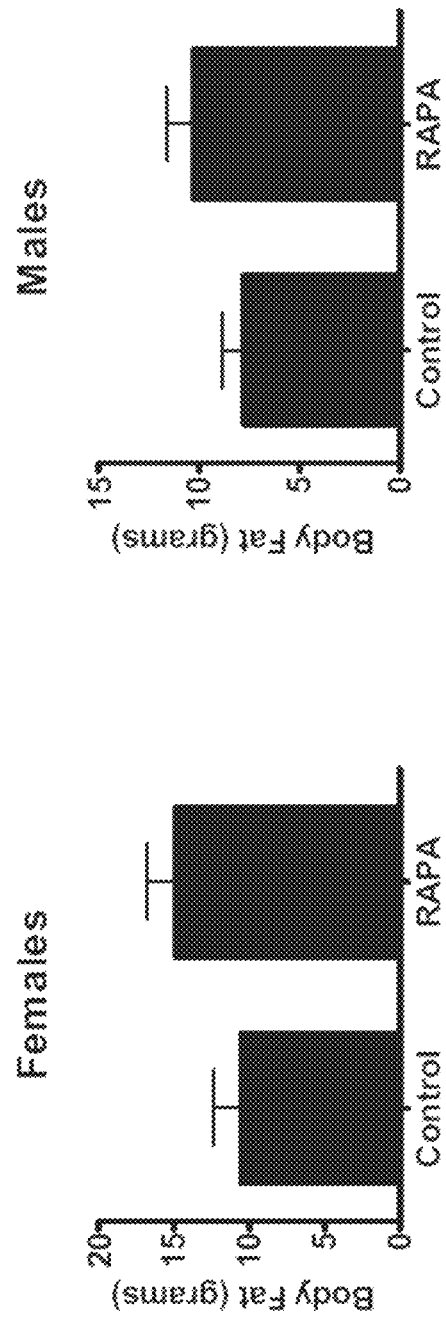
FIG. 21. No significant effect on adiposity in mice fed rapamycin from 9 months of age.
Figure 22:
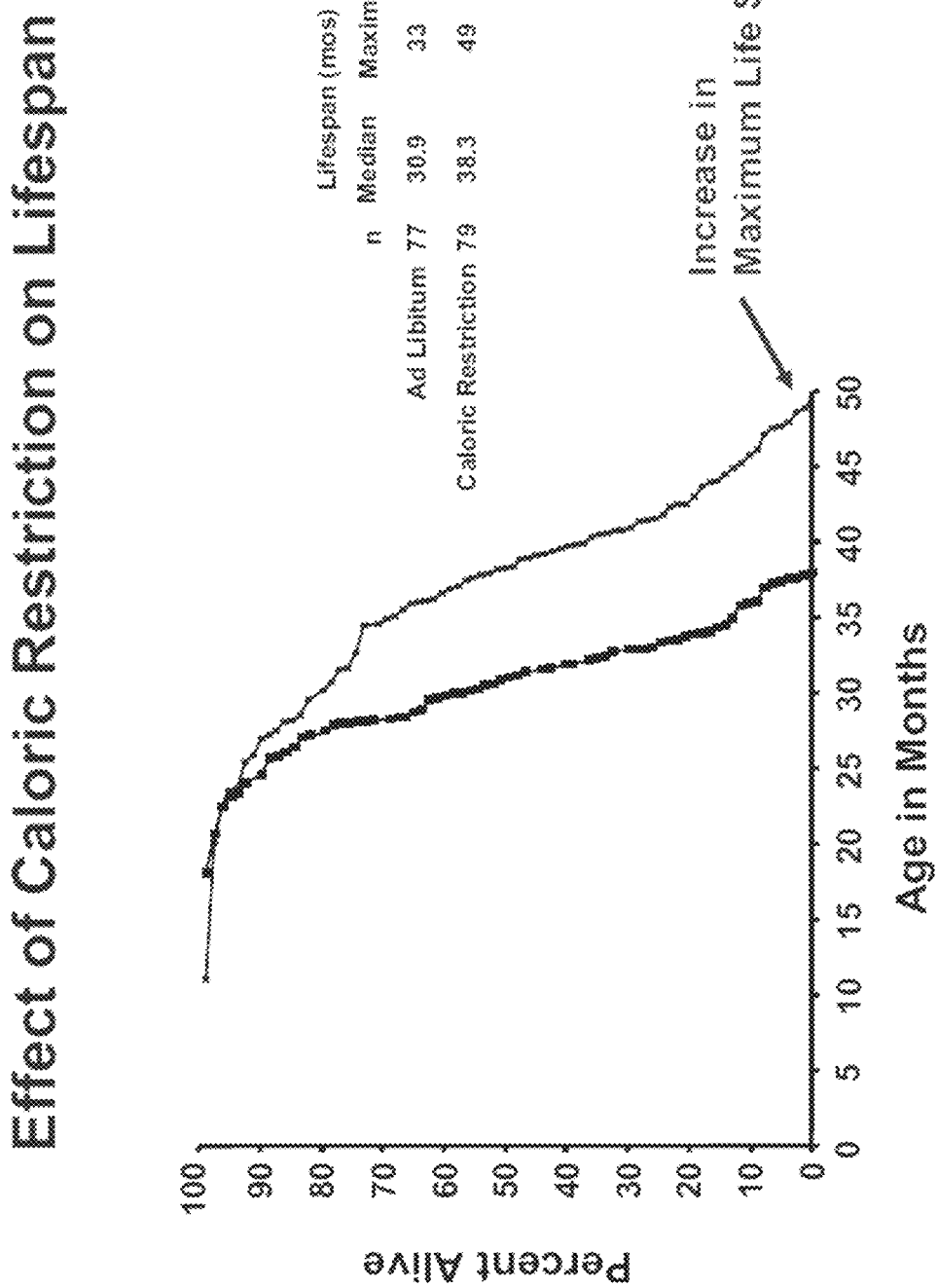
FIG. 22. Effect of caloric restriction on lifespan.
Figure 23:
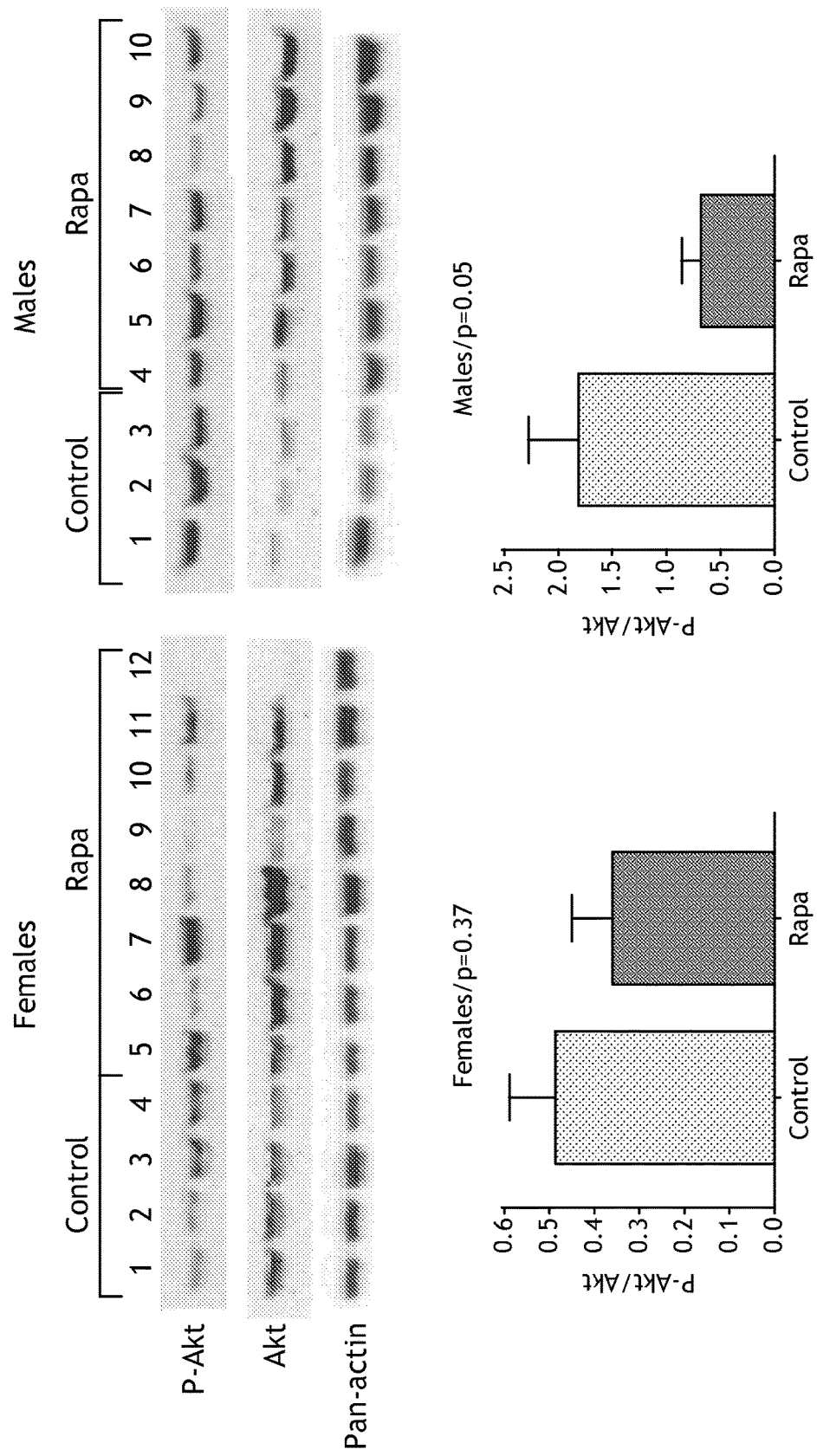
FIG. 23. Visceral fat pad P-Ser473 Akt analysis: 20 months of treatment.
Figure 24:
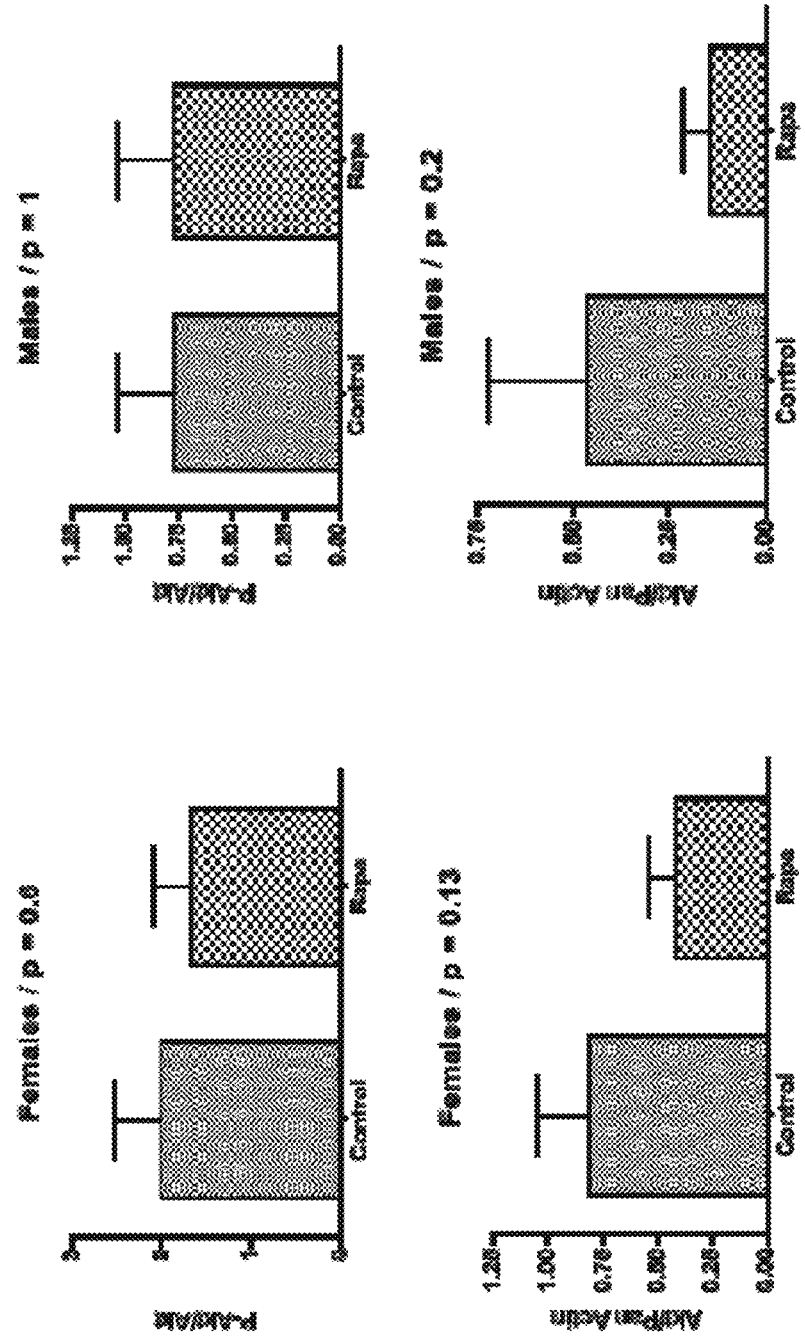
FIG. 24. Gastrocnemius muscle P-Ser473 Akt analysis.
Figure 25:
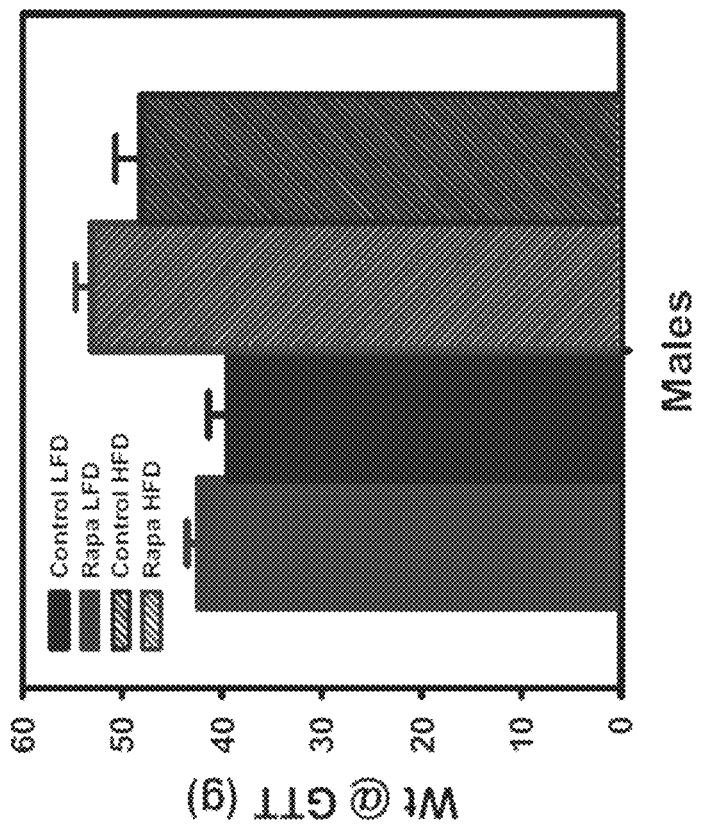
FIG. 25. No difference in body weight with or without rapamycin in mice on a high fat diet 12 weeks of feeding.
Figure 27:
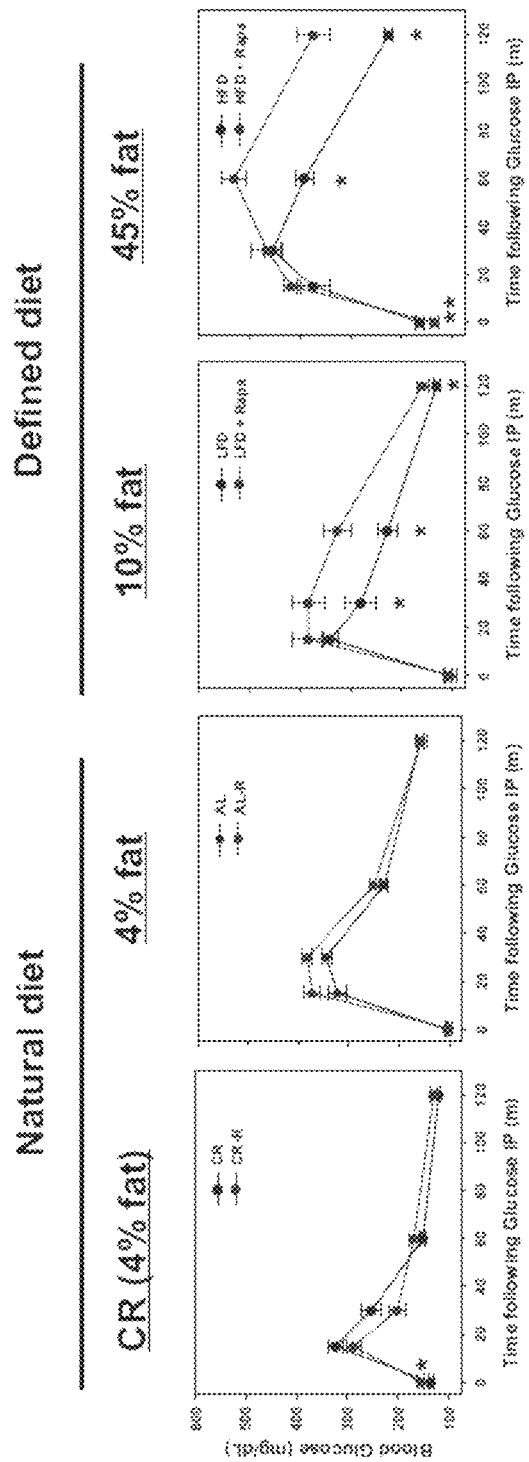
FIG. 27. Effects of increasing dietary fat or calories on rapamycin effects on glucose metabolism.

Studies were conducted to examine the stability of rapamycin in food. Rapamycin was sent to the Southwest Research Institute (San Antonio) for microencapsulation by dissolving the rapamycin in an organic solvent containing a dissolved enteric coating, Eudragit S100. This polymer is stable at pH levels below 7, as discussed in Example 1. Samples of encapsulated and unencapsulated rapamycin were incorporated into commercial mouse chow at a concentration of 0.7, 7, and 70 ppm and the levels of rapamycin in the food were assayed (FIG. 13-14). The encapsulated rapamycin survived the process of incorporation into the chow better than the unencapsulated rapamycin, as demonstrated by the 3-fold higher concentration of rapamycin detected in the diet made with encapsulated rapamycin than in the diet made with unencapsulated rapamycin. Diets made from encapsulated and unencapsulated rapamycin were fed to mice for 4-5 weeks and concentrations of rapamycin in 200 µl of whole blood samples were determined using HPLC with UV detection. The average blood level observed after feeding the encapsulated rapamycin was greater than 25 ng/ml, which compares favorably with therapeutic levels in human treatment protocols of at least 12 ng/ml (FIG. 15). By contrast, mice fed the diet prepared with unencapsulated rapamycin had less than 2.5 ng/ml, which is the detection limit of the assay. As a result, the dose was increased to 14 ppm in the diet for the longevity studies of Example 1.

Example 3

Rapamycin Rescues Cognition and Attenuates Pathology in Mouse Models of Alzheimer Disease Methods
Mice.
Rapamycin administration and behavioral experiments involving hAPP(J20) mice were conducted at the Buck Institute. Experimental groups were: control-fed non-Tg, n=10; rapamycin-fed non-Tg, n=10; control-fed Tg, n=12; rapamycin-fed Tg, n=12, all animals were males and 7 mo. Rapamycin administration and behavioral experiments involving 3×Tg-AD mice were conducted at the UTHSCSA and experimental groups were: control-fed non-Tg, n=13; rapamycin-fed non-Tg, n=14; control-fed 3×Tg-AD, n=14; rapamycin-fed 3×Tg-AD, n=16; males and females were included in equal proportions. The derivation and characterization of the 3×Tg-AD and hAPP(J20) mice have been described elsewhere (Hsia et al., 1999; Mucke et al., 2000; Oddo et al., 2003). The hAPP(J20) mice were maintained by heterozygous crossed with C57BL/6J mice (Jackson Laboratories, Bar Harbor, Me.). The hAPP(J20) mice were heterozygous with respect to the transgene. Non-Tg littermates were used as controls. The 3×Tg-AD mice were homozygous for the APP and tau transgenes and for the M146V mutation knocked into the PS1 gene.

Rapamycin Treatment.
Mice were fed chow containing either microencapsulated rapamycin at 2.24 mg/kg or a control diet as described in Example 1. For the duration of the treatment, all mice were given ad libitum access to rapamycin or control food and water.

Behavioural Testing.
The MWM (protocol detailed in Supplementary Information) was used to test spatial learning and memory. The Morris water maze (MWM) (Morris, 1984) was used to test spatial memory. All animals showed no deficiencies in swimming abilities, directional swimming or climbing onto a cued platform during pre-training and had no sensorimotor deficits as determined with a battery of neurobehavioral tasks performed prior to testing. All groups were assessed for swimming ability with a straight water alley (15 by 200 cm) containing a submerged (1 cm) 12×12 cm platform 2 days before testing. The procedure described by Morris et al., 2006 was followed as described (Galvan et al., 2006; Galvan et al., 2008). Briefly, the J20 mice were given a series of six trials, one hour apart in a light-colored tank filled with opaque water whitened by the addition of non-toxic paint at a temperature of 24.0±1.0° C. In the visible portion of the protocol, which tests non-spatial learning, animals were trained to find a 12×12-cm submerged platform (1 cm below water surface) that was marked with a colored pole that served as a landmark and which was placed in different quadrants of the pool. The animals were lowered into the pool facing the pool wall and were released at different locations in each trial. Each animal was given a maximum of 60 seconds to find the submerged platform. If it did not find the platform in that time, the animal was gently guided to it. After remaining on the platform for 20 seconds, the animal was removed and placed in a dry cage. Twenty minutes later, each animal was given a second trial, using a different release position. This process was repeated a total of 6 times for each mouse, with each trial about 20 minutes apart. In the non-cued part of the protocol, the water tank was surrounded by opaque dark panels at approximately 30 cm from the edge of the pool. Four rectangular drawings with geometric designs in black and white were evenly spaced on the panels to serve as distal cues. The animals were trained to find the submerged platform by swimming 6 times every day for 2 days following the same procedure described for the cued training above. These 6 trials were then followed by a probe trial for which the platform was removed from the pool. In the probe trial, each animal was allowed to swim for 30 seconds before being removed. The percent of time spent in the area previously containing the platform, as well as the number of times that each animal crossed the previous platform location were determined as a measure of platform location retention. Because rodents are good swimmers and are monitored while in the water, they never drown and do not suffer significant adverse effects from this test. During the course of testing, animals were monitored daily, and their weights are recorded weekly. Performance in all tasks was recorded by a computer-based video tracking system (Water2020, HVS Image, U.K). Data were analyzed offline by using HVS Image and processed with Microsoft Excel. The MWM testing for the 3×Tg-AD mice was conducted in a circular tank of 1.5 meters in diameter located in a room with extra maze cues. The location of the platform (14 cm in diameter)

was kept constant for each mouse during training and was 1.5 cm beneath the surface of the water, which was maintained at 25° C. throughout the duration of the testing. During training, the mice received four trials a day that were alternated among four pseudorandom starting points with a 25-second intertribal interval. If a mouse failed to find the platform within 60 seconds, it was guided to the platform by the researcher and kept there for 10 seconds. Probe trials were conducted twenty-four hours after the last training trial. During the probe trials, the platform was removed and mice were free to swim in the tank for sixty seconds. The training and probe trials were recorded by a video camera mounted on the ceiling and data were analyzed using the EthoVisioXT tracking system.

Western Blotting, Aβ Determinations and Immunohistochemistry.

Tissue was processed and analyzed as described previously 13, 25, 26 and is described in detail in Supplementary Information. Aβ and tau were measured using specific ELISAs.

3×Tg-AD mice were sacrificed by CO2 asphyxiation. The brains were extracted and cut in-half sagitally and tissue was processed as described (Oddo et al., 2008). The hAPP(J20) mice were euthanized by isoflurane overdose. Hemibrains were flash frozen. One hemibrain was homogeneized in liquid N2 while the other was used in immunohistochemical determinations. For Western blot analyses, proteins from both hAPP(J20) and 3×Tg-AD soluble fractions were resolved by SDS/PAGE (Invitrogen, Temecula, Calif.) under reducing conditions and transferred to a nitrocellulose or PVDF membrane. The membrane was incubated in a 5% solution of non-fat milk or in 5% BSA for 1 hour at 20° C. After overnight incubation at 4° C. with the appropriate primary antibody, the blots were washed in Tween 20-TBS (T-TBS) (0.02% Tween 20, 100 mM Tris pH 7.5; 150 nM NaCl) for 20 minutes and incubated at 20° C. with secondary antibody. The blots were then washed in T-TBS 3 times for 20 minutes each and then incubated for 5 minutes with Super Signal (Pierce, Rockford, Ill.), washed again and exposed to film. Aβ40 and Aβ42 levels were measured from the soluble and insoluble fractions using a sandwich ELISA protocol as described previously (Oddo et al., 2005). Aβ40 and Aβ42 in hAPP(J20) mice were quantitated in guanidine homogenates of Tg hAPP(J20) hemibrains as described (Galvan et al., 2006) using specific ELISA assays (Invitrogen, Carlsbad, Calif.).

Concerning immunohistochemistry, ten-micrometer cryosections from snap-frozen brains were post-fixed in 4% paraformaldehyde and stained with LC3-specific antibodies (10 µg/ml, Nous, Littleton, Colo.) followed by AlexaFluor488-conjugated donkey anti-rabbit IgG (1:500, Molecular Probes, Invitrogen, CA), and imaged with a epifluorescence microscope (Nikon Eclipse E800 with a FITC cube) and with a laser scanning confocal microscope (Zeiss LSM 510) using a 488 Argon laser and a 505 long pass filter. Images were obtained using 20× and 60× objectives. The z-stacks of confocal images were processed using LSM Viewer software (Zeiss). Aβ and tau immunohistochemistry was performed in 50 µm thick sections obtained using a vibratome slicing system and standard protocols. Images were obtained with a digital Zeiss camera and analyzed with ImageJ.

Statistical Analyses.

Statistical analyses were performed using GraphPad Prism (GraphPad, San Diego, Calif.) and StatView. In two-variable experiments, two-way ANOVA followed by Bonferroni's post-hoc tests were used to evaluate the significance of differences between group means. When analyzing one-variable experiments with more than 2 groups, significance of differences among means was evaluated using oneway ANOVA followed by Tukey's post-hoc test. Evaluation of differences between two groups was evaluated using Student's t test. Values of P<0.05 were considered significant.

Results

Figures 1, 29H:
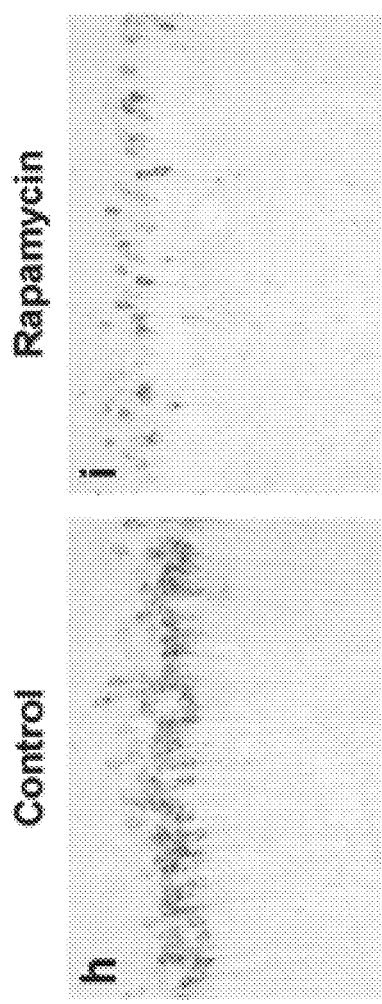
Figures 1, 30A:
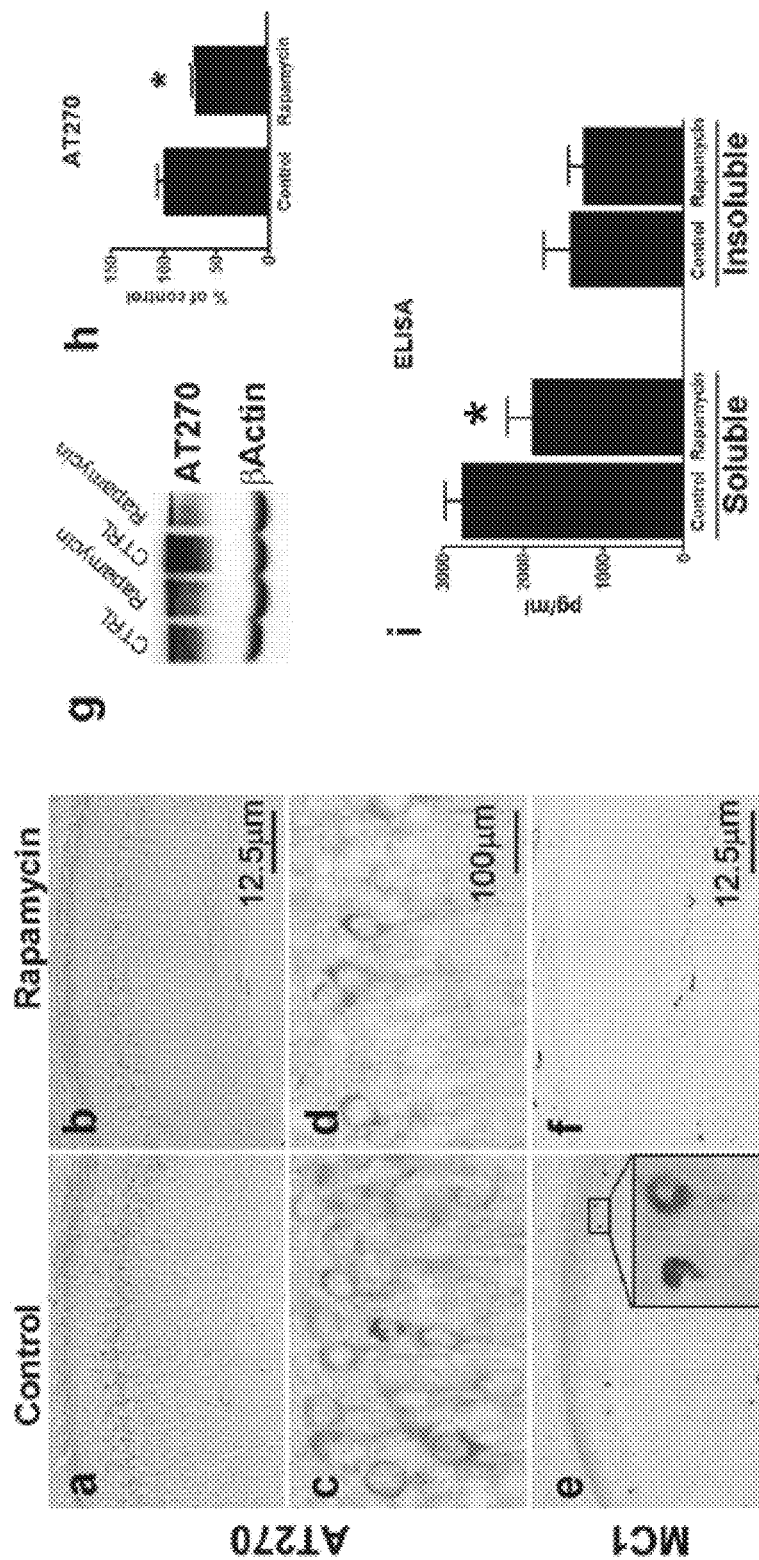

Studies were conducted to determine whether rapamycin prevents or delays age-associated disease such as AD. A rapamycin-supplemented diet, which was identical to the diet that extended lifespan in mice (as set forth in Example 1), or a control chow was fed to the 3×Tg-AD and hAPP (J20) mice. Functional and biochemical outcomes in two independent laboratories at separate locations were measured. The 3×Tg-AD and hAPP(J20) mice and the appropriate non-transgenic controls were treated for 10 and 12 weeks starting at 6.5 and 7 months of age, respectively. At the end of treatment, learning and memory were tested using the Morris water maze (MWM). Significant deficits in learning and memory were observed in control-fed Tg animals (FIG. 28), consistent with previous observations in both mouse models (Oddo et al., 2008; Galvan et al., 2006; Galvan et al., 2008; Saganich et al., 2006; Billings et al., 2005). Rapamycin-fed Tg mice, however, showed improved learning and memory (FIG. 28). Remarkably, in the rapamycin-fed Tg mice, retention of the former location of the escape platform was restored to levels indistinguishable from those of non-Tg mice in both mouse models (FIG. 28B, 28D). Taken together, these data indicate that rapamycin treatment can ameliorate learning deficits and abolish memory impairments in two independent mouse models of AD. At the end of the behavioral assessment, all mice were euthanized and their brains were isolated and processed for neuropathological or biochemical evaluation. To elucidate the mechanism underlying the improvement in learning and memory in the transgenic mice treated with rapamycin, APP processing by Western blots was analyzed. The levels of full-length APP from transgenic mice on the rapamycin or control diet using 22C11 (an N-terminal specific APP antibody) was first measured. It was found that APP steady-state levels were not significantly altered by rapamycin administration (FIG. 29A, 29C). To investigate the steady-state levels of the major C-terminal derivatives, protein extracts were probed with a C terminal-specific APP antibody. The results indicate that the levels of C99 and C83 were unchanged after rapamycin administration in both transgenic lines (FIG. 29A, 29B, 29D, 29E). These results indicate that rapamycin administration did not alter APP steady-state levels or its processing in either transgenic mouse. At the end of treatment, 3×Tg-AD and hAPP(J20) mice were 8 and 7 months old, respectively. At this age both transgenic mice show an increase in soluble Aβ levels with 3×Tg-AD mice also showing an accumulation of intraneuronal Aβ8, 12, 17. Previous studies have shown that extracellular Aβ deposits are not apparent at this age in either transgenic line (Hsia et al., 1999; Oddo et al., 2003). While Aβ40 levels remained unchanged, it was found that rapamycin significantly decreased soluble Aβ42 levels by 32.78±6.68% in brains of 3×Tg-AD mice and by 52.35±13.14% in brains of hAPP(J20) mice (FIG. 29F, 29G, 29H). The levels of insoluble Aβ40 and Aβ42 were below detection in both transgenic mouse models, consistent with previous reports (Hsia et al., 1999; Mucke et al., 2000; Oddo et al., 2003). To determine whether intracellular Aβ accumulation was affected by rapamycin, hippocampal sections from treated and untreated 3×Tg-AD brains were immunostained with an Aβ-specific antibody. The results indicate a significant decrease in the number of the Aβ-positive neurons in the hippomampi of rapamycin-treated 3×Tg-AD mice as compared to control-fed 3×Tg-AD mice (FIG. 29H, 29I). In addition to Aβ accumulation, 3×Tg-AD mice develop an age-dependent accumulation of phosphorylated and aggregated tau (Oddo et al., 2003a; Oddo et al., 2003b; Oddo et al., 2007). At 8 months of age, 3×Tg-AD mice showed somatodendritic accumulation of soluble tau species that are phosphorylated at different epitopes in CA1 pyramidal neurons. Following rapamycin administration, a marked reduction in tau immunoreactivity was observed using the anti-tau antibodies AT270 and MC-1, which recognize tau phosphorylated at Thr181 and a conformational change in tau, respectively (FIG. 30A, 30B, 30C, 30D). These changes in tau are thought to occur early in the disease process. While MC1-positive neurons become apparent at this age in the hippocampi of 3×Tg-AD mice (FIG. 30E), no MC1-positive neurons were detected in rapamycin-treated mice (FIG. 30E, 30F). The immunohistochemical data were also confirmed by Western blot analysis (FIG. 30G, 30H). To better quantify the changes in tau we measured soluble and insoluble tau levels by sandwich ELISA and found that rapamycin selectively decreased soluble tau levels (FIG. 30I). Taken together, these data indicate that early tau pathology in 8-month-old 3×Tg-AD mice is significantly decreased after rapamycin administration. The decrease in Aβ and tau pathology may be due to a decrease in their production or to an increase in their degradation. The data presented here indicate that the rapamycin-mediated reduction in Aβ and tau levels is not due to changes in production because the steady-state levels of C99/C83 (resulting from cleavage of APP by ß- and α-secretase respectively) as well as the tau transgene were not altered.

Figure 31F:
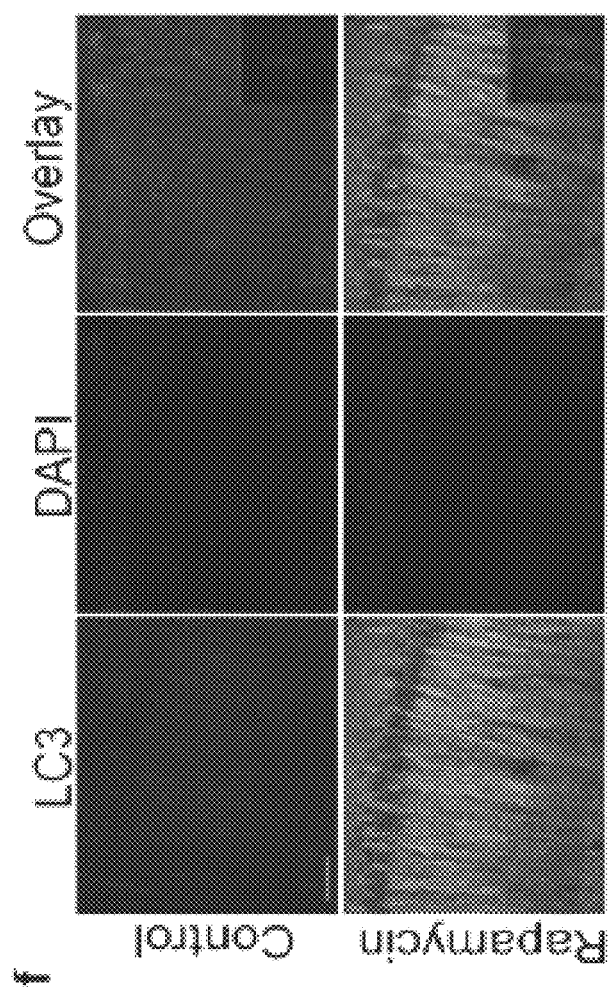

To better understand the mechanism underlying the rapamycin-mediated reduction in Aβ and tau pathology, autophagy, a major cellular degradation pathway, was measured. While the specific mechanisms underlying autophagy induction are still being investigated, the current data indicate a series of proteins known as autophagy-related proteins (Atg) (Mizushima et al., 1998). The formation of a covalent complex between two autophagy-related proteins, Atg5 and Atg12 appears to be essential for autophagy induction (Mizushima et al., 1998; Suzuki et al., 2001). The formation of this complex is regulated by Atg7 and Atg10. Autophagy induction can also be monitored by measuring the levels of light chain 3 II (LC3-II), which is incorporated in the autophagosome membrane during its formation (Kabeya et al., 2000). It was found that the levels of Atg7 and the Atg5/Atg12 complex were significantly increased in rapamycin-treated transgenic mice compared to mice on the control diet (FIG. 31A, 31B, 31C, 31D, 31E), indicating a rapamycin-mediated increase in autophagy. The increase in autophagy was further confirmed by a significant increase in the total levels of LC3-II, as determined by Western blots and by an increase in LC3 immunoreactivity in hippocampal sections (FIG. 31A, 31E, 31F). While we cannot exclude other mechanisms that may be involved in the rapamycin-mediated decrease in Aβ and tau levels, these data support the involvement of autophagy in the amelioration of the AD-like neuropathological phenotype in both animal models.

A decrease in Aβ levels may also contribute to the observed amelioration in tau pathology in 3×Tg-AD mice because it has been shown that lowering Aβ reduces tau pathology (Oddo et al., 2008; Oddo et al., 2006; Oddo et al., 2004). These data are consistent with a recent report in transgenic mice showing that decreasing autophagy increases Aβ levels while increasing autophagy decreases Aβ levels (Pickford et al., 2008). These results, obtained from two independent laboratories, show that rapamycin has a robust protective effect on the development of AD-like neuropathology and rescues the loss of memory in two very different transgenic mouse models of AD. These data show that rapamycin, at a dose that extended lifespan in mice, increases autophagy and reduces AD pathology.

Example 4

Delayed Onset or Less Severe Cancer Contributes to Extended Longevity in Het3 Mice Chronically Treated with Enterically Delivered Rapamycin New data on mTORC1 signaling in Het3 mice chronically treated with enterically delivered rapamycin that is consistent with delayed onset or less severe cancer as one mechanisms contributing to extended longevity.

Since cancer primarily strikes people with a median age of 68 (Edwards et al., 2002), elderly individuals are at greater risk for this disease. In light of this demographic, it is significant that chronic treatment with rapamycin beginning at 20 months of age (60 in human years) extended the life span in the genetically heterogenous mice tested; the primary cause of death was cancer as set forth in Example 1. Thus technology for the prevention of clinically manifested cancer in this population is a goal of cancer research worldwide.

Figure 32A:
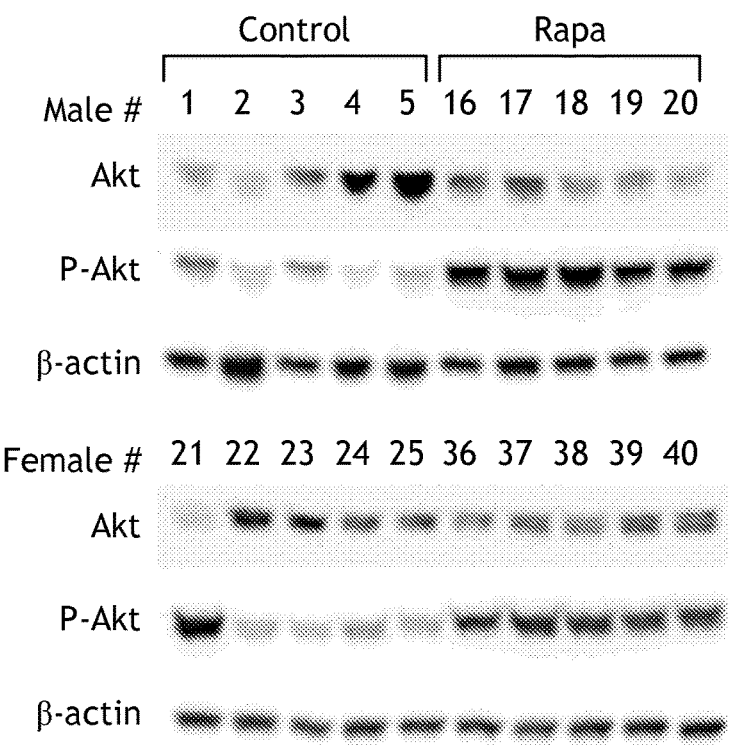
FIG. 32A, 32B. Akt activation in visceral fat of rapamycin-treated UM-HET3 male mice treated for 5 weeks. A) Immunoassay with antibodies used shown to the left of each blot (P-Akt is specific for Ser 473). B) Data were quantified and shown as graphs. Band intensities for female mouse #21 were eliminated from statistical analysis since they were well outside the 95% confidence limits of the mean.
Figure 32B:
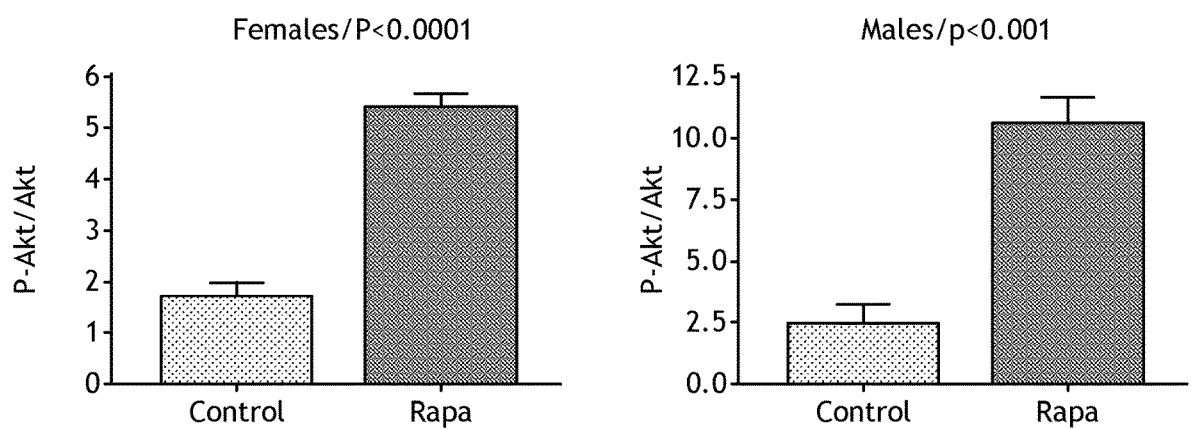

For clinical applications, a major concern is that chronic application of rapamycin or rapalogs in a cancer prevention protocol may result in an increase in Akt Ser463 phosphorylation, which, as a pro growth stimulus (reviewed in Guertin and Sabatini 2009; Lane and Breuleux, 2009), would counteract any repressive effect. Recent immunoblot data from our lab indicates that this does not happen in normal fat and skeletal muscle in a long-term treatment setting. To illustrate, FIG. 32 shows immunoblot assays of visceral fat dissected from mice consuming food with rapamycin for 5 weeks. There was a significant induction in Akt Ser473 phosphorylation in response to this relatively short treatment.

Figure 33:
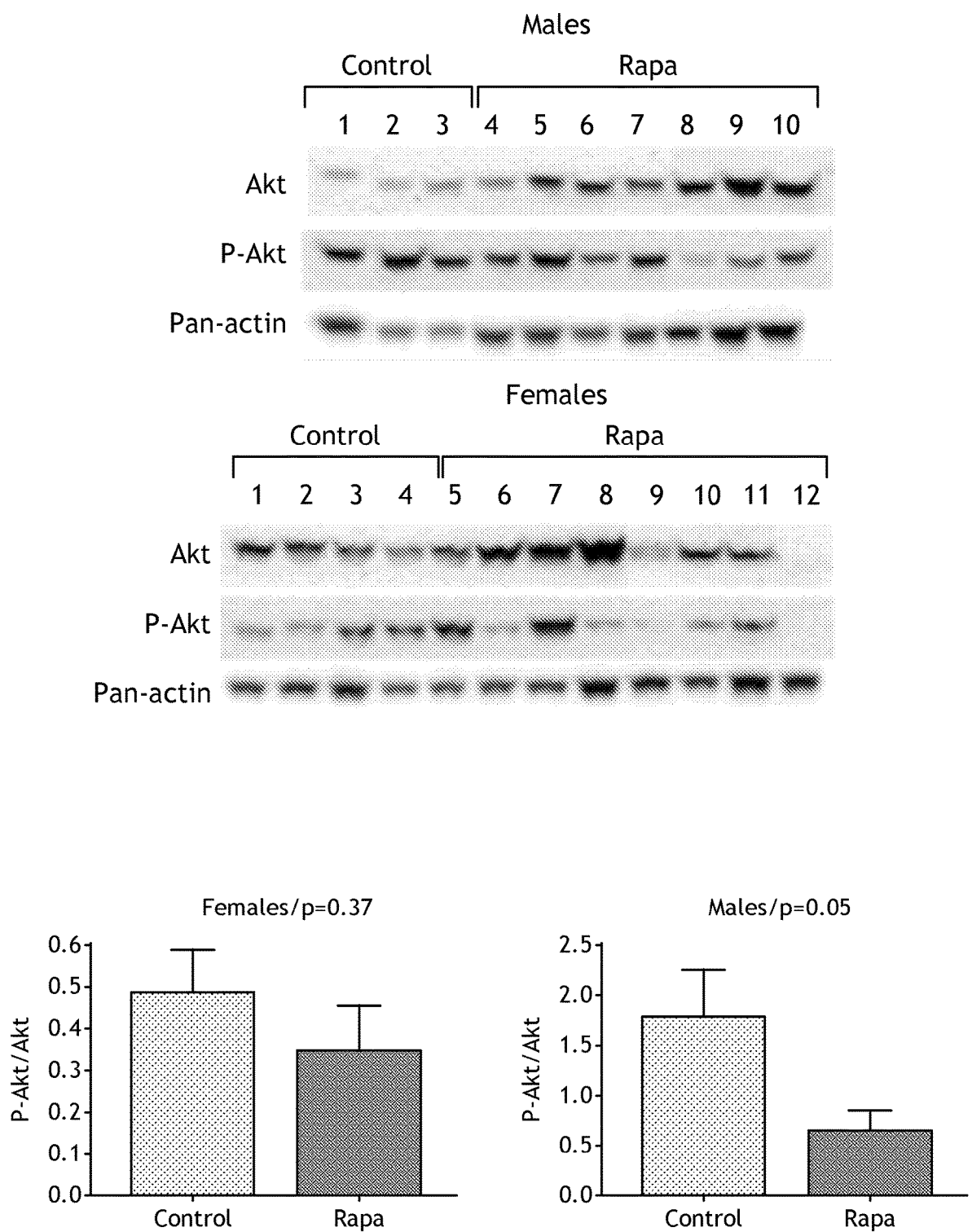
FIG. 33. Reduction of Akt activation in visceral fat of rapamycin-treated UM-HET3 male mice treated for 20 months with rapa. Female data are also shown. Antibodies used are shown to the left of each blot (P-Akt is specific for Ser 473). Data were quantified and shown as graphs below the immunoblots.
Figure 34:
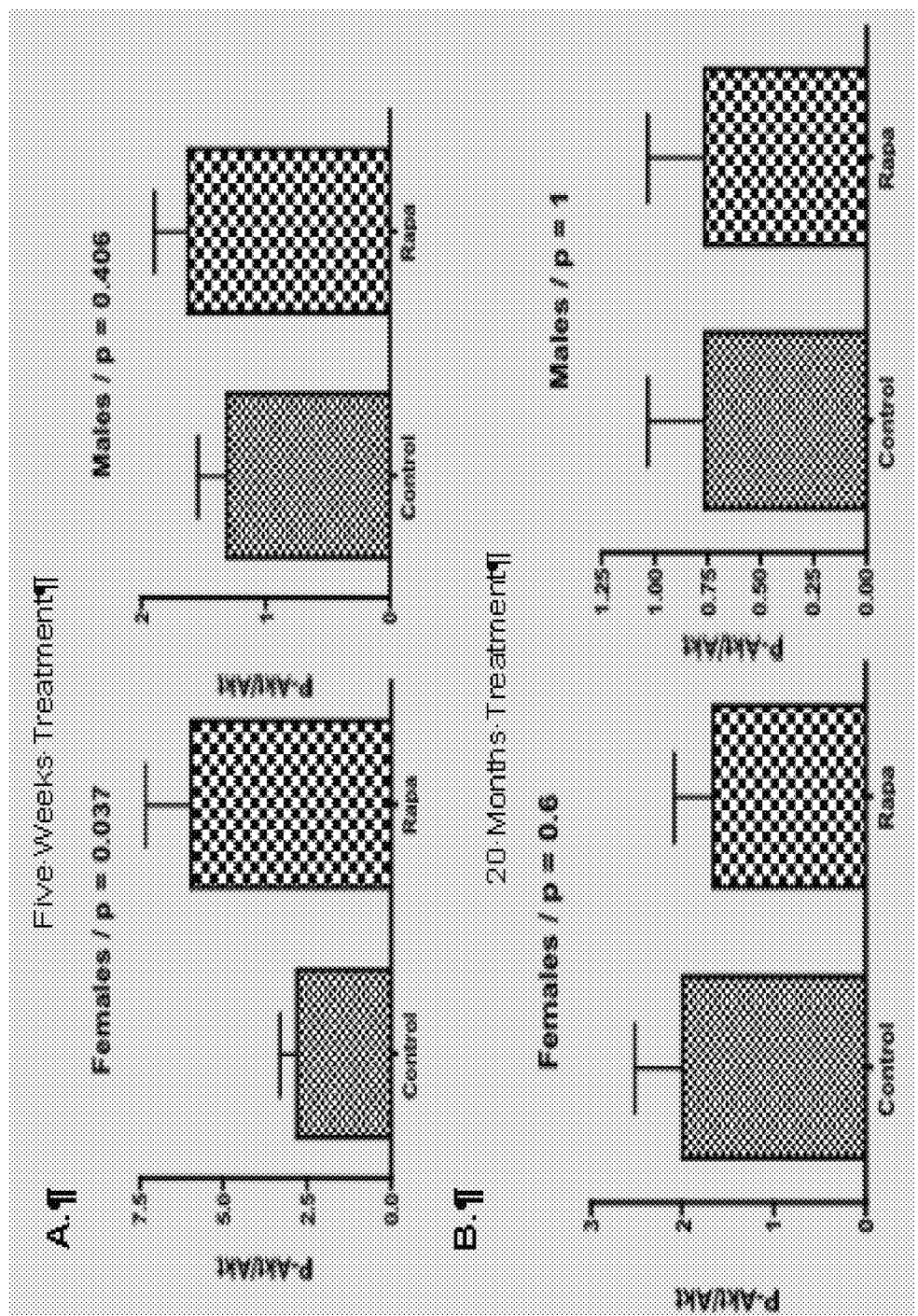
FIG. 34. Short term versus long term treatment with rapamycin in gastrocnemius muscle. Shown are graphs of quantified intensity values P-473Ser Akt/Akt ratios. A) Five week treatment. B) Twenty month treatment. Note that females show a significant increase in Ser473 phosphorylation in females treated for 5 weeks with rapamycin, with the same trend in males. In 20 month treatment, there is no increase in Akt phosphorylation in females or males.

In contrast, visceral fat from mice treated with rapamycin for 20 months does not show this activation, and in males is significantly reduced (FIG. 33). The same trend is seen in skeletal muscle (FIG. 34).

These data suggest that chronic treatment with enterically delivered rapamycin does not enhance tumor promoting activation of Akt, in somatic tissues but rather may reduce it.

If chronic treatment with enteric rapamycin delays cancer or reduces its severity so that it does not present symptomatically until very late in life, one prediction is that the growth-promoting potential of mTORC1 signaling should be repressed in treated mice. In two of monitor mice from cohort 3, two males each with hepatocellular carcinoma were analyzed, one rapamycin-treated the other a control.

FIG. 35 shows immunoassay data from these two tumors, which indicate that chronic enteric rapamycin is significantly repressing the phosphorylation of Thr389 by mTORC1. Thus inhibition of this mTORC1 effector strongly suggests that delayed onset of or less severe cancer is a major mechanism of extended lifespan in mice consuming rapamycin chow. This is also consistent with tumor responses to in calorically and growth factor (dwarf mice) restricted mice. In sum, these data strongly support the concept that prevention of cancer presentation in moderately elderly people by enterically-delivered rapamycin is feasible.

All of the microcapsules, methods, and kits disclosed and claimed herein can be made and executed without undue experimentation in light of the present disclosure. While the microcapsules, methods, and kits of this invention have been described in terms of preferred embodiments, it will be apparent to those of skill in the art that variations may be applied without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. RE37,421; U.S. Pat. Nos. 3,993,749; 4,316,885; 4,401,653; 4,460,722; 4,885,171; 5,023,262; 5,023,262; 5,023,263; 5,023,263; 5,023,264; 5,023,264; 5,078,999; 5,080,899; 5,100,883; 5,100,883; 5,100,883; 5,100,899; 5,102,876; 5,118,677; 5,118,677; 5,118,677; 5,118,678; 5,118,678; 5,120,725; 5,120,725; 5,120,726; 5,120,726; 5,120,727; 5,120,727; 5,120,842; 5,120,842; 5,120,842; 5,130,307; 5,130,307; 5,130,307; 5,138,051; 5,138,051; 5,138,051; 5,151,413; 5,151,413; 5,151,413; 5,162,333; 5,162,333; 5,164,399; 5,164,399; 5,164,399; 5,169,851; 5,169,851; 5,177,203; 5,177,203; 5,194,447; 5,194,447; 5,202,332; 5,202,332; 5,206,018; 5,221,670; 5,221,670; 5,221,740; 5,221,740; 5,233,036; 5,233,036; 5,233,036; 5,260,299; 5,260,299; 5,260,300; 5,260,300; 5,262,423; 5,262,423; 5,262,424; 5,262,424; 5,288,711; 5,302,584; 5,302,584; 5,310,903; 5,344,833; 5,344,833; 5,344,833; 5,346,893; 5,346,893; 5,346,893; 5,358,944; 5,358,944; 5,362,718; 5,362,718; 5,362,718; 5,373,014; 5,373,014; 5,378,696; 5,378,696; 5,378,836; 5,378,836; 5,385,908; 5,385,908; 5,385,909; 5,385,909; 5,385,910; 5,385,910; 5,389,639; 5,389,639; 5,391,730; 5,391,730; 5,411,967; 5,411,967; 5,434,260; 5,434,260; 5,446,048; 5,446,048; 5,446,048; 5,463,048; 5,463,048; 5,480,988; 5,480,988; 5,480,989; 5,480,989; 5,484,790; 5,484,790; 5,484,791; 5,484,791; 5,486,522; 5,486,522; 5,486,523; 5,486,523; 5,486,524; 5,486,524; 5,488,054; 5,488,054; 5,489,595; 5,489,595; 5,489,680; 5,489,680; 5,491,231; 5,491,231; 5,504,091; 5,504,204; 5,504,204; 5,504,291; 5,504,291; 5,508,285; 5,508,285; 5,508,286; 5,508,286; 5,508,290; 5,508,290; 5,508,399; 5,508,399; 5,516,780; 5,516,780; 5,519,031; 5,519,031; 5,521,194; 5,521,194; 5,525,610; 5,525,610; 5,530,007; 5,530,007; 5,530,121; 5,530,121; 5,532,355; 5,532,355; 5,541,191; 5,541,191; 5,541,192; 5,541,192; 5,550,133; 5,550,133; 5,559,112; 5,559,112; 5,559,119; 5,559,119; 5,559,120; 5,559,120; 5,559,122; 5,559,122; 5,561,138; 5,563,145; 5,563,145; 5,567,709; 5,567,709; 5,567,709; 5,637,590; 5,637,590; 5,637,590; 5,665,772; 5,665,772; 5,780,462; 5,780,462; 5,912,253; 5,912,253; 5,922,730; 5,922,730; 5,922,730; 5,955,457; 5,955,457; 5,955,457; 5,985,890; 5,985,890; 6,004,973; 6,004,973; 6,015,809; 6,015,809; 6,200,985; 6,329,386; 6,399,625; 6,440,990; 6,486,099; 6,592,916; 6,653,256; 6,670,355; 6,677,357; 6,680,330; 6,936,644; 7,037,582; 7,160,867; 7,220,755; 7,241,771; 7,268,144; 7,273,874; 7,279,562; 7,282,505; 7,445,916; 7,446,111; 7,455,853; 7,470,682; 7,476,678; 7,538,119; 7,560,457; 7,576,903; U.S. Patent Publns. 20080249123; 20080188511; 20080182867; 20080091008; 20080085880; 20080069797; 20070280992; 20070225313; 20070203172; 20070203171; 20070203170; 20070203169; 20070203168; 20070142423; 20060264453; 20040010002; 20080022965; 20080193653; 20070138673; 20070082829; 20060234053; 20060121122; 20050113282; 20040121155; 20040074089; 20020009473

PCT Appln. WO2008/022256

Aguilar et al., *Cell Metab*, 5:476-487, 2007.
Banko et al., *J. Neurosci.*, 25:9581-9590, 2005.
Berger et al., *Hum. Mol. Genet.*, 115:433-442, 2006.
Billings et al., *Neuron*, 45:675-688, 2005.
Chiang and Abraham, *Trends Mol. Med.*, 13:433-442, 2007.
Choo et al., *Proc. Natl. Acad. Sci. USA*, 105(45):17414-9, 2008.
Das, J. *Bioessays*, 28:890-901, 2006.
Dhalibi et al., *Proc. Natl Acad. Sci. USA*, 101:5524-5529, 2004.
Edwards et al., *Cancer*, 94:2766-2792, 2002.
Galvan et al., *Behav. Brain Res.*, 191:246-255, 2008.
Galvan et al., *Proc. Natl. Acad. Sci. USA*, 103:7130-7135, 2006.
Garber, J. Natl Cancer Inst., 93, 1517-1519 (2001).
Gingras et al., *Genes Dev.*, 15:2852-2864, 2001.
Graziani, *Nat. Prod. Rep.*, 26(5):602-9, 2009.
Gregory et al., *Chem. Int. Ed. Engl.*, 43(19):2551-3, 2004.
Gregory et al., *Org. Biomol. Chem.*, 4 (19):3565-8, 2006.
Guertin and Sabatini, *Cancer Cell*, 12:9-22, 2007.
Harrington et al., *J. Cell Biol.*, 166:213-223, 2004.
Harrington et al., *Trends Biochem Sci.*, 30:35-42, 2005.
Harrison et al., *Nature*, 460:392-395, 2009.
Hill et al., *Mol. Cell Biol.*, 19:7771-7781, 1999.
Hsia et al., *Proc. Natl. Acad. Sci. USA*, 96:3228-3233, 1999.
Hsieh and Papaconstantinou, *Mech. Ageing Dev.*, 125:785-798, 2004.
Janus et al. *Cell Mol. Biol. Lett.*, 10(3):479-98, 2005.
Jia et al., *Development*, 131:3897-3906, 2004.
Kabeya et al., *Embo J.*, 19:5720-5728, 2000.
Kaeberlein and Kennedy, *Aging Cell*, 6:731-734, 2007.
Kaeberlein et al., *Science*, 310:1193-1196, 2005.
Kapahi et al., *Curr. Biol.*, 14:885-890, 2004.
Kim and Chen, *Diabetes*, 53:2748-2756, 2004.
Kohn, In: *Principles of Mammalian Aging*, 2nd Ed., Prentice-Hall, 151, 1978.
Kopelovich et al., *Cancer Epidemiol. Biomarkers Prev.*, 16:1330-1340, 2007.
Lane and Breuleux, *Curr. Opin. Cell Biol.*, 21:219-229, 2009.
Li et al., *Febs J.*, 272:4211-4220, 2005.
Masora, *Mech. Ageing Dev.*, 126:913-922, 2005.
Miller et al., *Aging Cell*, 6:565-575, 2007.
Miller, *Milbank Q.*, 80:155-174, 2002.
Mizushima et al., *Nature*, 395:395-398, 1998.
Morris, *J. Neurosci.* Methods, 11:47-60, 1984.
Mucke et al., *J. Neurosci.*, 20:4050-4058, 2000.
Nadon et al., *AGE*, 30:187-199, 2008.
Oddo et al., *J. Neurosci.*, 28:12163-12175, 2008.
Oddo et al *Proc. Natl. Acad. Sci. USA*, 102:3046-3051, 2005.
Oddo et al., *J. Neurochem.*, 102:1053-1063, 2007.
Oddo et al., *J. Biol. Chem.*, 281:39413-39423, 2006.

Oddo et al., *J. Biol. Chem.*, 281:1599-1604, 2006.
Oddo et al., *Neuron.*, 39:409-421, 2003.
Oddo et al., *Neuron.*, 43:321-332, 2004.
Oddo et al., *Neurobiol. Aging,* 24:1063-1070, 2003.
Paccalin et al., *Dement, Geriatr, Cogn, Disord.,* 22(4):320-6, 2006.
Patti and Kahn, *Nat. Med.,* 10:1049-1050, 2004.
Petroulakis et al., *Br. J. Cancer,* 96(Suppl.):R11-R15, 2007.
Pickford et al., *J. Clin. Invest.,* 118:2190-2199, 2008.
Pong and Zaleska, *Curr. Drug Targets CNS Neurol. Disord.,* 2:349-356, 2003.
Powers et al., *Genes Dev.,* 20:174-184, 2006.
Ravikumar et al., *Nat. Genet.,* 36:585-595, 2004.
Remington's Pharmaceutical Sciences, 18th Ed. Mack Printing Company, 1289-1329, 1990.
Saganich et al., *J. Neurosci.,* 26:13428-13436, 2006.
Schwecke et al., *Proc. Natl. Acad. Sci. USA,* 92(17):7839-43, 1995.
Sharp and Bartke, *J. Gerontol. A Biol. Sci. Med. Sci.,* 60:293-300, 2005.
Shaw and Cantley, *Nature,* 441:424-430, 2006.
Shima et al., *Embo J.,* 17:6649-6659, 1998.
Skeen et al., *Cancer Cell,* 10:269-280, 2006.
Suzuki et al., *EMBO J.,* 20:5971-5981, 2001.
Tremblay et al., *Curr. Opin. Clin. Nutr. Metab. Care,* 8:457-462, 2005b.
Tremblay et al., *Diabetes,* 54:2674-2684, 2005c.
Tremblay et al., *Endocrinology,* 146:1328-1337, 2005a.
Um et al., *Cell Metab.,* 3:393-402, 2006.
Um et al., *Nature,* 431:200-205, 2004.
Vellai et al., *Nature,* 426:620, 2003.
Wan and Helman, *Oncologist,* 12:1007-1018, 2007.
Wang et al., *Mech. Ageing Dev.,* 125:629-632, 2004.
Wullschleger et al., *Cell,* 124:471-484, 2006.
Yeh et al., *Proc. Natl. Acad. Sci. USA,* 92:11086-11090, 1995.
Young and Nickerson-Nutter, *Curr. Opin. Pharmacol.,* 5:418-423, 2005.

The invention claimed is:

1. A microcapsule consisting essentially of a core component comprising at least 5% by weight of an inhibitor of mammalian target of rapamycin (mTOR) which is rapamycin or a rapamycin analog, wherein said core component is microencapsulated and encased in a coating that includes a methyl methacrylate-methacrylic acid copolymer.

2. The microcapsule of claim 1, wherein the coating is Eudragit® S100.

3. The microcapsule of claim 1, wherein the microcapsule comprises rapamycin.

4. The microcapsule of claim 1, wherein the microcapsule comprises an analog of rapamycin that is everolimus, tacrolimus, CCI-779, ABT-578, AP-23675, AP-23573, AP23841, 7-epi-rapamycin, 7-thiomethyl-rapamycin, 7-epi-trimethoxyphenyl-rapamycin, 7-epithiomethyl-rapamycin, 7-demethoxy-rapamycin, 32-demethoxy-rapamycin, 2-desmethylrapamycin, or 42-0-(2-hydroxy)ethyl rapamycin.

5. The microcapsule of claim 1, wherein the core component further comprises a second compound that is vitamin E, vitamin A, an antibacterial antibiotic, an antioxidant, L-carnitine, lipoic acid, metformine, resveratrol, leptine, a non-steroid anti-inflammatory drug, or a COX inhibitor.

6. A kit comprising a first sealed container comprising a microcapsule, wherein the microcapsule is comprised of a core component comprising at least 5% by weight of an inhibitor of mammalian target of rapamycin (mTOR) which is rapamycin or a rapamycin analog, wherein said core component is microencapsulated and encased in a coating that includes a methyl methacrylate-methacrylic acid copolymer.

7. A pharmaceutical or nutraceutical composition comprising a microcapsule as defined in claim 1 for treating or preventing cancer in a mammalian subject, wherein the lifespan expectancy of the mammalian subject is prolonged.

* * * * *